(12) United States Patent
Mandell et al.

(10) Patent No.: US 11,693,017 B2
(45) Date of Patent: *Jul. 4, 2023

(54) SMALL MOLECULE BIOSENSORS

(71) Applicant: President and Fellows of Harvard College, Cambridge, MA (US)

(72) Inventors: Daniel J. Mandell, Brookline, MA (US); Justin Feng, Cambridge, MA (US); Xavier Rios Villanueva, Boston, MA (US); Rajagopal Chari, Brighton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 1058 days.

This patent is subject to a terminal disclaimer.

(21) Appl. No.: 15/760,352

(22) PCT Filed: Jan. 12, 2016

(86) PCT No.: PCT/US2016/013005
§ 371 (c)(1),
(2) Date: Mar. 15, 2018

(87) PCT Pub. No.: WO2017/048316
PCT Pub. Date: Mar. 23, 2017

(65) Prior Publication Data
US 2018/0259541 A1 Sep. 13, 2018

Related U.S. Application Data

(60) Provisional application No. 62/220,628, filed on Sep. 18, 2015.

(51) Int. Cl.
*G01N 33/74* (2006.01)
*C07K 14/00* (2006.01)
(Continued)

(52) U.S. Cl.
CPC .......... *G01N 33/743* (2013.01); *C07K 14/00* (2013.01); *C12N 9/22* (2013.01); *C12N 15/11* (2013.01);
(Continued)

(58) Field of Classification Search
CPC ...... C07K 14/00; C07K 2319/00; C12N 9/22; C12N 15/11; C12N 15/62; C12N 15/63;
(Continued)

(56) References Cited

U.S. PATENT DOCUMENTS

2010/0112634 A1 5/2010 Spagnoli et al.
2014/0065711 A1 3/2014 Liu et al.
(Continued)

FOREIGN PATENT DOCUMENTS

WO 2014/018423 A2 1/2014
WO 2015/017866 A1 2/2015

OTHER PUBLICATIONS

Pan et al. "Structure and function of the Zn(II) binding site within the DNA-binding domain of the GAL4 transcription factor" Proc. Natl. Acad. Sci. USA, vol. 86, pp. 3145-3149, May 1989 (Year: 1989).*

(Continued)

*Primary Examiner* — Jeremy C Flinders
(74) *Attorney, Agent, or Firm* — Banner & Witcoff, Ltd.

(57) ABSTRACT

Biosensors for small molecules can be used in applications that range from metabolic engineering to orthogonal control of transcription. Biosensors are produced based on a ligand-binding domain (LBD) using a method that, in principle, can be applied for any target molecule. The LBD is fused to either a fluorescent protein or a transcriptional activator and is destabilized by mutation such that the fusion accumulates only in cells containing the target ligand. The power of this method is illustrated by developing biosensors for digoxin (Continued)

and progesterone. Addition of ligand to cells expressing a biosensor activates transcription in yeast, mammalian cells and plants, with a dynamic range of up to about 100-fold or more. The biosensors are used to improve the biotransformation of pregnenolone to progesterone in yeast and to regulate CRISPR activity in mammalian cells. This work provides a general methodology to develop biosensors for a broad range of molecules.

9 Claims, 29 Drawing Sheets

Specification includes a Sequence Listing.

(51) Int. Cl.
    *C12N 15/62*     (2006.01)
    *C12N 15/63*     (2006.01)
    *C12N 9/22*     (2006.01)
    *C12N 15/11*     (2006.01)
    *C12N 15/90*     (2006.01)

(52) U.S. Cl.
    CPC .............. *C12N 15/62* (2013.01); *C12N 15/63* (2013.01); *C12N 15/902* (2013.01); *C07K 2319/00* (2013.01); *C12N 2310/20* (2017.05); *C12N 2320/50* (2013.01); *C12N 2800/22* (2013.01); *C12N 2800/80* (2013.01)

(58) Field of Classification Search
    CPC .............. C12N 15/902; C12N 2310/20; C12N 2320/50; C12N 2800/22; C12N 2800/80; G01N 33/743

See application file for complete search history.

(56) References Cited

U.S. PATENT DOCUMENTS

2014/0273226 A1     9/2014     Wu
2015/0184199 A1     7/2015     Horwitz et al.

OTHER PUBLICATIONS

Shoulders et al. (J. Amer. Chem. Soc., 2013, 135:8129-8132) (Year: 2013).*
Arnold et al. (The EMBO Journal, 2018, 37:e98896) (Year: 2018).*
Hirai et al. (Int. J. Dev. Biol., 2010, 54:1589-1596) (Year: 2010).*
Banaszynski et al. "A Rapid, Reversible, and Tunable Method to Regulate Protein Function in living Cells Using Synthetic Small Molecules," Cell, Sep. 8, 2006 (Sep. 8, 2006), vol. 126, pp. 995-1004. entire document.
Feng et al. "A general strategy to construct small molecule biosensors in eukaryotes." elife, Dec. 30, 2015 (Dec. 30, 2015), vol. 4, e10606, pp. 1-22. entire document.
Fu et al. "High-frequency off-target mutagenesis induced by CrIsPr-Cas nucleases in human cells," Nature Biotechnology, Jun. 23, 2013; (Jun. 23, 2013), vol. 31, No. 9, pp. 822-826. entire document.
Tinberg et al. "Computational Design of Ligand Binding Proteins with High Affinity and Selectivity," Nature, Sep. 12, 2013 (Sep. 12, 2013), vol. 501, pp. 212-216. entire document.

* cited by examiner

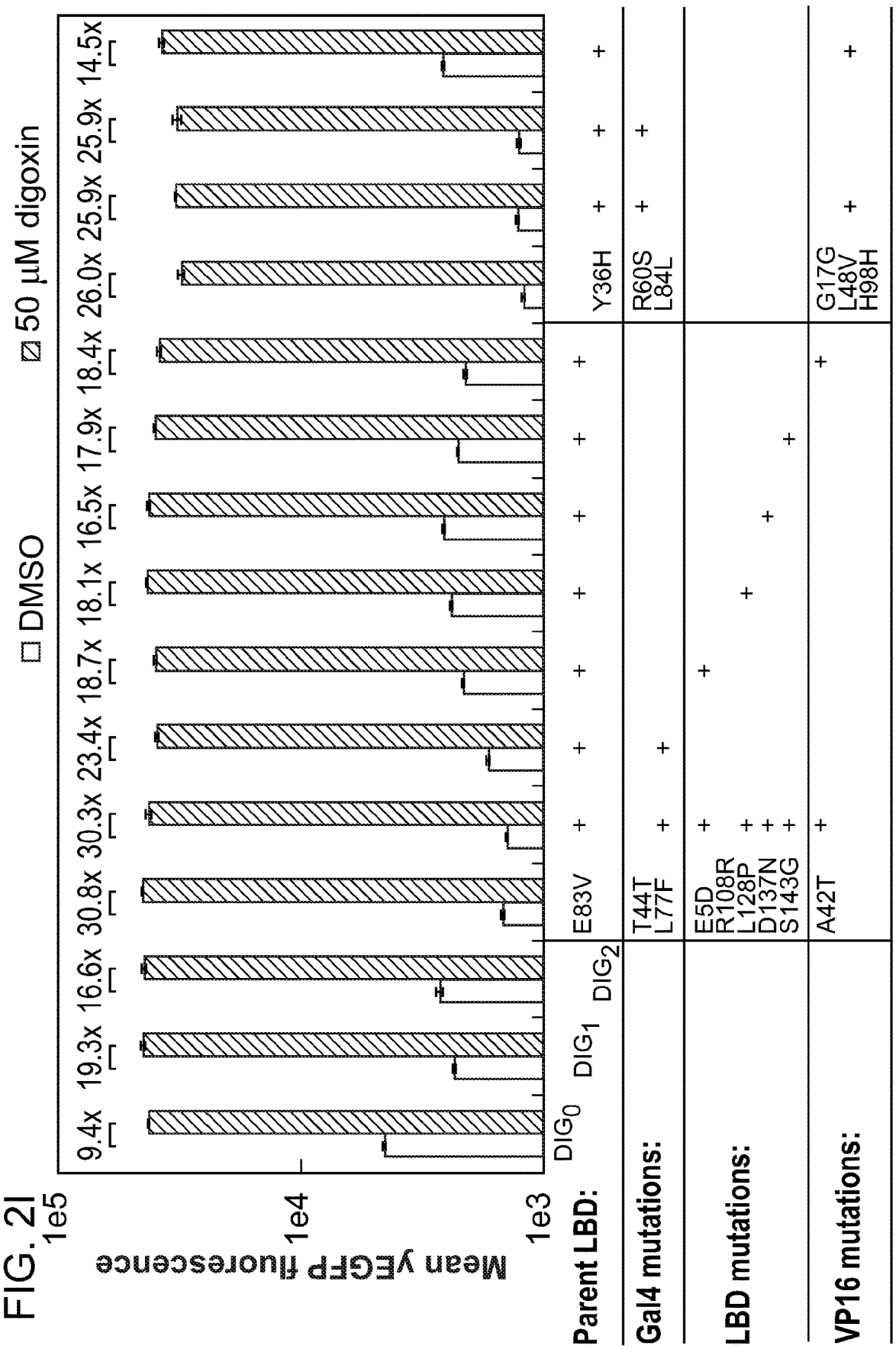

Construct:
Gal4-DIG$_0$-VP64
deg-Gal4-DIG$_0$-VP64
Gal4-deg-DIG$_0$-VP64
Gal4-DIG$_0$-deg-VP64
Gal4-DIG$_0$-VP64-deg
deg-Gal4-DIG$_0$-VP16
deg-Gal4-DIG$_1$-VP16

DMSO    10 μM digoxigenin    100 μM digoxigenin

■ PyE1
♦ PyE1 pdr5Δ

[digoxigenin] (μM)

no steroid

10 µM progesterone

10 µM pregnenolone

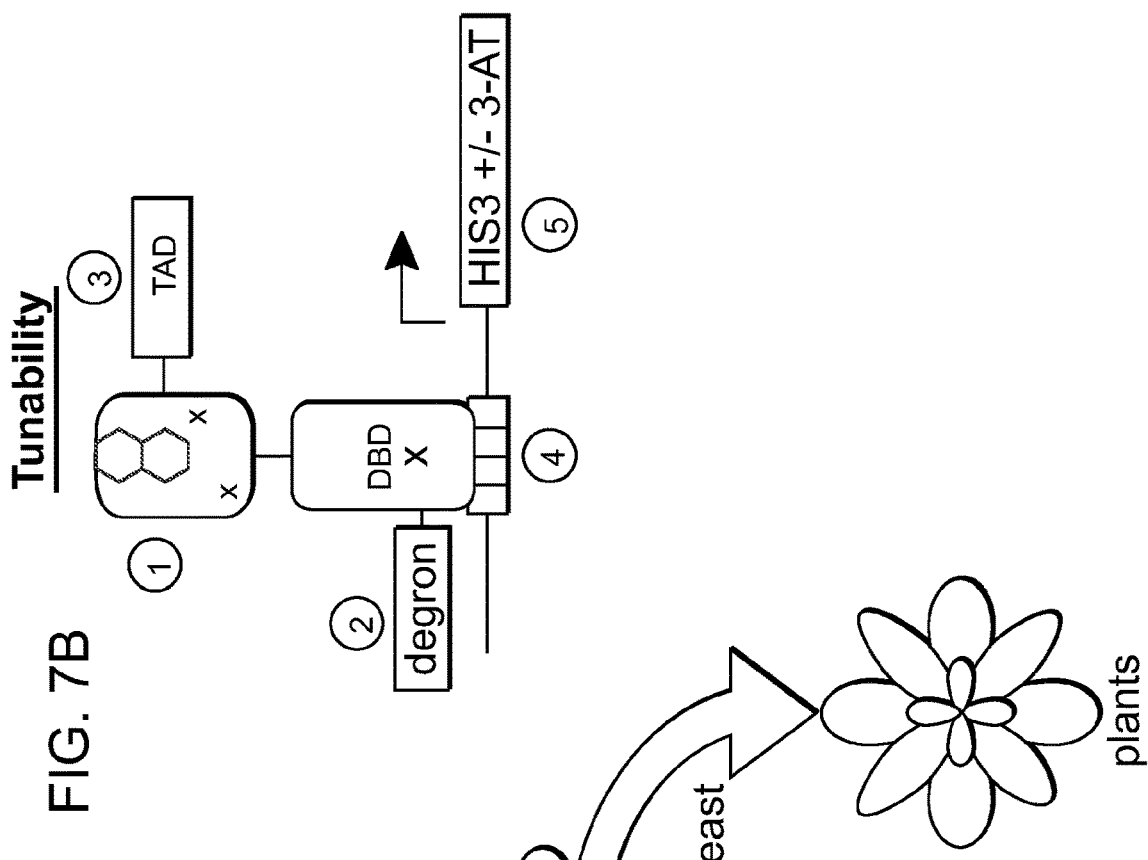
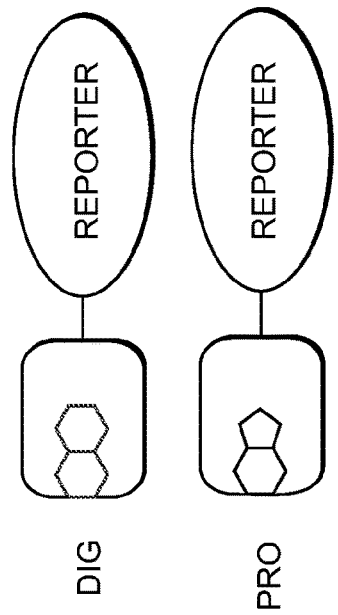
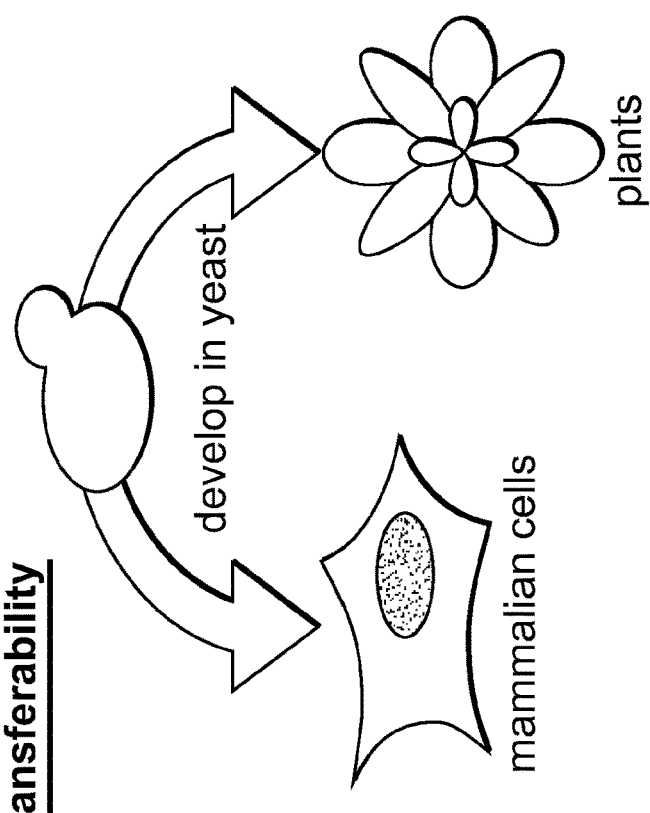
FIG. 7A  Ligand Generality
FIG. 7B  Tunability
FIG. 7C  Transferability

SEQUENCE LISTING

```
<160> NUMBER OF SEQ ID NOS: 2

<210> SEQ ID NO 1
<211> LENGTH: 8
<212> TYPE: PRT
<213> ORGANISM: Artificial
<220> FEATURE:
<223> OTHER INFORMATION: Residue linker sequence

<400> SEQUENCE: 1

Gly Gly Ser Gly Gly Ser Gly Gly
1               5

<210> SEQ ID NO 2
<211> LENGTH: 5
<212> TYPE: PRT
<213> ORGANISM: Artificial
<220> FEATURE:
<223> OTHER INFORMATION: Cas9 promoter

<400> SEQUENCE: 2

Cys Ala Gly Gly Ser
1               5
```

SMALL MOLECULE BIOSENSORS

RELATED APPLICATIONS

This application is a National Stage Application under 35 U.S.C. 371 of PCT application PCT/US2016/013005 designating the United States and filed Jan. 12, 2016; which claims the benefit of U.S. provisional application No. 62/220,628 and filed Sep. 18, 2015 each of which are hereby incorporated by reference in their entireties.

STATEMENT OF GOVERNMENT INTERESTS

This invention was made with government support under DE-FG02-02ER63445 awarded by the U.S. Department of Energy. The government has certain rights in the invention.

FIELD

Embodiments of the present disclosure relate in general to a biosensor including ligand binding domains (LBDs) engineered to conditionally respond to the presence of specific small molecules, the biosensors including LBDs which are fused to reporter proteins or transcription factors (TFs).

BACKGROUND

Biosensors capable of sensing and responding to small molecules in vivo have wide-ranging applications in biological research and biotechnology, including metabolic pathway regulation, Zhang, F., Carothers, J. M. & Keasling, J. D., Design of a dynamic sensor-regulator system for production of chemicals and fuels derived from fatty acids. Nat. Biotechnol., 30, 354-9 (2012), biosynthetic pathway optimization, Raman, S., Rogers, J. K., Taylor, N. D. & Church, G. M., Evolution-guided optimization of biosynthetic pathways. Proc. Natl. Acad. Sci., 201409523 (2014). doi:10.1073/pnas.1409523111 and Tang, S.-Y. & Cirino, P. C. Design and application of a mevalonate-responsive regulatory protein. Angew. Chem. Int. Ed. Engl., 50, 1084-6 (2011), metabolite concentration measurement and imaging, Paige, J. S., Nguyen-Duc, T., Song, W. & Jaffrey, S. R. Fluorescence Imaging of Cellular Metabolites with RNA. Science (80), 335, 1194-1194 (2012), environmental toxin detection, Gil, G. C., Mitchell, R. J., Chang, S. T. & Gu, M. B. A biosensor for the detection of gas toxicity using a recombinant bioluminescent bacterium. Biosens. Bioelectron., 15, 23-30 (2000), and small molecule-triggered therapeutic response, Ye, H. et al., Pharmaceutically controlled designer circuit for the treatment of the metabolic syndrome. Proc. Natl. Acad. Sci. U.S.A., 110, 1-6 (2012). Despite such broad utility, no single strategy for the construction of biosensors has proven sufficiently generalizable to gain widespread use. Current methods typically couple binding to a single output signal, and use a limited repertoire of natural protein, Tang, S. Y. et al., Screening for enhanced triacetic acid lactone (TAL) production by recombinant Escherichia coli expressing a designed TAL reporter. J. Am. Chem. Soc., (2013). doi:10.1021/ja402654z, or nucleic acid aptamer-binding, Yang, J. et al., Synthetic RNA devices to expedite the evolution of metabolite-producing microbes. Nat. Commun., 4, 1413 (2013), domains, which narrows the scope of small molecules that can be detected. A general solution to small molecule biosensing should be adaptable to a range of small molecules and responses.

A promising approach to biosensor design in eukaryotes uses conditionally stable ligand-binding domains (LBDs). See Banaszynski, L. a, Chen, L.-C., Maynard-Smith, L. a, Ooi, A. G. L. & Wandless, T. J. A rapid, reversible, and tunable method to regulate protein function in living cells using synthetic small molecules. Cell, 126, 995-1004 (2006) and Tucker, C. L. & Fields, S. A yeast sensor of ligand binding. Nat. Biotechnol., 19, 1042-6 (2001). In the absence of a cognate ligand, these proteins are degraded by the ubiquitin proteasome system, Egeler, E. L., Urner, L. M., Rakhit, R., Liu, C. W. & Wandless, T. J. Ligand-switchable substrates for a ubiquitin-proteasome system. J. Biol. Chem., 286, 31328-36 (2011). Binding to the ligand stabilizes the LBD and prevents degradation. Fusing the destabilized LBD to a suitable reporter protein, such as an enzyme, fluorescent protein, or transcription factor, renders the fusion conditionally stable and generates sensor response. Naturally-occurring LBDs can be engineered to be conditionally stable, Banaszynski, L. a, Chen, L.-C., Maynard-Smith, L. a, Ooi, A. G. L. & Wandless, T. J. A rapid, reversible, and tunable method to regulate protein function in living cells using synthetic small molecules. Cell, 126, 995-1004 (2006); Miyazaki, Y., Imoto, H., Chen, L. & Wandless, T. J. Destabilizing domains derived from the human estrogen receptor. J. Am. Chem. Soc., 134, 3942-5 (2012); Iwamoto, M., Björklund, T., Lundberg, C., Kirik, D. & Wandless, T. J. A general chemical method to regulate protein stability in the mammalian central nervous system. Chem. Biol., 17, 981-8 (2010), making it possible in principle to convert any LBD into a biosensor for a target ligand. Designed LBDs can be used in cases for which natural binding proteins do not exist or lack sufficient specificity or bio-orthogonality.

SUMMARY

A single designed LBD scaffold is converted into multiple highly specific biosensors for the clinically relevant steroids digoxin and progesterone (FIG. 1A). LBDs fused to fluorescent reporters were engineered to be conditionally stable in the budding yeast *Saccharomyces cerevisiae*. Attaching these conditionally-stabilized LBDs to transcription factors (TFs) yields biosensors with increased activation by their target ligands. The TF-biosensors are used to improve the biosynthetic yield of progesterone in yeast.

The biosensors retain function when ported directly into mammalian cells, with up to 100-fold (or more) activation over background, allowing for tight control of CRISPR/Cas9 genome editing. The biosensors also show 35-fold activation by ligand in *Arabidopsis thaliana*. The method presented here enables the rapid development of eukaryotic biosensors from natural and designed binding domains.

Fluorescent Biosensors Built from Engineered LBDs

LBDs intended for biosensor development should recognize their targets with high affinity and specificity. Computationally-designed binding domain DIG10.3, Tinberg, C. E. et al., Computational design of ligand-binding proteins with high affinity and selectivity, Nature, 501, 212-6 (2013), hereafter DIG0, binds the plant steroid glycoside digoxin and its aglycone digoxigenin with picomolar affinities. Introduction of three rationally-designed binding site mutations into DIG0 resulted in a progesterone binder (PRO0) with nanomolar affinity, Tinberg, C. E. et al., Computational design of ligand-binding proteins with high affinity and selectivity, Nature, 501, 212-6 (2013). Genetic fusions were constructed of DIG0 and PRO0 fused to a yeast-enhanced GFP (LBD-biosensors DIG0-GFP and PRO0-GFP) and constitutively expressed them in *S. cerevisiae*. The fusions showed little change in fluorescence in response to digoxin or progesterone, respectively (FIGS. 1B and 1C).

Work by Wandless and co-workers has shown that mutagenesis of LBDs can be used to identify variants that are stable only in the presence of a target ligand. See Banaszynski, L. a, Chen, L.-C., Maynard-Smith, L. a, Ooi, A. G. L. & Wandless, T. J. A rapid, reversible, and tunable method to regulate protein function in living cells using synthetic small molecules. Cell, 126, 995-1004 (2006). LBDs of DIG0-GFP and PRO0-GFP were randomly mutagenized by error-prone PCR and subjected libraries of $10^5$ integrants to multiple rounds of FACS, sorting alternately for high fluorescence in the presence of the ligand and low fluorescence in its absence. LBD variants having greater than 5-fold activation by cognate ligand were isolated (FIG. 1E). By making additional variants that contain single mutations of the up to four mutations found in the progesterone biosensors, it was shown that some mutations are additive, while others predominately contribute to sensitivity (FIG. 1E).

Many of the conditionally-destabilizing mutations identified for DIG0 involve residues participating in key dimer interface interactions (FIG. 1D). The conditionally-destabilizing mutations of PRO0 are located throughout the protein (FIGS. 1F-H); the DIG0 interface mutations also rendered PRO0-GFP conditionally stable on binding progesterone (FIG. 1I).

TF-Biosensors Amplify Ligand-Dependent Responses

To improve the dynamic range and utility of the biosensors, conditionally-stable LBD transcription factor fusions (TF-biosensors) were built by placing an LBD between an N-terminal DNA binding domain (DBD) and a C-terminal transcriptional activation domain (TAD) (FIG. 2A).

The use of TFs serves to amplify biosensor response and allows for ligand-dependent control of gene expression. See Shoulders, M. D., Ryno, L. M., Cooley, C. B., Kelly, J. W. & Wiseman, R L. Broadly applicable methodology for the rapid and dosable small molecule-mediated regulation of transcription factors in human cells. J. Am. Chem. Soc., 135, 8129-8132 (2013); Beerli, R. R., Schopfer, U., Dreier, B. & Barbas, C. F. Chemically regulated zinc finger transcription factors. J. Biol. Chem., 275, 32617-32627 (2000); Louvion, J. F., Havaux-Copf, B. & Picard, D. Fusion of GAL4-VP16 to a steroid-binding domain provides a tool for gratuitous induction of galactose-responsive genes in yeast, Gene, 131, 129-134 (1993). Initial constructs used the DBD of Gal4, the destabilized LBD mutant DIG1 (E83V), and either the TAD VP16 or VP64 to drive the expression of yEGFP from a GAL1 promoter. The dynamic range of TF-biosensor activity was maximal when the biosensor was expressed using a weak promoter and weak activation domain because of lower background activity in the absence of ligand (FIGS. 2G and 2H).

Gal4-DIG1-VP16 (hereafter G-DIG1-V) was chosen for further TF-biosensor development because it has both a large dynamic range and maximal activation by ligand. A FACS-based screen of an error-prone PCR library of G-DIG0-V, G-DIG1-V, and G-DIG2-V variants identified mutations L77F and R60S in the Gal4 dimer interface (hereafter GL77F, GR60S) that further increased TF biosensor response by lowering background activity in the absence of ligand (FIGS. 2B and 2I).

Although these Gal4 mutations were identified by screening libraries of digoxin-dependent TF-biosensors, they also increased progesterone-dependent activation of the G-PRO-V series of biosensors, indicating a shared mechanism of conditional stability in both systems (FIG. 2J). Combining mutations in Gal4 and DIG or PRO led to activations of up to 60-fold by cognate ligand, a ten-fold improvement over the most responsive LBD-biosensors (FIGS. 2C and 2D), and a dynamic range that has been challenging to achieve in yeast, Rakhit, R., Edwards, S. R. S., Iwamoto, M. & Wandless, T. J. Evaluation of FKBP and DHFR based destabilizing domains in *Saccharomyces cerevisiae*. Bioorganic Med., 21, 4965-4968 (2011). The TF-biosensors were also rapidly activated, showing a fivefold increase in signal after one hour of incubation with ligand and full activation after ~14 hours (FIGS. 2E and 2F).

TF-Biosensors are Tunable and Modular

An attractive feature of the TF-biosensors is that the constituent parts—the DBD/promoter pair, the LBD, the TAD, the reporter, and the yeast strain—are modular, such that the system can be modified for additional applications. To demonstrate tunability, the DBD of GDIG1-V were placed with the bacterial repressor LexA and inserted DNA-binding sites for LexA into the GAL1 promoter. Only when the promoter driving reporter expression contained LexA-binding sites, LexA-based TF-biosensors with DIG1 and a weak TAD, B42, produced nearly 40-fold activation in the presence of digoxin (FIGS. 3A and 3C). These results demonstrate that the biosensors can function with different combinations of DBDs and TADs, which could produce diverse behaviors and permit their use in eukaryotes requiring different promoters. Furthermore, the reporter gene can be swapped with an auxotrophic marker gene for growth selections. The TF-biosensors drove expression of the HIS3 reporter more effectively when steroid was added to the growth media, as assessed by growth of a histidine auxotrophic strain in media lacking histidine (FIGS. 3B and 3D). Fusion of the Matα2 degron to the biosensor improved dynamic range by reducing growth of yeast in the absence of ligand. Finally, the host strain could be modified to improve biosensor sensitivity toward target ligands by deletion of the gene for a multidrug efflux pump, Ernst, R., Klemm, R., Schmitt, L. & Kuchler, K. Yeast ATP-binding cassette transporters: cellular cleaning pumps Methods Enzymol., 400, 460-84 (2005), thereby increasing ligand retention (FIG. 3C-D).

TF-Biosensors Enable Selectable Improvements to Bioproduction of Small Molecules in Yeast Improving bioproduction requires the ability to detect how modifications to the regulation and composition of production pathways affect product titers. Current product detection methods such as mass spectrometry or colorimetric assays are low-throughput and are not scalable or generalizable. LBD- and TF-biosensors could be coupled to fluorescent reporters to enable high throughput library screening or to selectable genes to permit rapid evolution of biosynthetic pathways, Tang, S.-Y. & Cirino, P. C. Design and application of a mevalonate-responsive regulatory protein. Angew. Chem. Int. Ed. Engl., 50, 1084-6 (2011); Dietrich, J. a, McKee, A. E. & Keasling, J. D. High-throughput metabolic engineering: advances in small-molecule screening and selection. Annu. Rev. Biochem., 79, 563-590 (2010); Chou, H. H. & Keasling, J. D. Programming adaptive control to evolve increased metabolite production. Nat. Commun. 4, 2595 (2013). Yeast-based platforms have been developed for the biosynthesis of pharmaceutically relevant steroids, such as progesterone and hydrocortisone, Duport, C., Spagnoli, R., Degryse, E. & Pompon, D. Self-sufficient biosynthesis of pregnenolone and progesterone in engineered yeast. Nat. Biotechnol. 16, 186-9 (1998); Szczebara, F. M. et al., Total biosynthesis of hydrocortisone from a simple carbon source in yeast. Nat. Biotechnol. 21, 143-9 (2003). A key step in the production of both steroids is the conversion of pregnenolone to progesterone by the enzyme 3β-hydroxysteroid dehydrogenase (3β-HSD).

A progesterone biosensor was used to detect and improve this transformation. An important feature of biosensors intended for pathway engineering is the ability to detect a product with minimal activation by substrate or other related chemicals. TF-biosensors built from PRO1 showed the greatest dynamic range and selectivity for progesterone over pregnenolone when driving yEGFP expression or when coupled to a HIS3 reporter assay (FIGS. 4A, 4B, and FIGS. 4G-4J). It was investigated as to whether this sensor could be used to detect the in vivo conversion of pregnenolone to progesterone by episomally-expressed 3β-HSD (FIG. 4C). Using GL77F-PRO1-V driving a yEGFP reporter, progesterone production could be detected, with biosensor response greatest when 3β-HSD was expressed from a high copy number plasmid and from a strong promoter (FIG. 4D).

Use the biosensor to improve this enzymatic transformation was sought. To select for improved progesterone production, a growth assay was required in which wild-type 3β-HSD could no longer complement histidine auxotrophy when the yeast were grown on plates supplemented with pregnenolone. To this end, the selection stringency was tuned by adding the His3 inhibitor 3-aminotriazole (FIG. 4K). The 3β-HSD coding sequence was mutangenized using error-prone PCR and screened colonies that survived the HIS3 selection for their yEGFP activation by pregnenolone. By transforming evolved 3β-HSD mutations into a fresh host background, it was shown that the mutations in the enzyme, and not off-target plasmid or host escape mutations, were responsible for increased biosensor response (FIG. 4E). Two of the mutants, 3β-HSD N139D and 3β-HSD F67Y, were assayed for progesterone production using gas chromatography and mass spectrometry and were found to produce two-fold more progesterone per OD than cells bearing the wild-type enzyme (FIG. 4F).

Yeast-Based Biosensors Port Directly to Mammalian Cells and Tightly Regulate CRISPR/Cas9 Genome Editing Yeast is an attractive platform for engineering in vivo biosensors because of its rapid doubling time and tractable genetics. If yeast-derived biosensors function in more complex eukaryotes, the design-build-test cycle in those organisms could be rapidly accelerated. First, the portability was assessed of yeast TF-biosensors to mammalian cells. Single constructs containing digoxin and progesterone TF-biosensors with the greatest dynamic ranges (without codon optimization) were stably integrated into human K562 cells using PiggyBac transposition.

The dynamics of the TF-biosensors were characterized in human cells by dose response and time course assays similar to the yeast experiments (FIGS. 5A-D). As with yeast, the human cells demonstrated greater sensitivity to digoxin, with fluorescence activation peaking at 100 nM of cognate ligand for digoxin biosensors and 1 mM for progesterone biosensors. Greater than 100-fold activation was observed for the most sensitive progesterone biosensor GL77F-PRO1-V. The increase in mammalian dynamic range over yeast may arise from more aggressive degradation of destabilized biosensors or greater accumulation of target-stabilized biosensors or reporters. The time course data show that fluorescence increased four-fold within four hours of target introduction and rose logarithmically for 24-48 hours.

Next, these biosensors were assessed whether or not they could drive more complex mammalian phenotypes. The CRISPR/Cas9 system has proved to be an invaluable tool for genome editing. See Mali, P. et al., RNA-Guided Human Genome Engineering via Cas9. Science 11, 367-79 (2013); DiCarlo, J. E. et al., Genome engineering in *Saccharomyces cerevisiae* using CRISPR-Cas systems. Nucleic Acids Res. 41, 1-8 (2013); Gratz, S. J. et al., Genome engineering of Drosophila with the CRISPR RNA-guided Cas9 nuclease. Genetics 194, 1029-1035 (2013); Hwang, W. Y. et al., Efficient genome editing in zebrafish using a CRISPR-Cas system., Nat. Biotechnol. 1-3 (2013). doi:10.1038/nbt.2501. Despite the high programmability and specificity of Cas9-mediated gene editing achieved to date, unchecked Cas9 activity can lead to off-target mutations and cytotoxicity. See Fu, Y. et al., High-frequency off-target mutagenesis induced by CRISPR-Cas nucleases in human cells. Nat. Biotechnol. 31, 822-6 (2013); Mali, P. et al., CAS9 transcriptional activators for target specificity screening and paired nickases for cooperative genome engineering. Nat. Biotechnol. 31, 833-8 (2013); Pattanayak, V. et al., High-throughput profiling of off-target DNA cleavage reveals RNA programmed Cas9 nuclease specificity. Nat. Biotechnol. 31, 839-43 (2013). Further, it may be desirable to tightly regulate Cas9 activity such that gene editing occurs only in defined conditions.

To facilitate inducible gene editing, human codon-optimized versions of the DIG3 and PRO1 LBDs were fused to the N-terminus of Cas9 from *S. pyogenes*. This construct was integrated into a reporter cell line containing an EGFP variant with a premature stop codon that renders it non-functional. Upon separate stable integration of the DIG-Cas9 and PRO-Cas9 fusions, a guide RNA was transfected targeting the premature stop codon as well as a donor oligonucleotide containing the sequence to restore EGFP activity via homologous recombination. After a 48-hour incubation period, an ~18-fold increase in GFP positive cells was observed with digoxigenin relative to the mock control (FIG. 5E).

Environmental Detection in the Plant *Arabidopsis thaliana*

To assess generalizability of these biosensors to multicellular organisms, G-DIG1-V was engineered to function as an environmental sensor in plants. The DIG1 sequence was codon optimized for expression in *Arabidopsis thaliana*. Biosensor fusions to two different degrons, Matα2 from yeast and DREB2a from *Arabidopsis*, Sakuma, Y. et al., Dual function of an *Arabidopsis* transcription factor DREB2A in water stress-responsive and heat-stress-responsive gene expression. Proc. Natl. Acad. Sci. U.S.A. 103, 18822-18827 (2006), and the VP16 and VP64 variants of the TAD were tested. Initially the G-DIG1-TAD variants with a transient expression assay using *Arabidopsis* protoplasts and a reporter gene consisting of firefly luciferase under the control of a Gal4-activated plant promoter (pUAS::Luc) were tested.

The biosensor containing the Matα2 degron and VP16 TAD showed the highest fold activation of luciferase in the presence of digoxigenin (FIG. 6C). Next, the genes encoding G-DIG1-V-Matα2 and the Gal4-activated pUAS::Luc were inserted into a plant transformation vector and stably transformed them into *Arabidopsis* plants. Primary transgenic plants were screened in vivo for digoxigenin-dependent luciferase production, and responsive plants were allowed to set seed for further testing. Second generation transgenic plants (T1, heterozygous) were tested for digoxin- or digoxigenin-independent induction of luciferase expression. After 42 hours, 30-50 fold induction of luciferase activity was observed in digoxigenin-treated plants compared to the uninduced control (FIGS. 6A-F).

Both digoxin and digoxigenin are capable of inducing the biosensor. Digoxigenin-dependent luciferase induction was observed in multiple independent transgenic T1 lines, and an exponential dose response to digoxigenin was observed in the transgenic plants (FIGS. 6C-6D). The specificity of the digoxigenin biosensor in plants parallels that in yeast cells (FIGS. 6E and 6F).

BRIEF DESCRIPTION OF THE DRAWINGS

The foregoing and other features and advantages of the present disclosure will be more fully understood from the following detailed description of illustrative embodiments taken in conjunction with the accompanying drawings in which:

FIG. 1I graphically depicts fold activation of PRO0-GFP biosensors with digoxin biosensor mutations upon addition of 50 µM progesterone.

FIG. 2I depicts individual mutations identified in a FACS analysis of an error-prone PCR library of G-DIG-V biosensors were tested for their effect on biosensor function using digoxigenin. Transformants were analyzed in a yEGFP yeast reporter strained containing a deletion in pdr5 (PyE14). Improvements in fold activation relative to parental sequences were localized to mutations in Gal4.

FIG. 4A graphically depicts fold activation of GL77F-PRO1-V by a panel of steroids in yEGFP reporter strain PyE1. Data are represented as mean±SEM.

FIG. 4B depicts growth of degron-G-PRO1-V in HIS3 reporter strain PJ69-4a that is stimulated by progesterone but not pregnenolone.

FIG. 4C is a schematic for directed evolution of 3β-HSD using TF-biosensors for conversion of pregnenolone to progesterone.

FIG. 4D depicts fold activation of GL77F-PRO1-V by a panel of plasmids expressing wild-type 3β-HSD under varying promoter strengths in yEGFP reporter strain PyE1 when incubated in 50 µM pregnenolone. Data for plasmids containing CEN/ARS and 2µ (2 micron) origins are shown. Data are presented as mean±s.e.m. of three technical replicates. (−) indicates cells lacking 3β-HSD.

FIG. 4E depicts fold activation of GL77F-PRO1-V by a panel of evolved 3β-HSD mutants expressed under the TDH3 promoter on a CEN/ARS plasmid and incubated in 50 μM pregnenolone.

FIG. 4F depicts progesterone titer in 1 OD of cells produced by strains expressing 3β-HSD mutants. Data are presented as mean±s.e.m. of three biological replicates.

FIGS. 4G-4J depict specificity of PRO biosensors enables selection for auxotrophy complementation.

FIG. 4G graphically depicts specificity for progesterone (PRO) over digoxigenin (DIG), digoxin (DGX), digitoxigenin (DTX), pregnenolone (PRE), β-estradiol (B-EST), and hydrocortisone (HYD) for G-PRO0-V.

FIG. 4H graphically depicts specificity for progesterone (PRO) over digoxigenin (DIG), digoxin (DGX), digitoxigenin (DTX), pregnenolone (PRE), β-estradiol (B-EST), and hydrocortisone (HYD) for G-PRO1-V.

FIG. 4I graphically depicts specificity for progesterone (PRO) over digoxigenin (DIG), digoxin (DGX), digitoxigenin (DTX), pregnenolone (PRE), β-estradiol (B-EST), and hydrocortisone (HYD) for G-PRO2-V.

FIG. 4J graphically depicts specificity for progesterone (PRO) over digoxigenin (DIG), digoxin (DGX), digitoxigenin (DTX), pregnenolone (PRE), β-estradiol (B-EST), and hydrocortisone (HYD) for G-PRO3-V.

FIG. 4K depicts images of growth response of yeast strain PyE1 transformed with β-HSD on CEN/ARS plasmids under various promoters and plated on SC-his (and -ura-leu for plasmid maintenance) containing titrations of 3-AT and either 0.5% DMSO (upper panels) or 50 μM pregnenolone (lower panels).

FIG. 5A graphically depicts the concentration dependence of response to digoxin for constructs containing digoxin TF-biosensors and Gal4 UASE1b-EGFP reporter individually integrated into K562 cells. GR60S,L77F-PRO1-V serves as a digoxin insensitive control.

FIG. 5B graphically depicts the concentration dependence of response to progesterone for constructs containing progesterone TF-biosensors and Gal4 UAS-E1b-EGFP reporter individually integrated into K562 cells. GR60S-DIG1-V serves as a progesterone insensitive control.

FIG. 5C graphically depicts the time dependence of response to 100 nM digoxin for constructs containing digoxin TF-biosensors and Gal4 UAS-E1b-EGFP reporter individually integrated into K562 cells. GR60S,L77F-PRO1-V serves as a digoxin insensitive control.

FIG. 5D graphically depicts the time dependence of response to 25 μM progesterone for constructs containing progesterone TF-biosensors and Gal4 UAS-E1b-EGFP reporter individually integrated into K562 cells. GR60S-DIG1-V serves as a progesterone insensitive control.

FIG. 5E depicts DIG3 and PRO1 fused to the N-terminus of S. pyogenes Cas9 that were integrated into a K562 cell line containing a broken EGFP. EGFP function is restored upon transfection of a guide RNA and donor oligonucleotide with matching sequence in the presence of active Cas9. Data are presented as mean±s.e.m. across three biological replicates.

FIG. 7A illustrates a schematic of biosensors for small molecules are modularly constructed by replacing the LBD with proteins possessing altered substrate preferences.

FIG. 7B is an activity schematic of the biosensor that can be tuned by 1) introducing destabilizing mutations (red Xs), 2) adding a degron, 3) altering the strength of the TAD or DNA binding affinity of the TF, 4) changes in the number of TF binding sites or sequences, and 5) titrating 3-aminotriazole, an inhibitor of His3.

FIG. 7C depicts a schematic of yeast that provide a genetically tractable chassis for biosensor development prior to implementation in more complex eukaryotes, such as mammalian cells and plants.

DETAILED DESCRIPTION

Figure 1A:
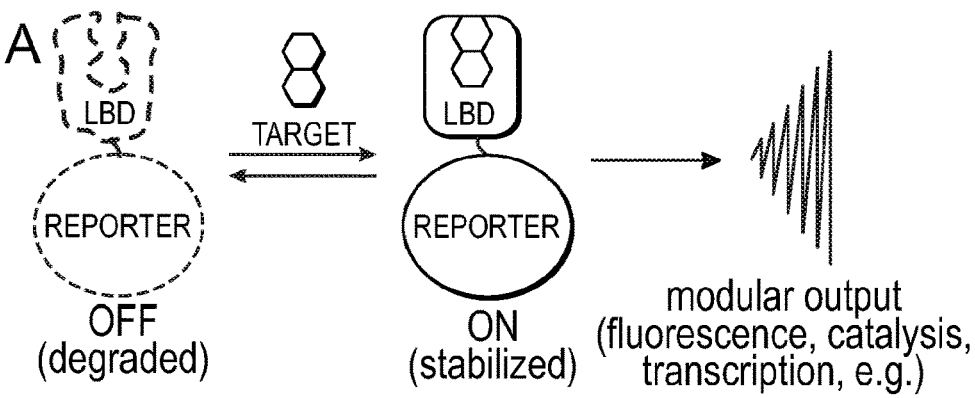
FIG. 1A depicts a general method for construction of biosensors for small molecules and is a schematic of modular biosensor construction from a conditionally destabilized LBD and a genetically fused reporter. The reporter is degraded in the absence, but not in the presence of the target small molecule.
Figure 1B:
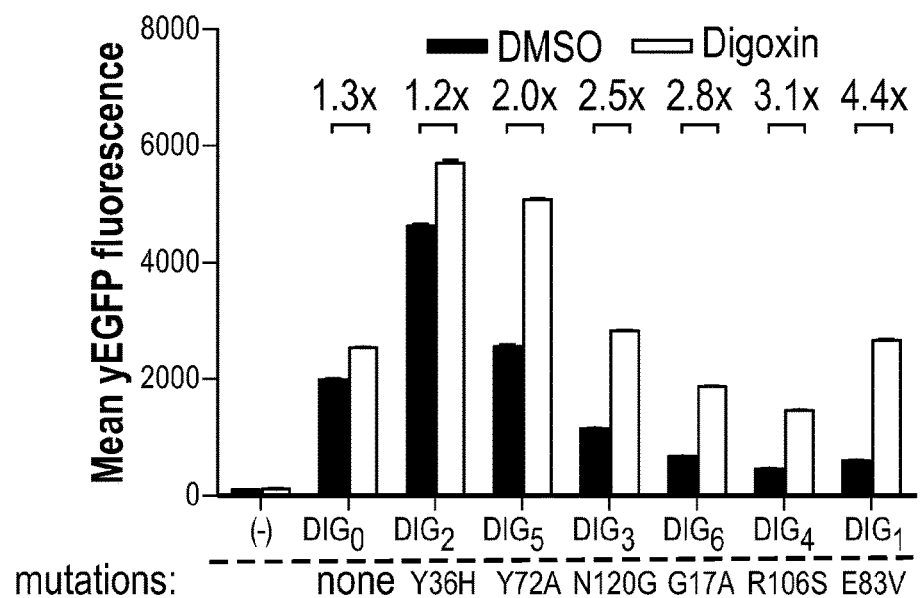
FIG. 1B graphically depicts yEGFP fluorescence of digoxin LBD-GFP biosensors upon addition of 250 µM digoxin or DMSO vehicle. Fold activation is shown above brackets, (–) indicates cells lacking biosensor constructs, and error bars represent s.e.m. of three technical replicates.
Figure 1C:
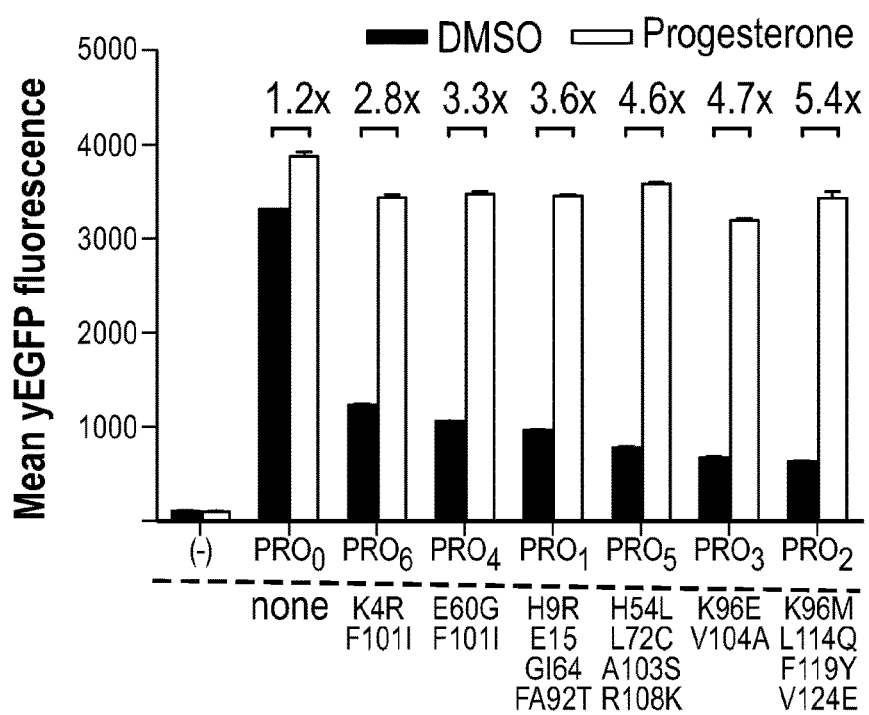
FIG. 1C graphically depicts yEGFP fluorescence of progesterone LBD-GFP biosensors upon addition of 50 µM progesterone or DMSO vehicle. Fold activation is shown above brackets, (–) indicates cells lacking biosensor constructs, and error bars represent s.e.m. of three technical replicates.
Figure 1D:
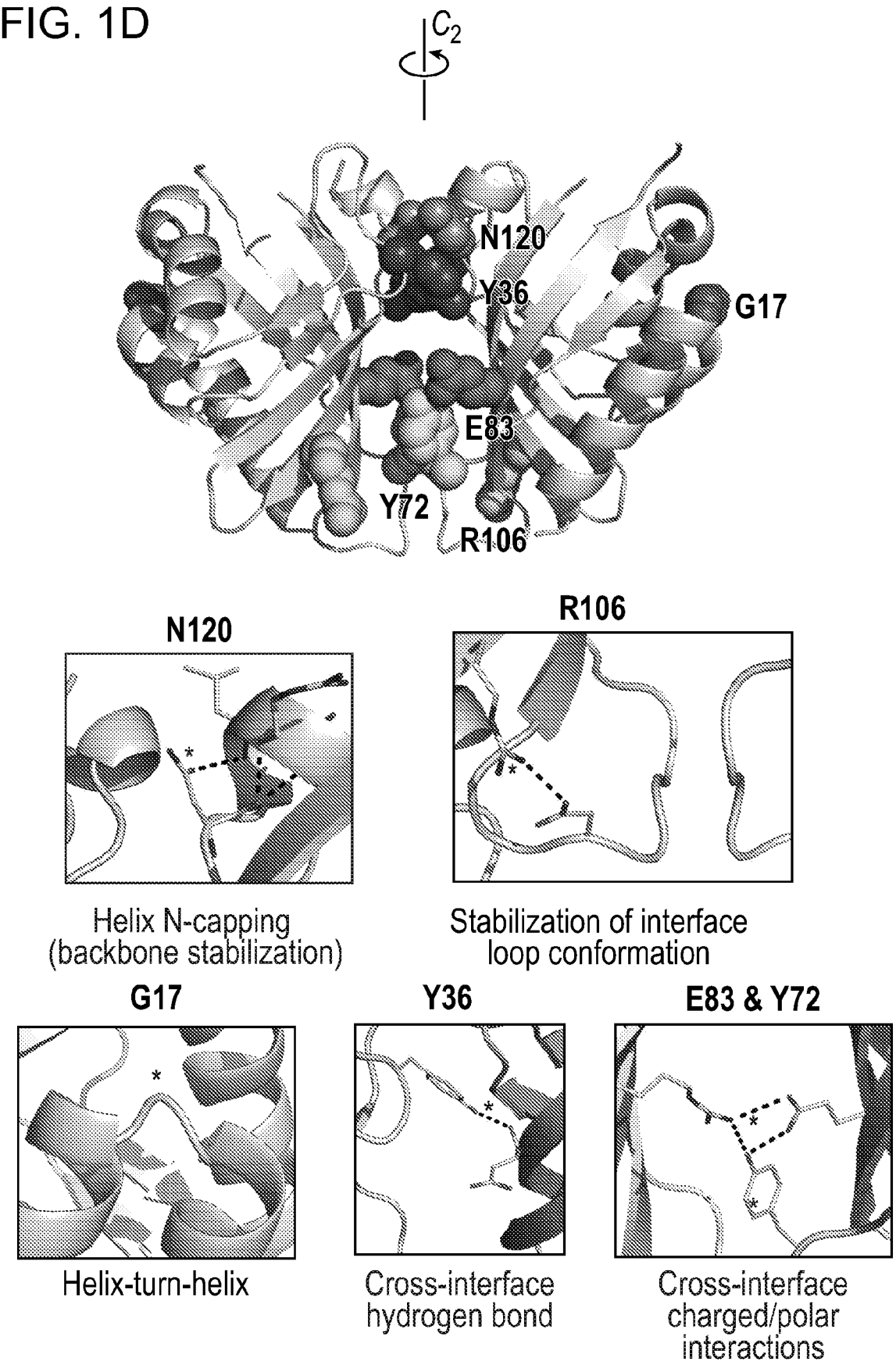
FIG. 1D illustrates the positions of conditionally destabilizing mutations of DIG0 mapped to the crystal structure of the digoxin LBD (PDB ID 4J9A). Residues are shown as colored spheres and key interactions highlighted in insets.

Embodiments of the present disclosure are directed to a biosensor including a ligand binding domain (LBD) that is fused to a reporter protein or transcription factor (TF), and wherein the biosensor retains function when ported between yeast and mammalian cells, providing ligand-dependent increased or decreased expression of the reporter protein or transcription factor compared to background, allowing for tight control of gene regulation. According to one aspect, the biosensor retains function when ported directly between yeast and mammalian cells. According to another aspect, the regulated gene activity is activated or repressed by a factor of about 50 fold or more. According to another aspect, the regulated gene activity is activated or repressed by a factor of about 100 fold or more. According to another aspect, the regulated gene activity is activated or repressed by a factor of about 250 fold or more. According to another aspect, the regulated gene activity is activated or repressed by a factor of about 500 fold or more. According to another aspect, the regulated gene activity is activated or repressed by a factor of about 1000 fold or more.

According to one aspect, the gene or genes under biosensor regulation perform CRISPR/Cas9 genome editing. According to another aspect, the biosensor further includes yeast-based biosensors which are ported directly to mammalian cells and tightly regulate CRISPR/Cas9 genome editing. According to another aspect, the biosensor eliminates unchecked Cas9 activity which can lead to off-target mutations and cytotoxicity. According to another aspect, the biosensor provides regulation of Cas9 activity whereby gene editing occurs only under pre-defined conditions. According to another aspect the biosensor further includes a construct that includes fused human codon-optimized versions of the DIG3 and PRO1 LBDs to the N-terminus of Cas9 from *S. pyogenes*.

According to one aspect, the biosensor further includes a construct wherein the construct is integrated into a reporter cell line containing an EGFP variant with a premature stop codon that renders it non-functional, which function can be restored by CRISPR/Cas9 genome editing regulated by the biosensor that performs CRISPR/Cas9 genome editing. According to another aspect, the gene or genes under regulation contain a CRISPR/Cas9 gene cassette having inactive nuclease domains that in turn performs targeted gene regulation. According to another aspect, the biosensor further includes a stable integration of the DIG-Cas9 fusion. According to another aspect, the biosensor further includes a stable integration of the PRO-Cas9 fusion. According to another aspect, the biosensor that includes a stable integration of the PPRO-Cas9 fusion further includes a stable integration of the DIG-Cas9 fusion. According to another aspect, the biosensor where the gene or genes under biosensor regulation perform CRISPR/Cas9 genome editing further includes a stable integration of the PRO-Cas9 fusion.

Embodiments of the present disclosure are directed to a method for forming biosensors including the step of directly fusing a conditionally destabilized ligand binding domain (LBD) to a reporter protein or a transcription factor (TF), to provide biosensors with increased activation or repression by their target ligands. According to one aspect, the reporter protein includes a fluorescent protein. According to another aspect, the reporter protein includes an enzyme. According to another aspect, the reporter protein includes a transcription factor (TF). According to another aspect, the biosensors retain function when ported into mammalian cells, with up to 100-fold (or more) activation or repression compared to background. According to another aspect, the biosensors provide tight control of CRISPR/Cas9 genome editing. According to another aspect, the LBDs recognize their targets with high affinity and specificity. According to another aspect, the LBD includes the computationally-designed binding domain DIG0, which binds the plant steroid glycoside digoxin and its aglycone digoxigenin with picomolar affinities. According to another aspect, the LBD includes genetic fusions of DIG3 and PRO1 to a yeast-enhanced GFP.

Embodiments of the present disclosure are directed to a method for improving the biosynthetic yield of progesterone in yeast, including the steps of fusing ligand-binding domains (LBDs) to a reporter protein or a transcription factor (TF); destabilizing the biosensor by mutation such that the fusion accumulates only in cells containing the target ligand to form a biosensor; porting the biosensor into yeast cells; mutagenizing an enzyme, enzymes, or regulatory elements that participate in the bioproduction of progesterone; screening or selecting cells by sensor output with greater or more efficient progesterone production and thereby improving the biosynthetic yield of progesterone in yeast. According to one aspect, the biosensor is ported directly into the yeast cells. According to another aspect, the reporter protein includes an enzyme. According to another aspect, the reporter protein includes a fluorescent protein.

In vivo biosensors for small molecules enable the regulation and detection of cellular responses to endogenous metabolites and exogenous chemicals. Here it is shown that LBDs can be conditionally stabilized to create biosensors that function in yeast, mammalian cells, and plants, and the use of these biosensors is demonstrated for metabolic engineering and genome editing.

By using standard diversification and screening methods, the disclosed methods include a simple platform for sensor development that can be applied to many areas of biotechnology. These sensors act either at the level of post-translational control over protein function or at the level of transcription (FIG. 7A), and they can be tuned by altering any of their components (FIG. 7B) or by modifying efflux of the target ligand in the host organism. These tunable features should make the biosensors useful in many different cellular and environmental contexts.

The results suggest a general mechanism of conditional stabilization for LBDs, allowing the rational development of biosensors for other targets. Furthermore, the portability of the mutations identified suggests a structural basis for conferring conditional stability to this LBD scaffold. Both the DIG LBD and Gal4 are homodimers and the majority of the conditionally-stabilizing mutations are located at the dimer interfaces.

Figure 1E:
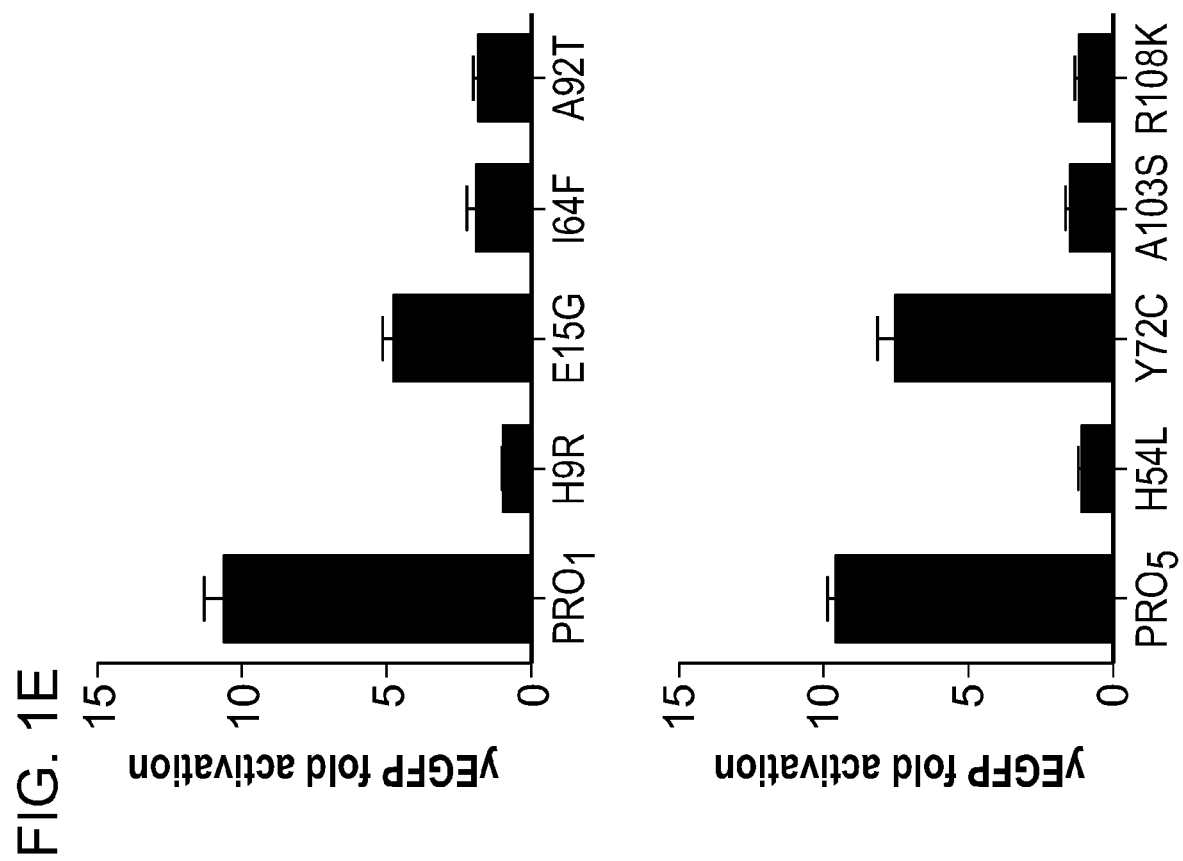
FIG. 1E graphically depicts single-mutant deconvolutions of mutations conferring progesterone sensitivity. The parental biosensor appears in the leftmost column of each panel.
Figure 1F:
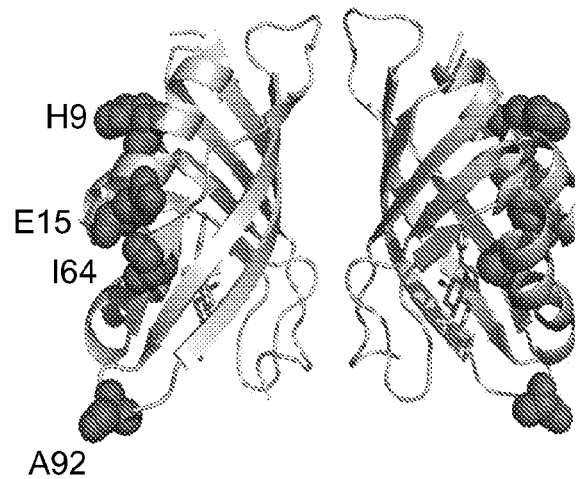
FIG. 1F-I illustrates positions of mutations in PRO1 (FIG. 1F), PRO2 (FIG. 1G), and PRO3 (FIG. 1H) are mapped to the crystal structure of the digoxin LBD (PDB ID 4J9A) and are shown in colored spheres.
Figure 1G:
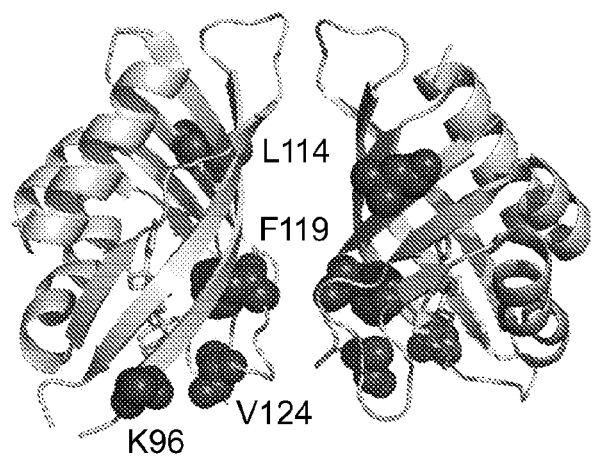
Figure 1H:
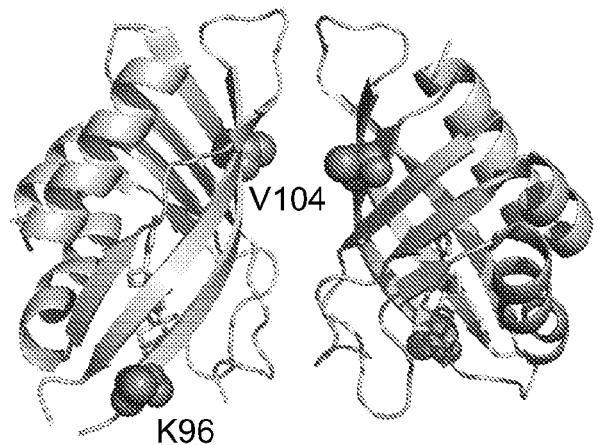
Figure 1I:
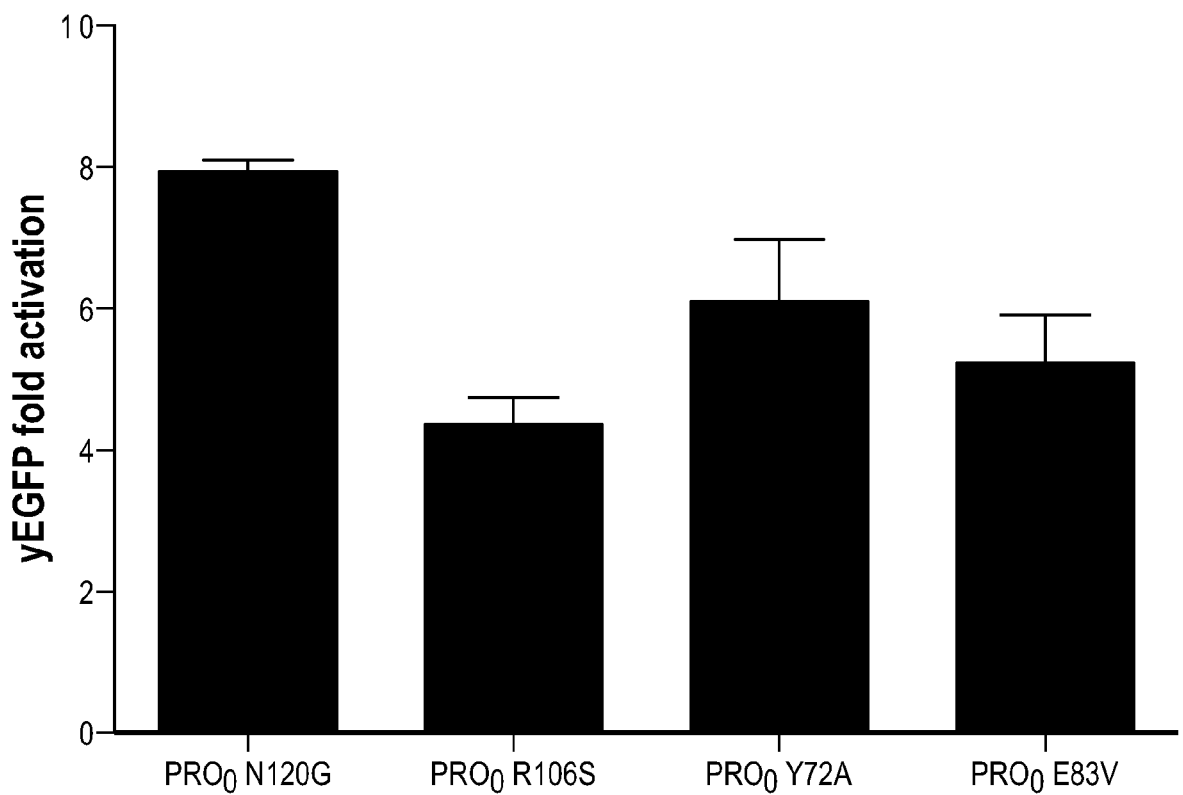
Figure 2A:
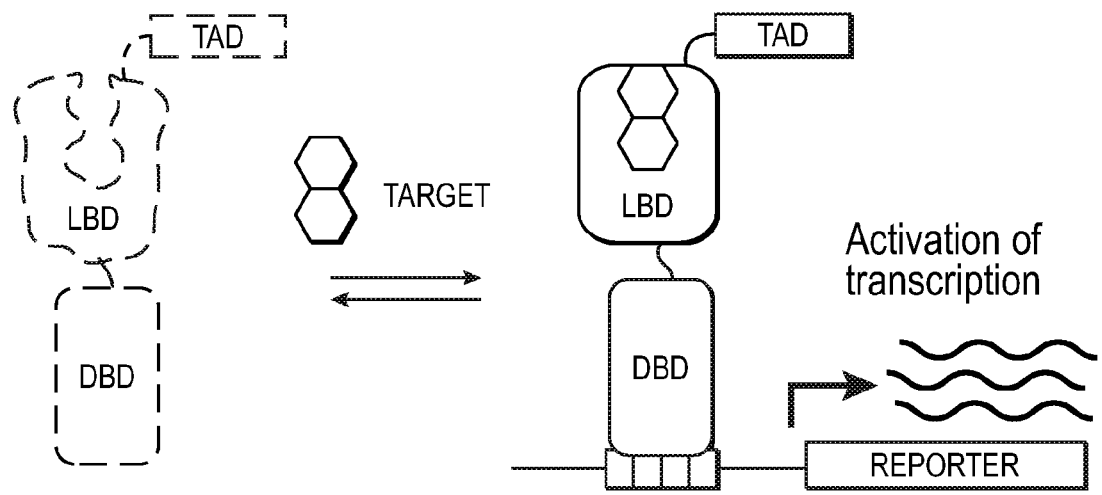
FIG. 2A is a schematic of TF-biosensor construction from a conditionally destabilized LBD, a DNA binding domain and a transactivator domain.
Figure 2B:
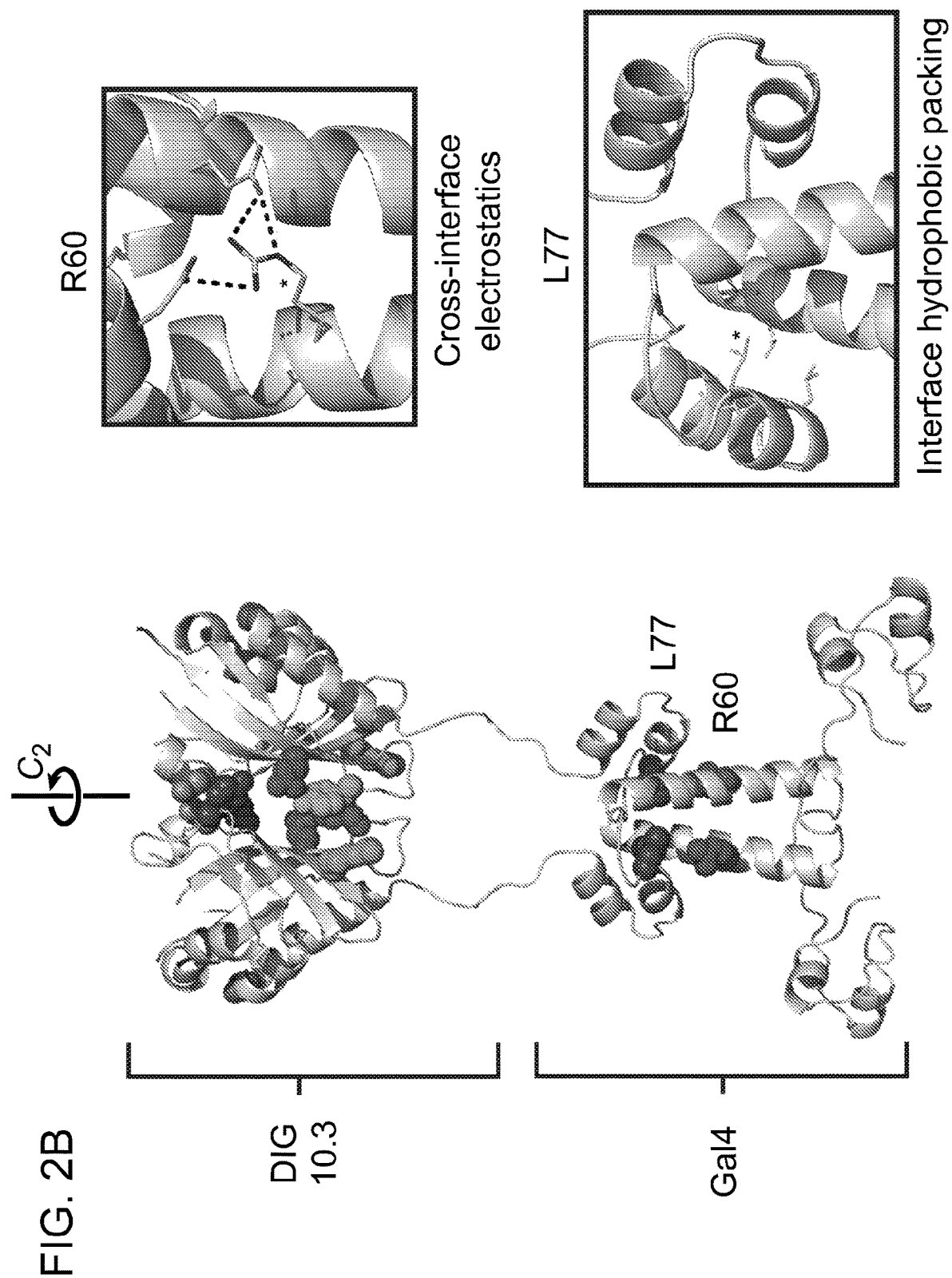
FIG. 2B illustrates the positions of conditionally destabilizing mutations of Gal4 mapped to a computational model of Gal4-DIG0 homodimer. Residues are shown as colored spheres and key interactions are highlighted in insets. The transactivator domain is not shown.
Figure 2C:
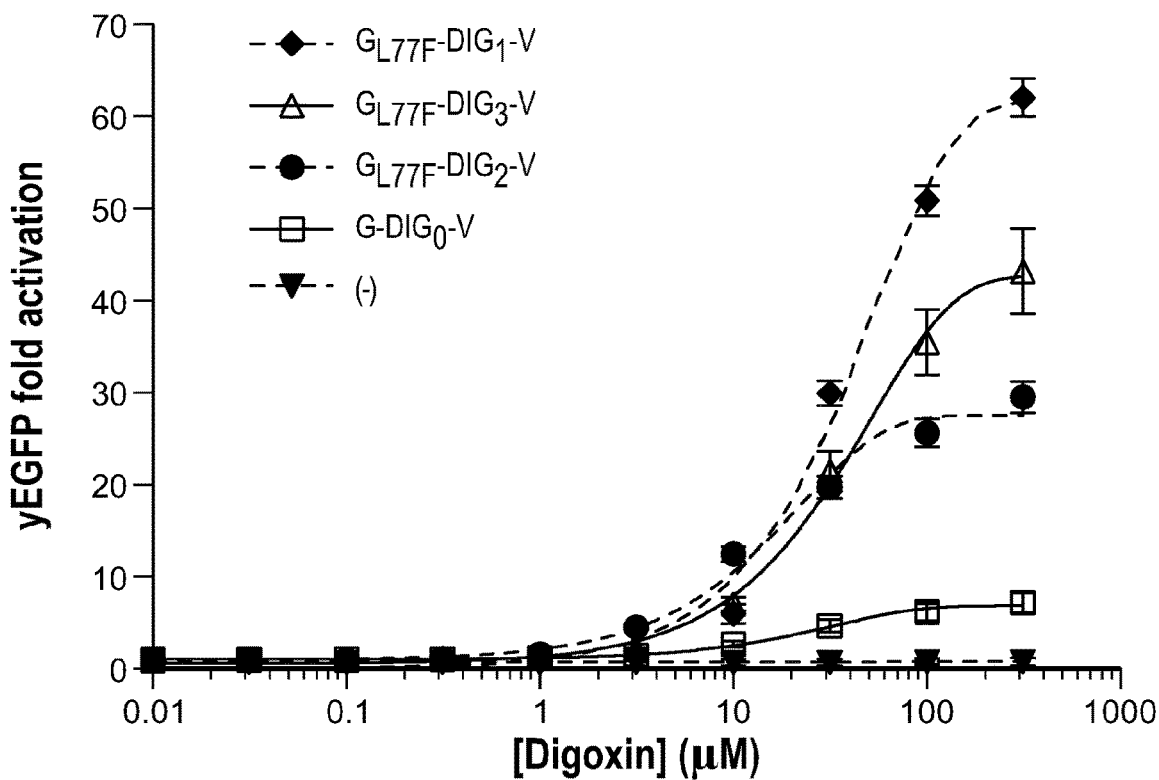
FIG. 2C graphically depicts the concentration dependence of response to digoxin for digoxin TF-biosensors driving yEGFP expression. (–) indicates cells lacking biosensor plasmids and error bars represent s.e.m. of three technical replicates.
Figure 2D:
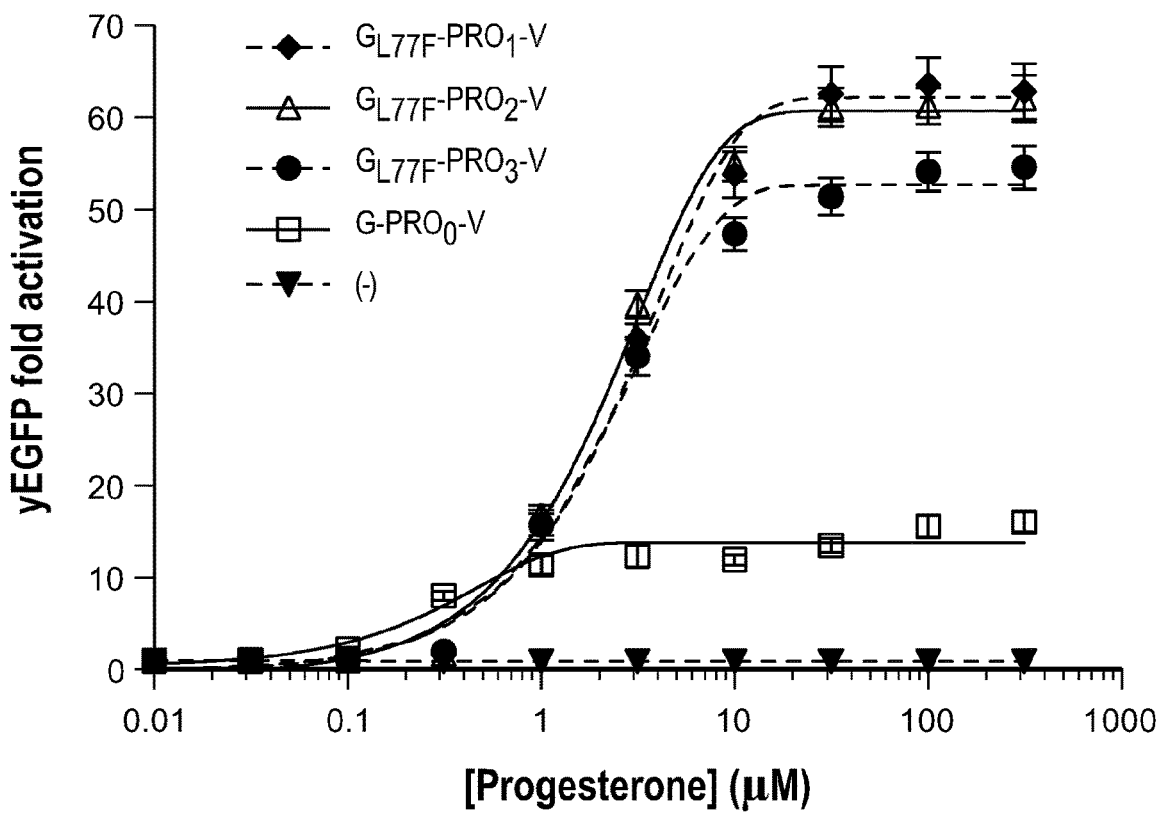
FIG. 2D graphically depicts the concentration dependence of response to progesterone for progesterone TF-biosensors driving yEGFP expression. (–) indicates cells lacking biosensor plasmids and error bars represent s.e.m. of three technical replicates.
Figure 2E:
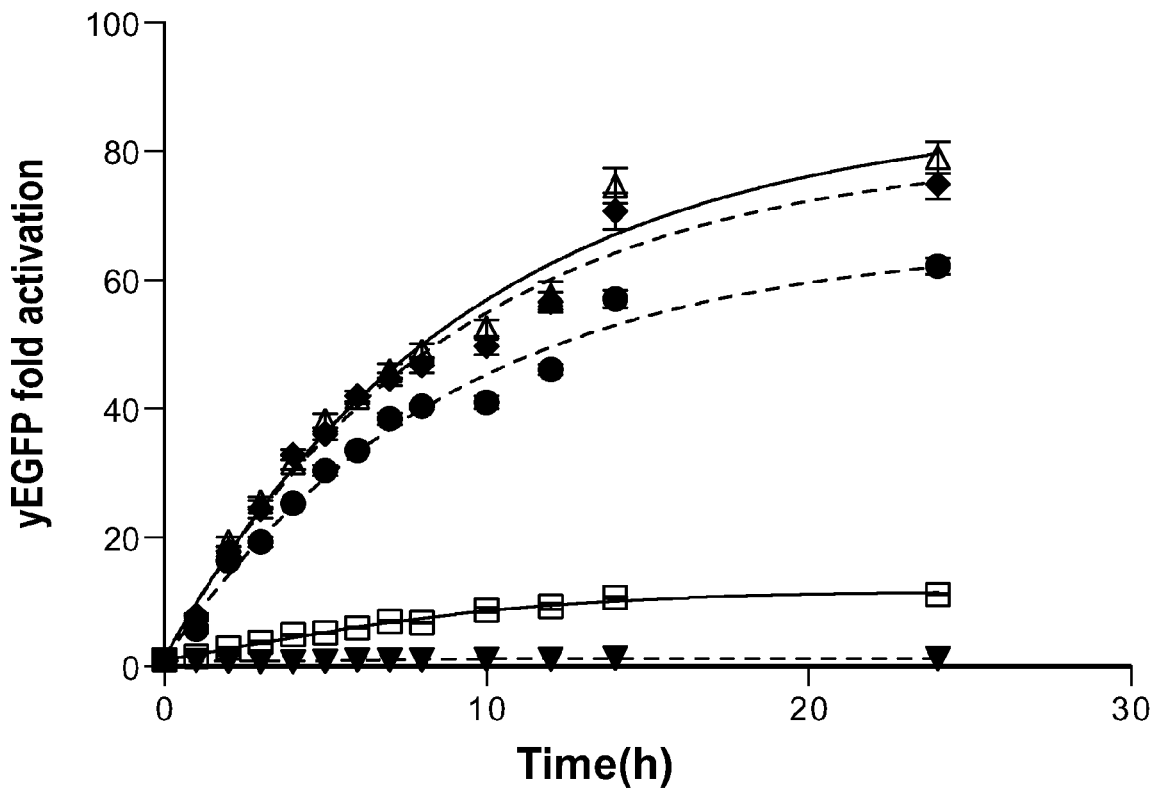
FIG. 2E graphically depicts the time dependence of response to 250 µM digoxin for digoxin TF-biosensors. Marker symbols are the same as in 2C. (–) indicates cells lacking biosensor plasmids and error bars represent s.e.m. of three technical replicates.
Figure 2F:
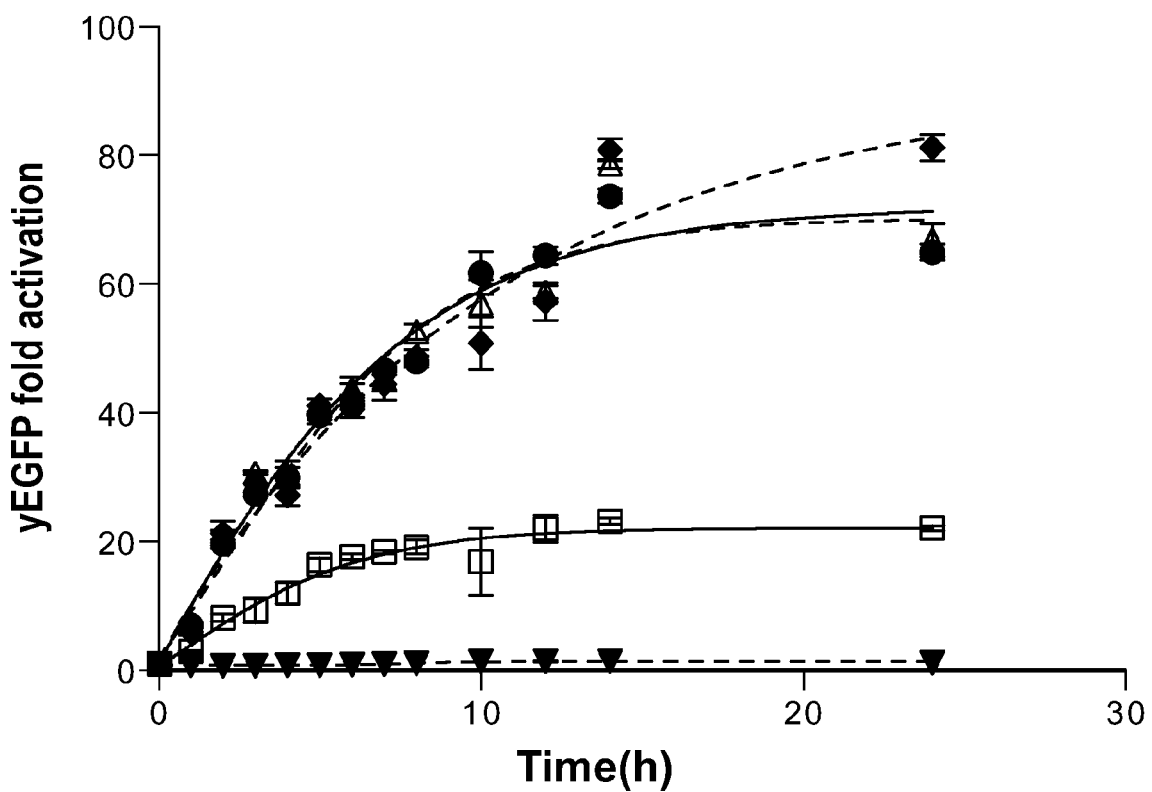
FIG. 2F graphically depicts the time dependence of response to 50 µM progesterone for progesterone TF-biosensors. Marker symbols are the same as in 2D. (–) indicates cells lacking biosensor plasmids and error bars represent s.e.m. of three technical replicates.
Figure 2H:
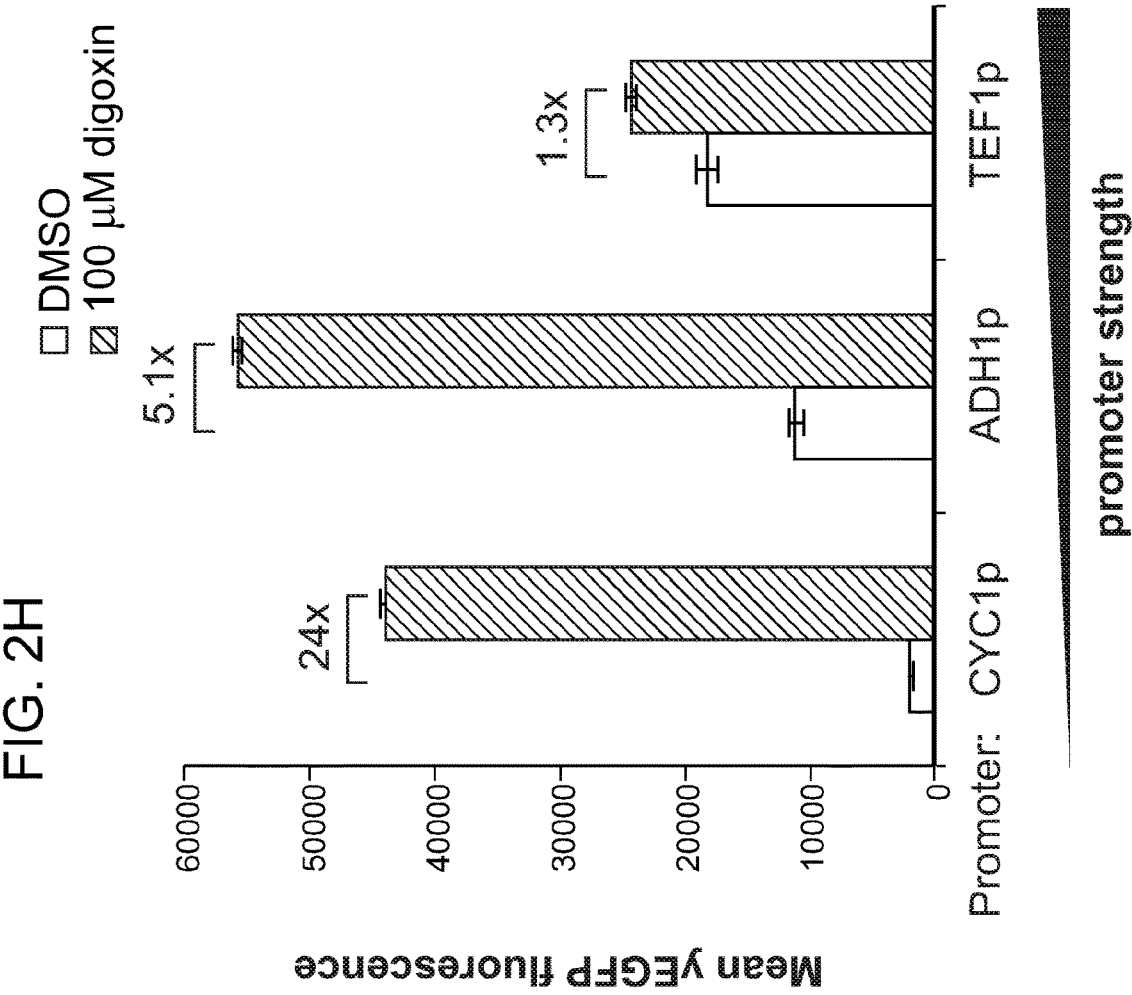
FIG. 2H graphically depicts improvements to TF-biosensor response. Digoxin-dependent expression of yEGFP by G-DIG1-V TF-biosensors containing a VP16 TAD and expressed from a CYC1, ADH1, or TEF1 promoter.
Figure 2G:
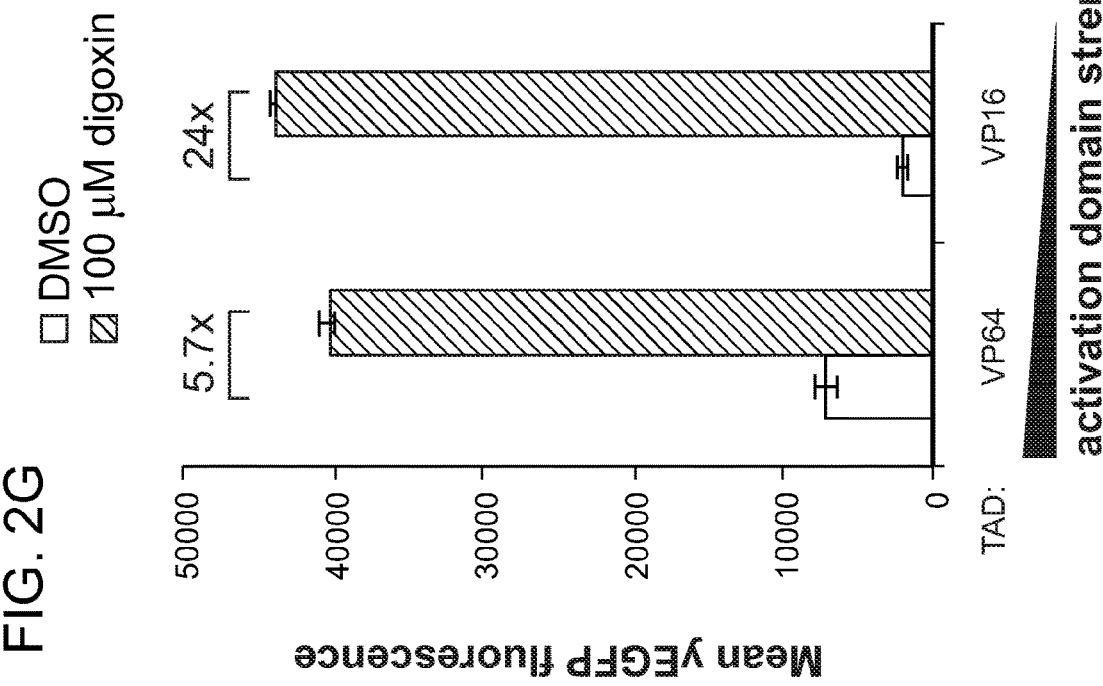
FIG. 2G graphically depicts improvements to TF-biosensor response. Digoxin-dependent expression of yEGFP by G-DIG1-V TF-biosensors containing VP64 or VP16 as the TAD and expressed from a CYC1 promoter.
Figure 2J:
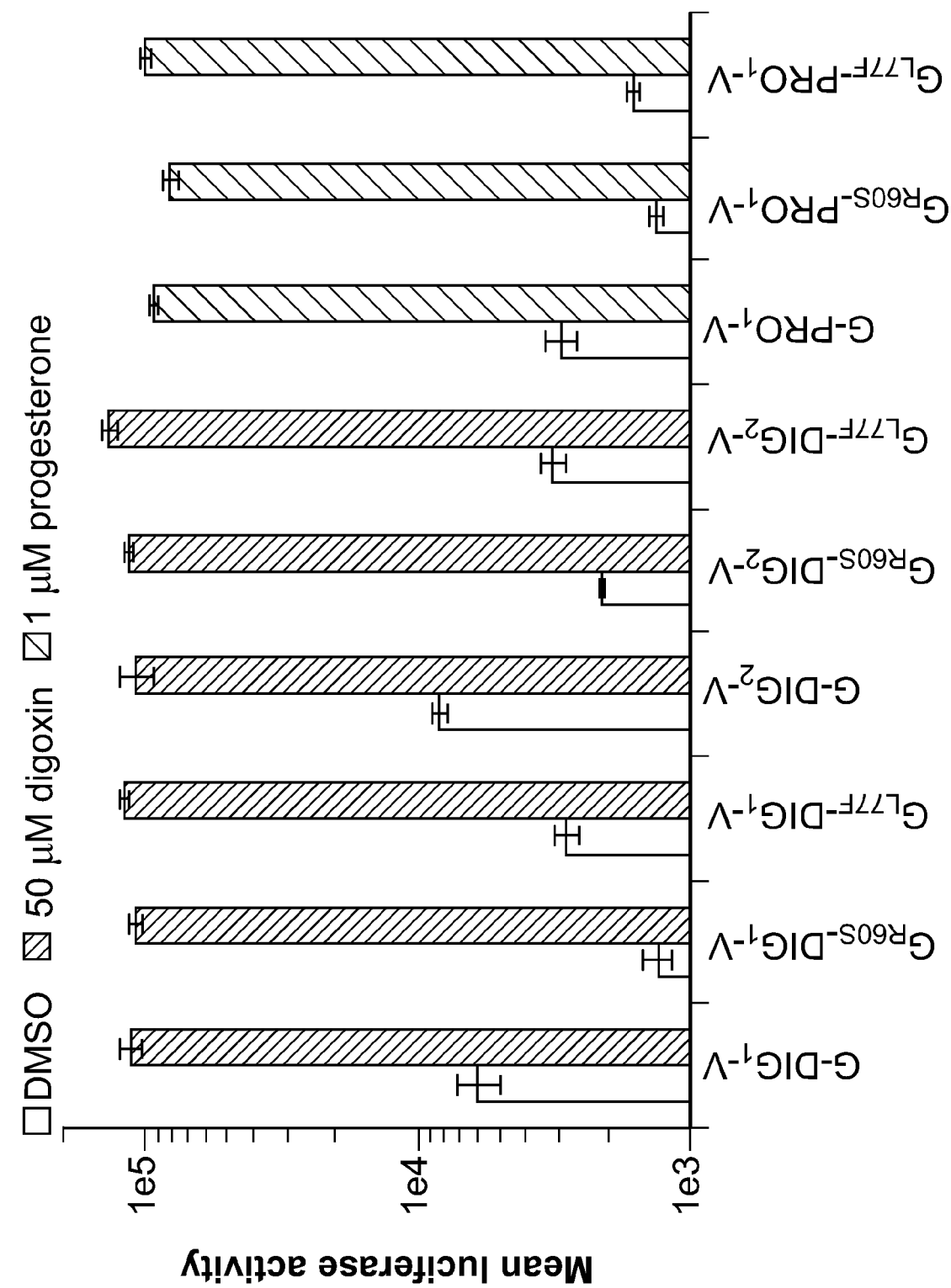
FIG. 2J depicts R60S and L77F mutations found in Gal4 were introduced into G-DIG1-V, G-DIG2-V, and G-PRO1-V. In each case, the Gal4 mutations had the effect of lowering the amount of luciferase activity in the absence of the relevant ligand.
Figure 3A:
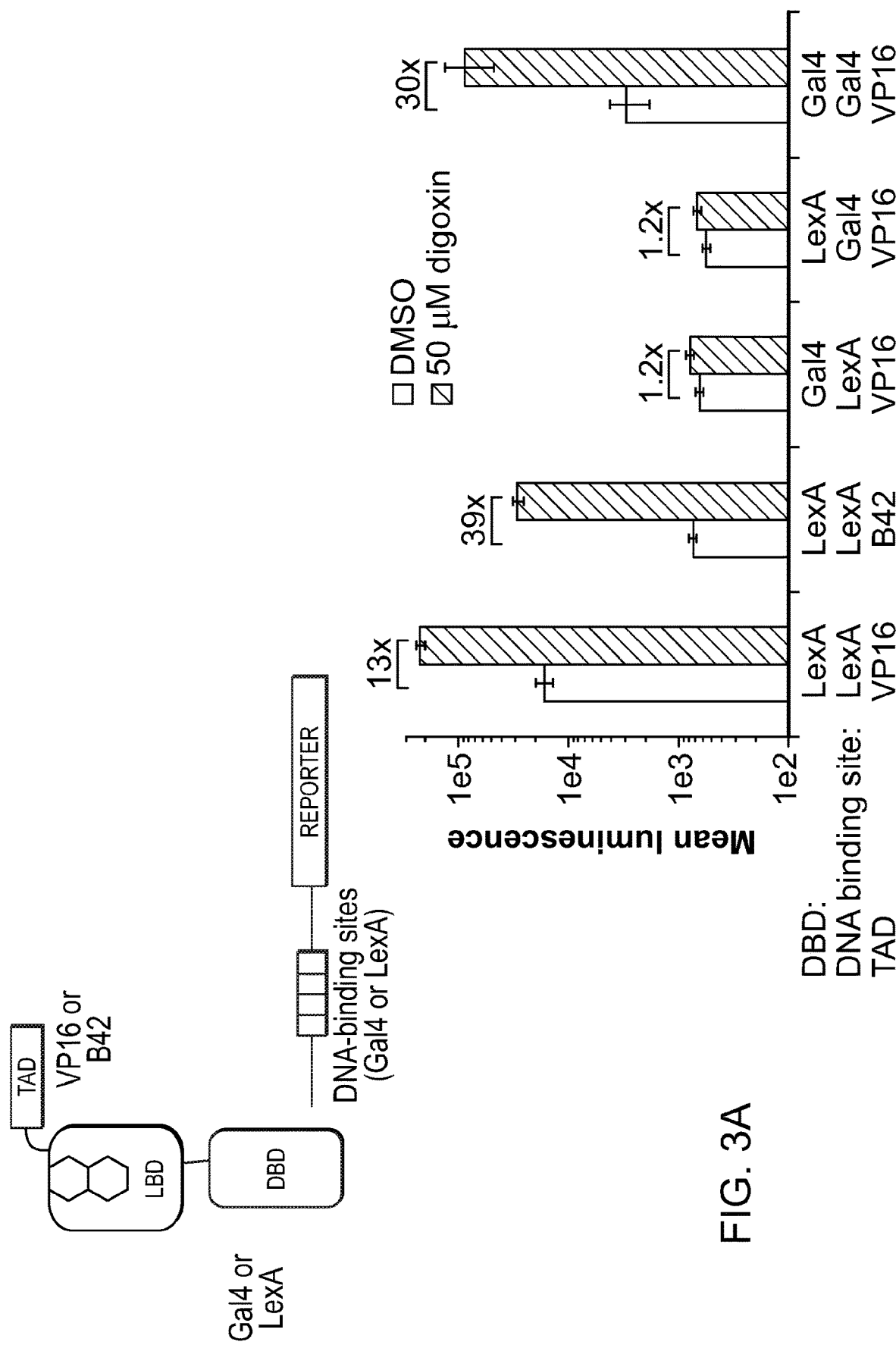
FIG. 3A illustrates the TAD and DBD of the TF-biosensor and its corresponding binding site in the reporter promoter can be swapped for a different application. Expression of a plasmid-borne luciferase reporter was driven by TF-biosensors containing either a LexA or Gal4 DBD and either a VP16 or B42 TAD. Promoters for the reporter contained DNA-binding sites for either Gal4 or LexA.
Figure 3B:
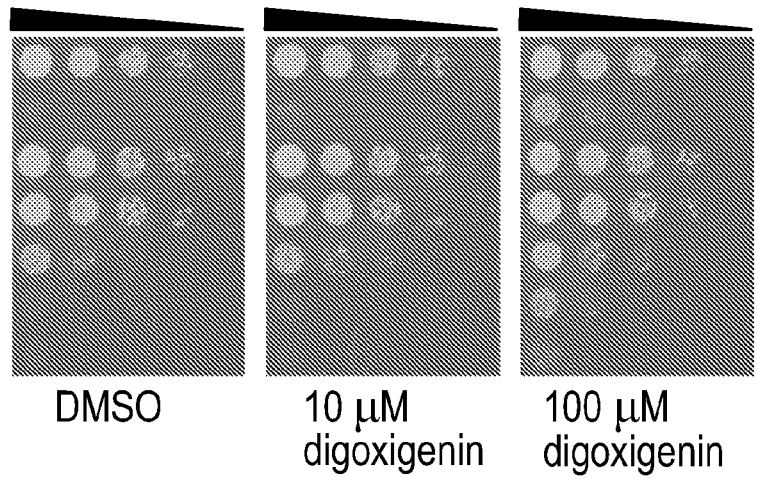
FIG. 3B includes images of TF-biosensors that were transformed into the yeast strain PJ69-4a and tested for growth on-his minimal media containing 1 mM 3-aminotriazole (3-AT) and the indicated steroid. To determine the effect of including an additional destabilization domain, the degron from Mat-alpha was cloned into one of four positions.
Figure 3C:
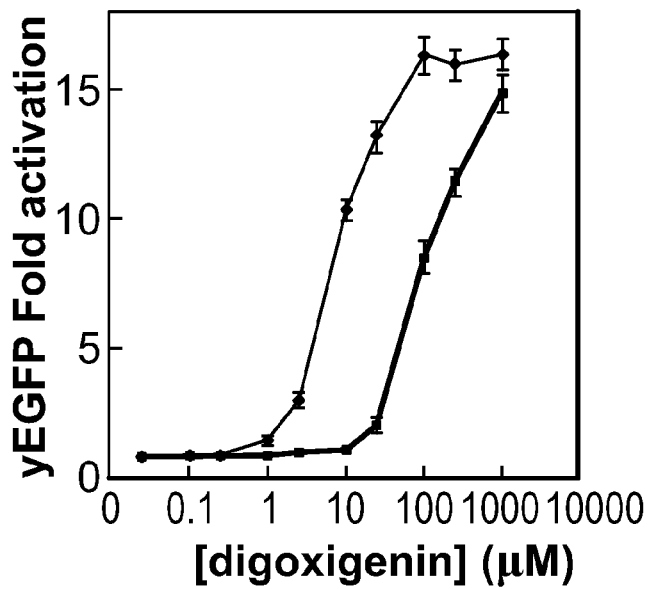
FIG. 3C graphically depicts G-DIG1-V biosensor response to digoxigenin in yEGFP reporter strain PyE1 either with or without a deletion to the ORF of PDR5.
Figure 3D:
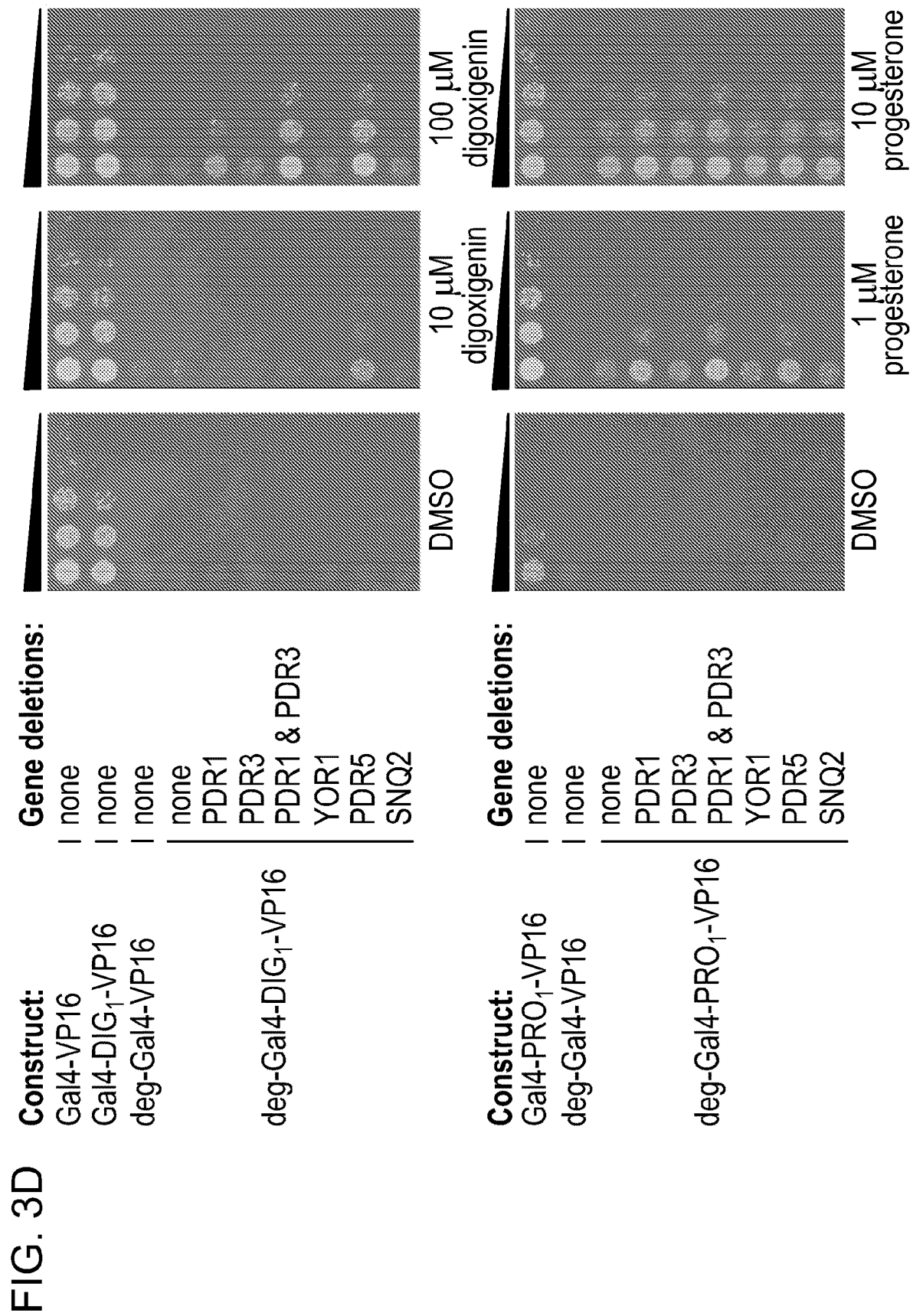
FIG. 3D includes images of ligand and TF-biosensor dependent growth on -his media in yeast strains containing deleted ORFs for efflux related transcription factors (PDR1 and PDR3) or ABC transporter proteins (YOR1, PDR5, SNQ2).
Figure 4A:
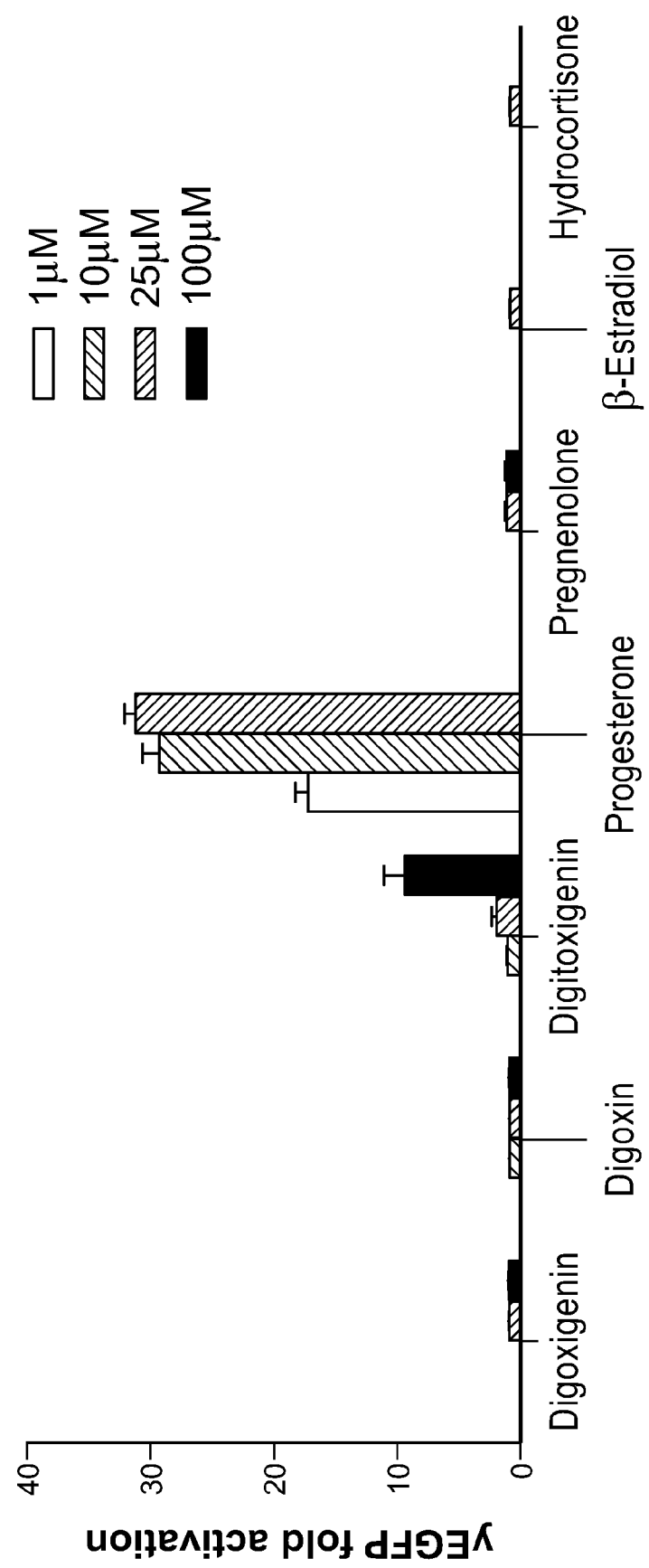
FIGS. 4A-4K depict the application of biosensors to metabolic engineering in yeast.
Figure 4B:
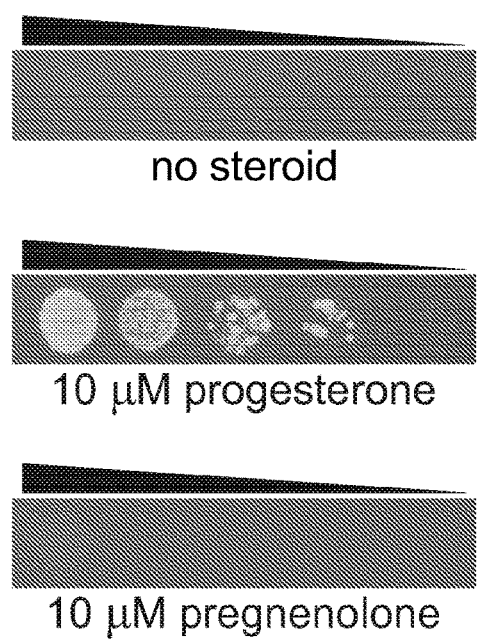
Figure 4C:
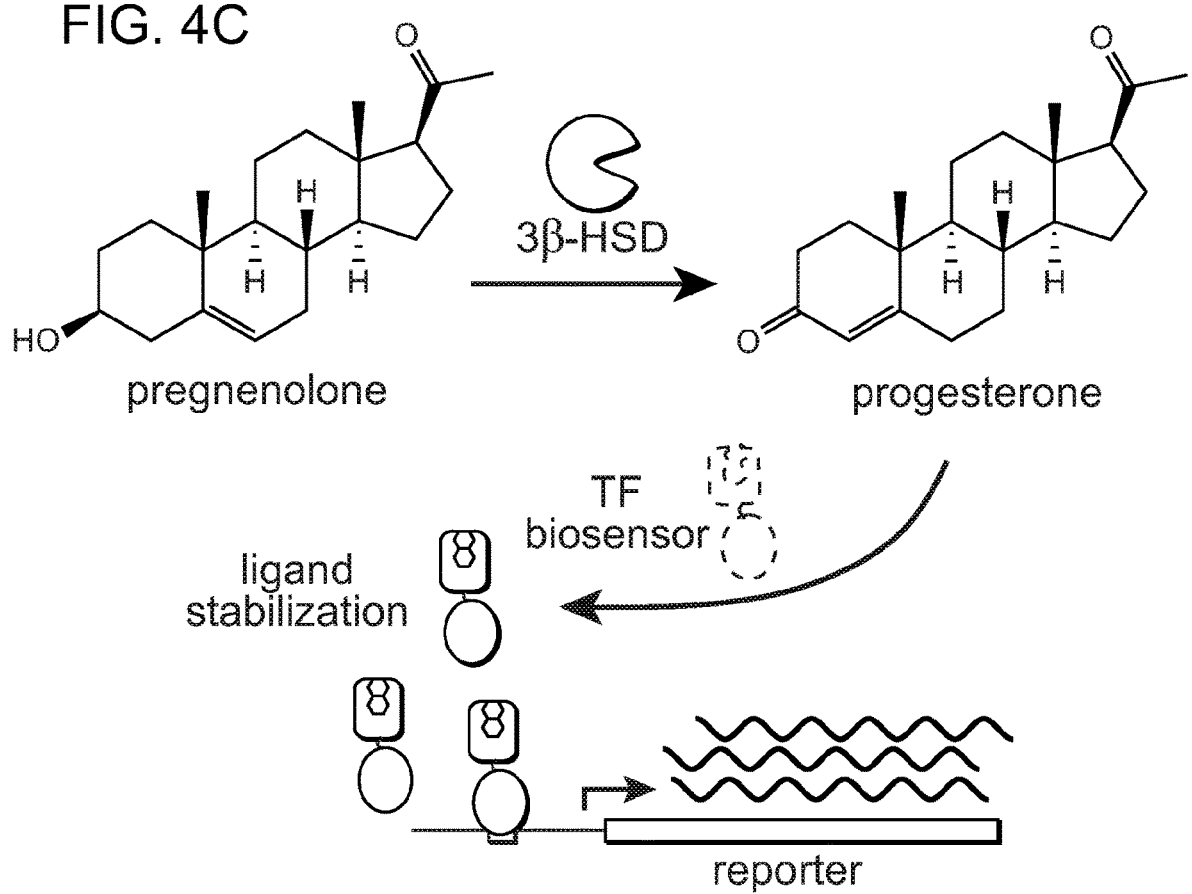
Figure 4D:
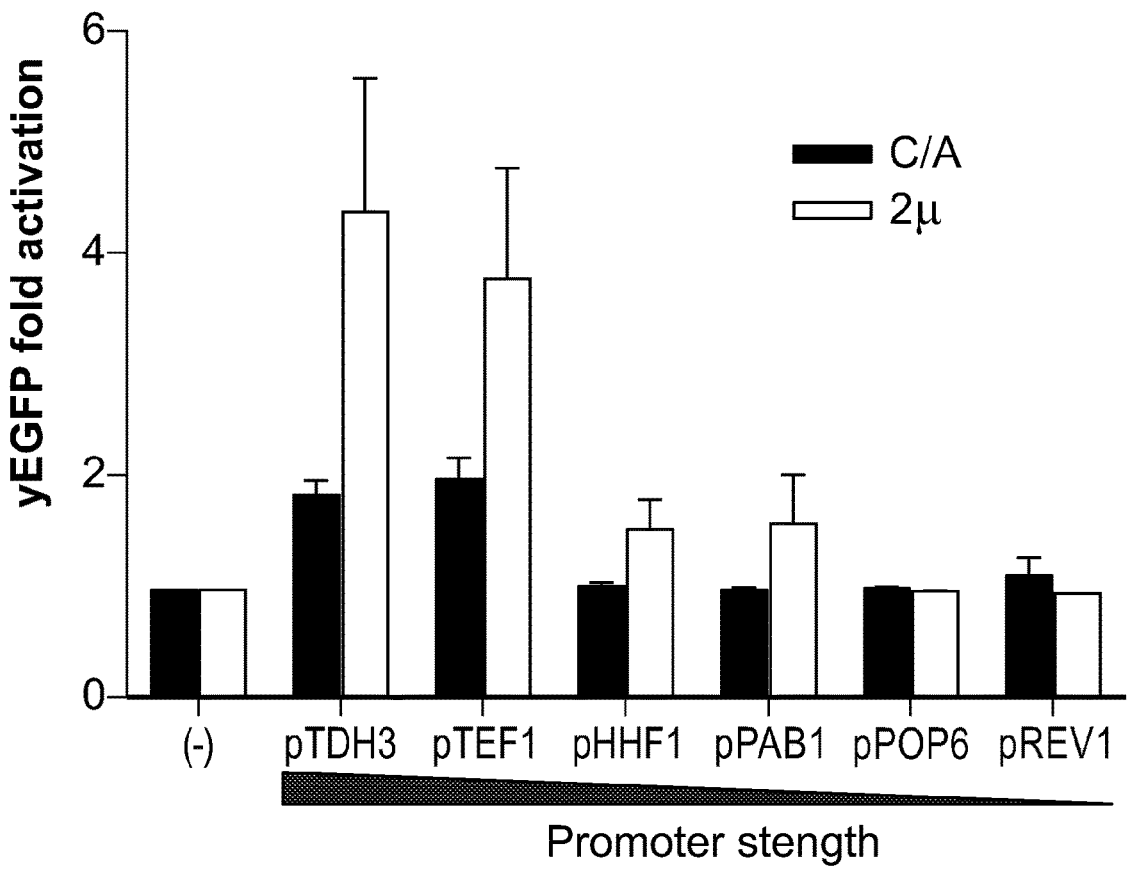
Figure 4E:
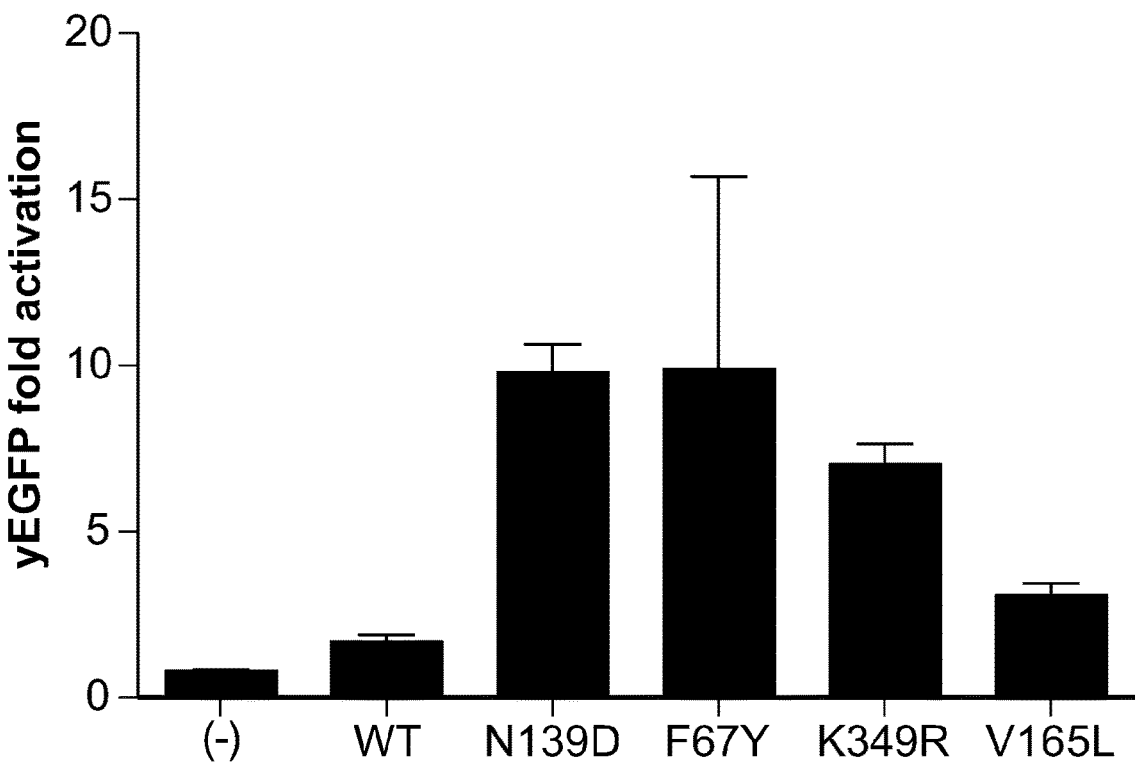
Figure 4F:
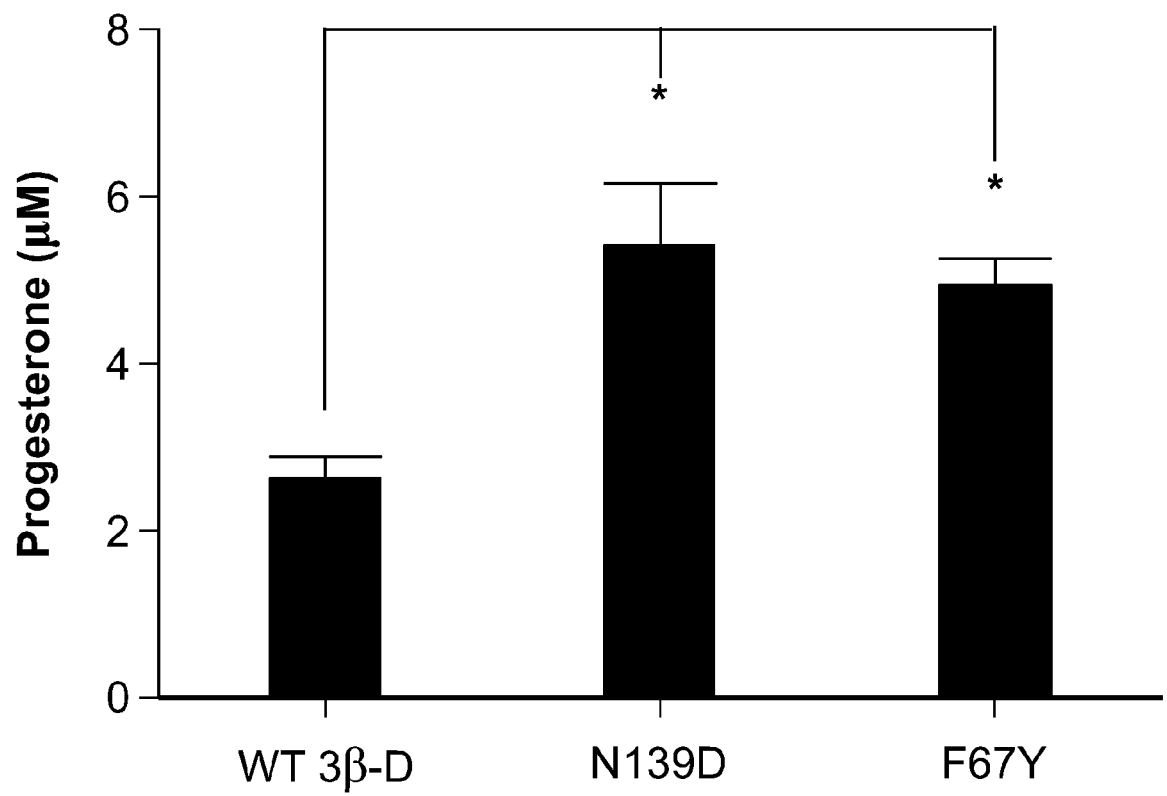
Figure 4G:
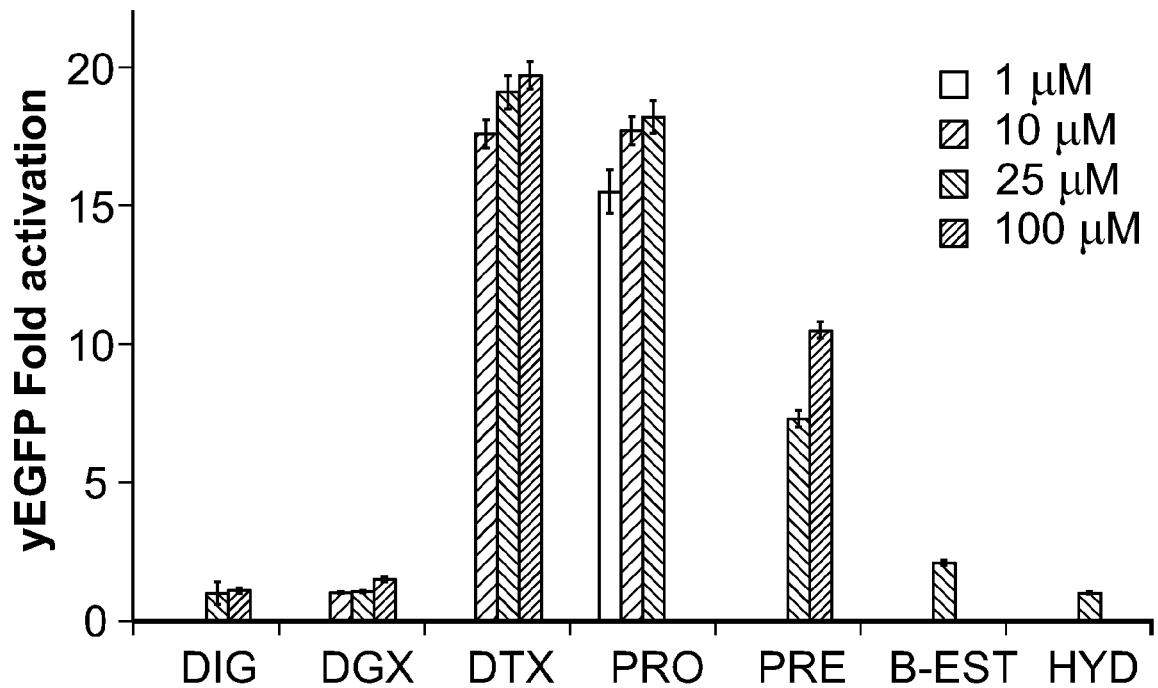
Figure 4H:
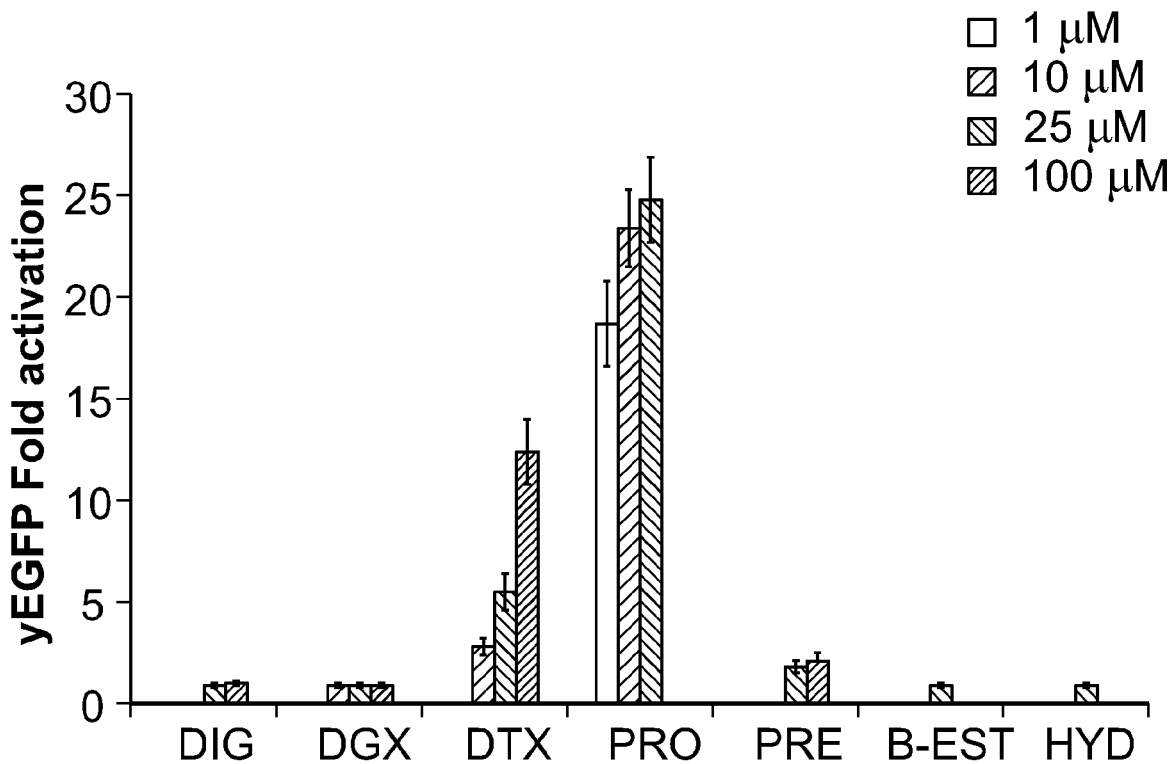
Figure 4I:
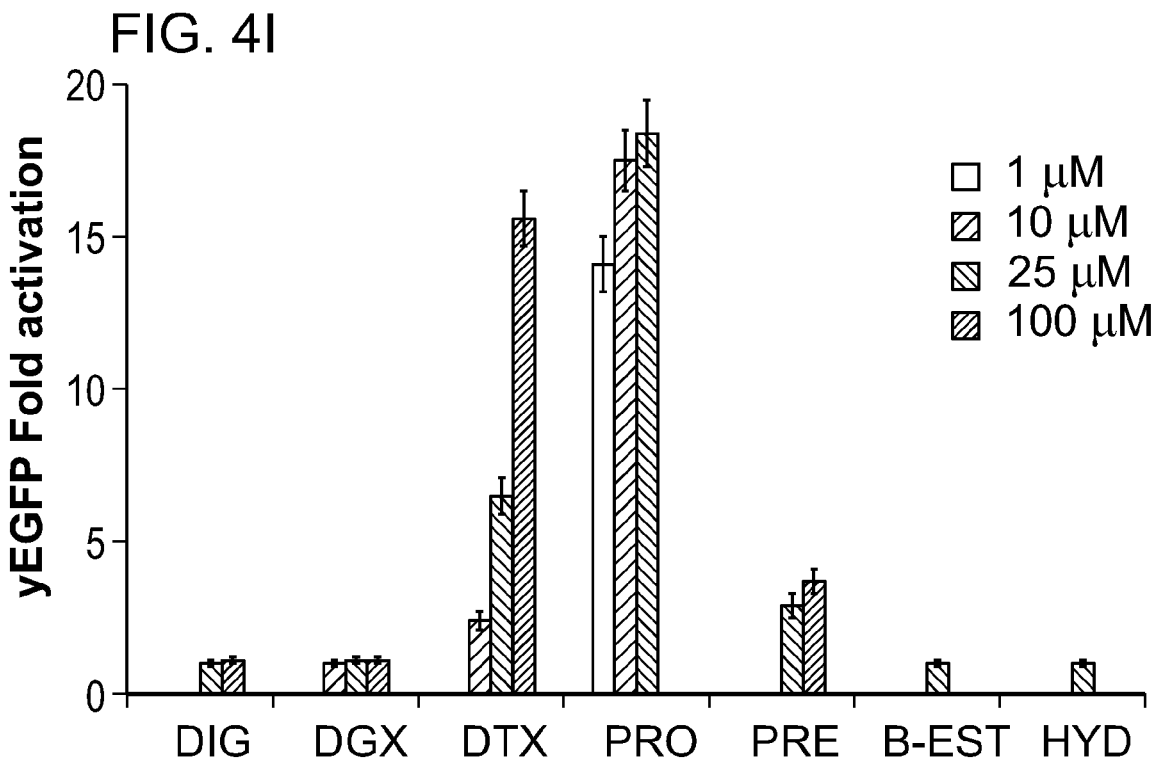
Figure 4J:
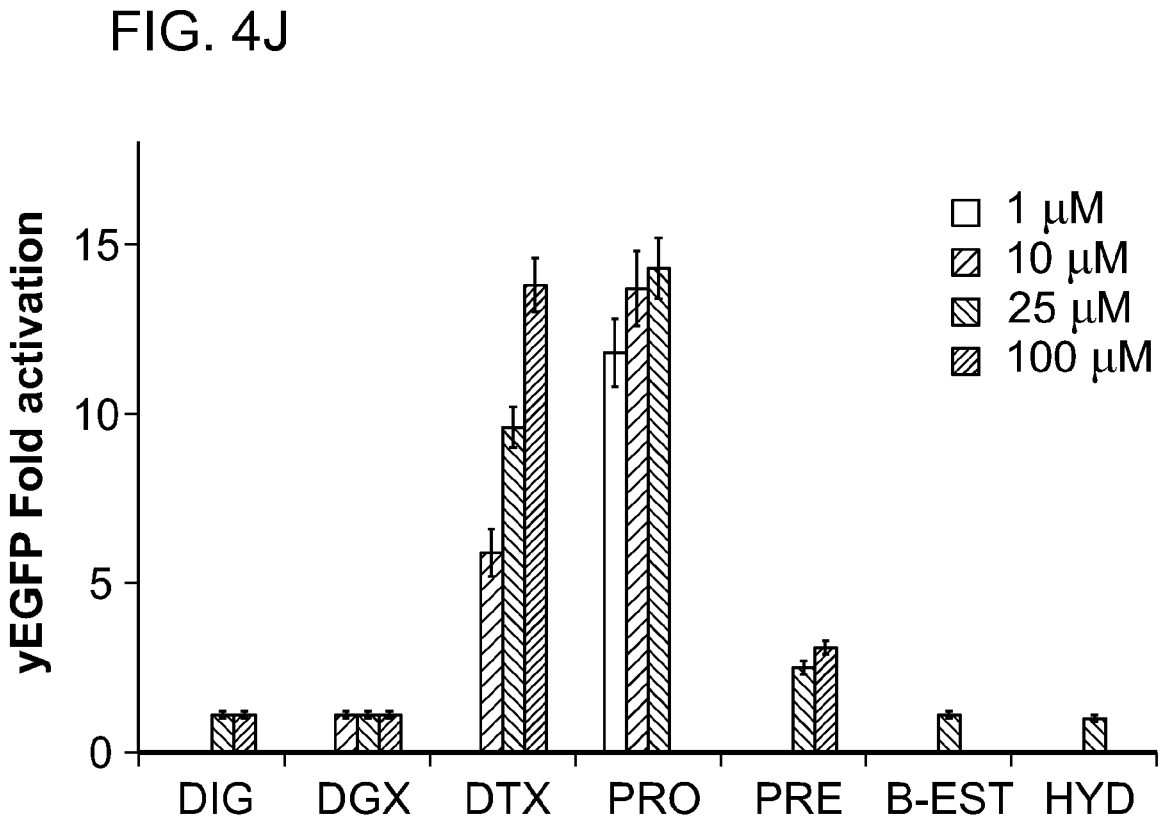
Figure 4K:
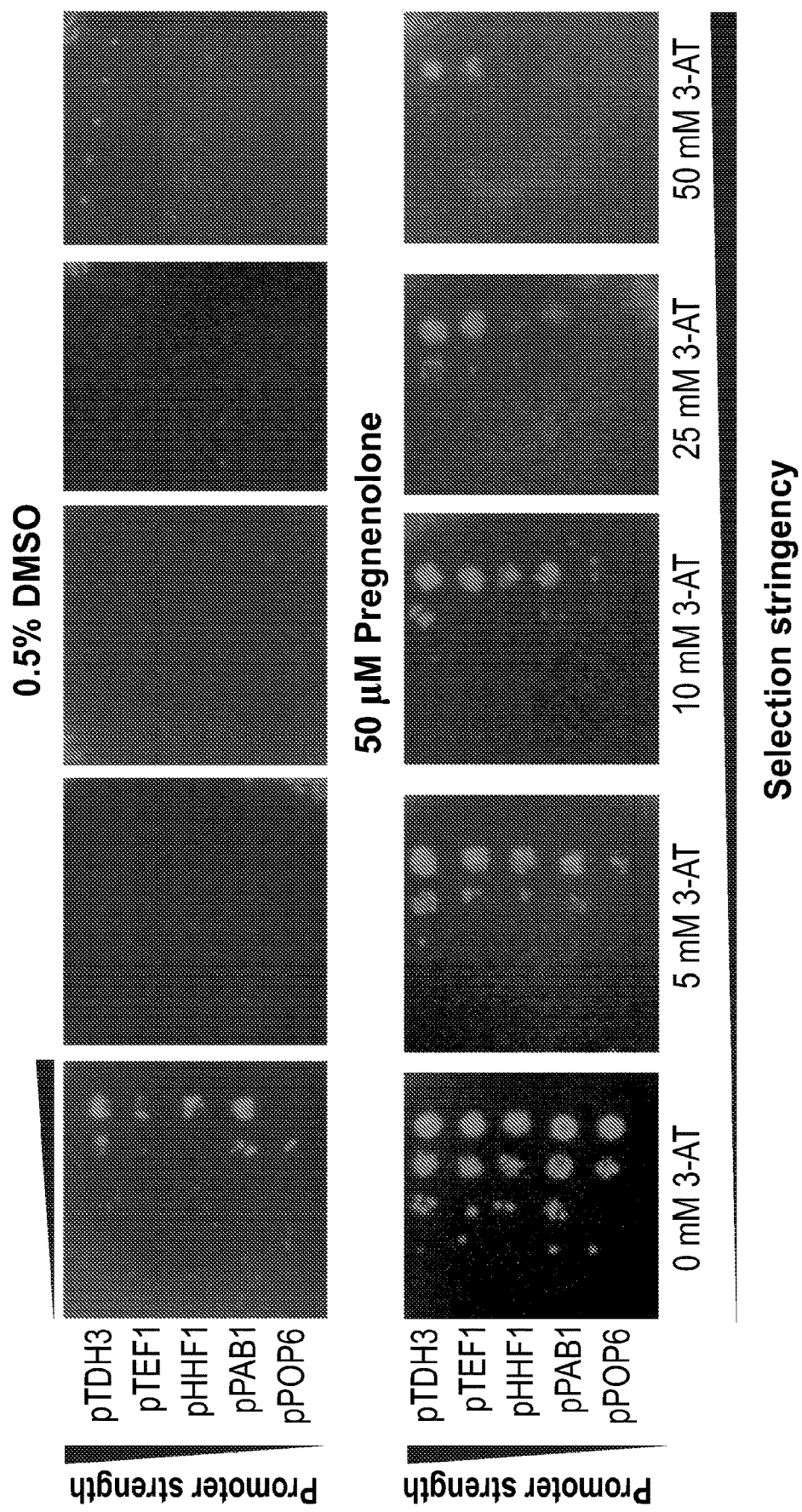

A computational model of the Gal4-DIG0 complex indicates that the orientation of the two domains allows a homodimeric fusion to form (FIG. 2B). These results suggest an allosteric interplay between ligand binding and dimer formation: weakening of the dimer interface, in either the DIG0 or the Gal4 domain, is compensated by ligand binding. This LBD scaffold is derived from a member of the nuclear transport factor 2 family, a fold class that typically has a large dimer interface (~1200 Å2) that facilitates the large and open ligand-binding site (~600 A2). These protein folds are well suited for de novo design of other LBDs (unpublished results) because of their large binding pocket and natural substrate diversity, Todd, A. E., Orengo, C. A. & Thornton, J. M. Sequence and structural differences between enzyme and nonenzyme homologs. Structure 10, 1435-1451 (2002). Exploiting dimer interfaces to modulate stability without impairing ligand binding may be a general mechanism to confer conditional stability on LBDs. This possibility is supported by the observation that interface mutations in DIG0 and Gal4 conferring digoxigenin-dependent stability lead to progesterone-dependent stability in a progesterone biosensor (FIG. 1E).

A longstanding challenge in metabolic engineering is to rapidly detect and control how changes to the regulation and composition of biosynthetic pathways affect product titers. Transcriptional control by a product or intermediate, Zhang, F., Carothers, J. M. & Keasling, J. D., Design of a dynamic sensor-regulator system for production of chemicals and fuels derived from fatty acids. Nat. Biotechnol., 30, 354-9 (2012); Raman, S., Rogers, J. K., Taylor, N. D. & Church, G. M., Evolution-guided optimization of biosynthetic pathways. Proc. Natl. Acad. Sci., 201409523 (2014). doi: 10.1073/pnas.1409523111; Tang, S.-Y. & Cirino, P. C. Design and application of a mevalonate-responsive regulatory protein. Angew. Chem. Int. Ed. Engl., 50, 1084-6 (2011), and directed evolution of constituent pathway elements, Agresti, J. J. et al., Ultrahigh-throughput screening in drop-based microfluidics for directed evolution. Proc. Natl. Acad. Sci. U.S.A. 107, 4004-9 (2010); Alper, H., Miyaoku, K. & Stephanopoulos, G. Construction of lycopene-overproducing *E. coli* strains by combining systematic and combinatorial gene knockout targets. Nat. Biotechnol. 23, 612-6 (2005); Dietrich, J. a., Shis, D. L., Alikhani, A & Keasling, J. D. Transcription Factor-Based Screens and Synthetic Selections for Microbial Small-Molecule Biosynthesis. ACS Synth. Biol. 2, 47-58 (2013), have emerged as promising strategies towards this goal. These approaches require high selectivity against intermediates, Zhang, F. & Keasling, J. Biosensors and their applications in microbial metabolic engineering. Trends Microbiol. 19, 323-9 (2011), a feature demonstrated here that can be explicitly considered during the computational design and screening process.

The disclosed method allows biosensors to be generated that are highly selective for a small molecule, facilitating a simple directed evolution strategy without requiring prior structural or bioinformatic knowledge about the targeted enzyme(s) or pathway(s). Because the biosensors are TF-based, sophisticated systems of optimizing metabolic output, such as dynamic control of gene expression, Zhang, F., Carothers, J. M. & Keasling, J. D., Design of a dynamic sensor-regulator system for production of chemicals and fuels derived from fatty acids. Nat. Biotechnol., 30, 354-9 (2012), and feedback regulated genome evolution, Chou, H. H. & Keasling, J. D. Programming adaptive control to evolve increased metabolite production. Nat. Commun. 4, 2595 (2013), are possible.

Modular small molecule biosensors enable diverse cellular responses to a variety of exogenous and endogenous signals, Banaszynski, L. A, Sellmyer, M. A., Contag, C. H., Wandless, T. J. & Thorne, S. H. Chemical control of protein stability and function in living mice. Nat. Med. 14, 1123-1127 (2008). Gene editing is an area that requires particularly tight coupling of cell response to activation signals. The CRISPR/Cas9 system provides a facile and robust genome editing platform, but it can result in off-target genetic changes. See Fu, Y. et al., High-frequency off-target mutagenesis induced by CRISPR-Cas nucleases in human cells. Nat. Biotechnol. 31, 822-6 (2013); Mali, P. et al., CAS9 transcriptional activators for target specificity screening and paired nickases for cooperative genome engineering. Nat. Biotechnol. 31, 833-8 (2013); Pattanayak, V. et al., High-throughput profiling of off-target DNA cleavage reveals RNA programmed Cas9 nuclease specificity. Nat. Biotechnol. 31, 839-43 (2013). Proposed solutions include optimizing guide RNA sequences, Fu, Y., Sander, J. D., Reyon, D., Cascio, V. M. & Joung, J. K. Improving CRISPR-Cas nuclease specificity using truncated guide RNAs. Nat. Biotechnol. 32, 279-84 (2014); Cho, S. W. et al., Analysis of off-target effects of CRISPR Cas-derived RNA-guided endonucleases and nickases sup2. Genome Res. 24, 132-141 (2014), building chimeric Cas9 fusions requiring the presence of two Cas9 molecules in close proximity, Mali, P. et al., CAS9 transcriptional activators for target specificity screening and paired nickases for cooperative genome engineering. Nat. Biotechnol. 31, 833-8 (2013); Tsai, S. Q. et al., Dimeric CRISPR RNA-guided FokI nucleases for highly specific genome editing. Nat. Biotechnol. 32, 569-76 (2014); Guilinger, J. P., Thompson, D. B. & Liu, D. R. Fusion of catalytically inactive Cas9 to FokI nuclease improves the specificity of genome modification. Nat. Biotechnol. 32, 577-82 (2014); Ran, F. A. et al., Double nicking by RNA-guided CRISPR cas9 for enhanced genome editing specificity. Cell 154, 1380-1389 (2013), and regulating Cas9 activity by chemical or light-based inducers, see Dow, L. E. et al., Inducible in vivo genome editing with CRISPR-Cas9. Nat. Biotechnol. 33, (2015); Zetsche, B., Volz, S. E. S. & Zhang, F. A split-Cas9 architecture for inducible Genome editing and transcription modulation. Nat. Biotechnol. 33, 139-142 (2015); Polstein, L. R. & Gersbach, C. a. A light-inducible CRISPR-Cas9 system for control of endogenous gene activation. Nat. Chem. Biol. 11, (2015). While small molecule inducers including doxycycline and rapamycin have been used, these molecules may confer leaky expression and cytotoxicity, Xie, J., Nair, A. & Hermiston, T. W. A comparative study examining the cytotoxicity of inducible gene expression system ligands in different cell types. Toxicol. Vitr. 22, 261-266 (2008). Thus, an expanded chemical repertoire is needed for tightly regulated gene editing and gene therapy applications.

Figure 5A:
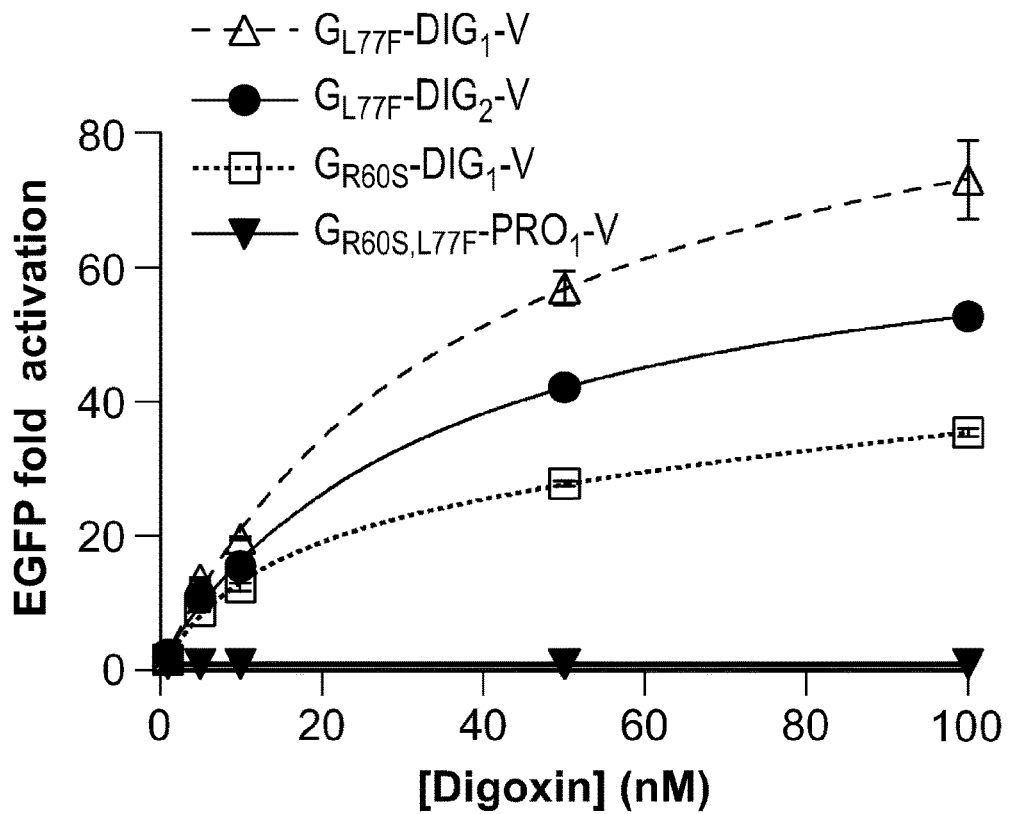
FIGS. 5A-5E depict the activation of biosensors in mammalian cells and regulation of CRISPR/Cas9 activity.
Figure 5B:
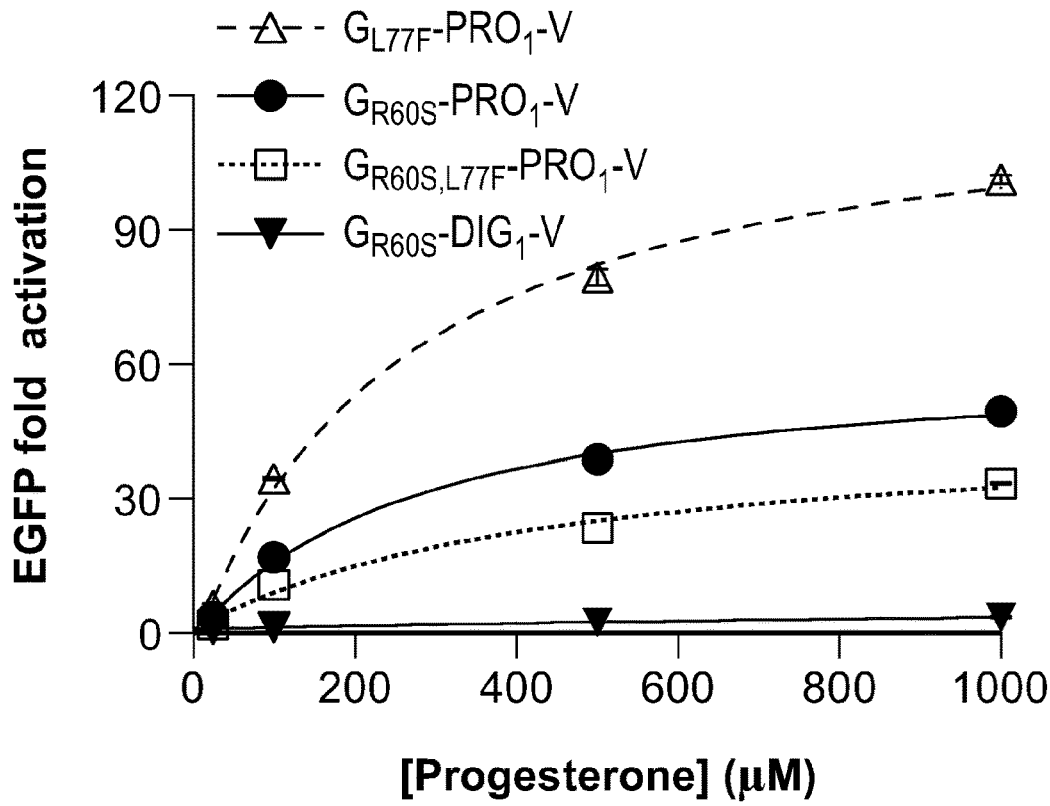
Figure 5C:
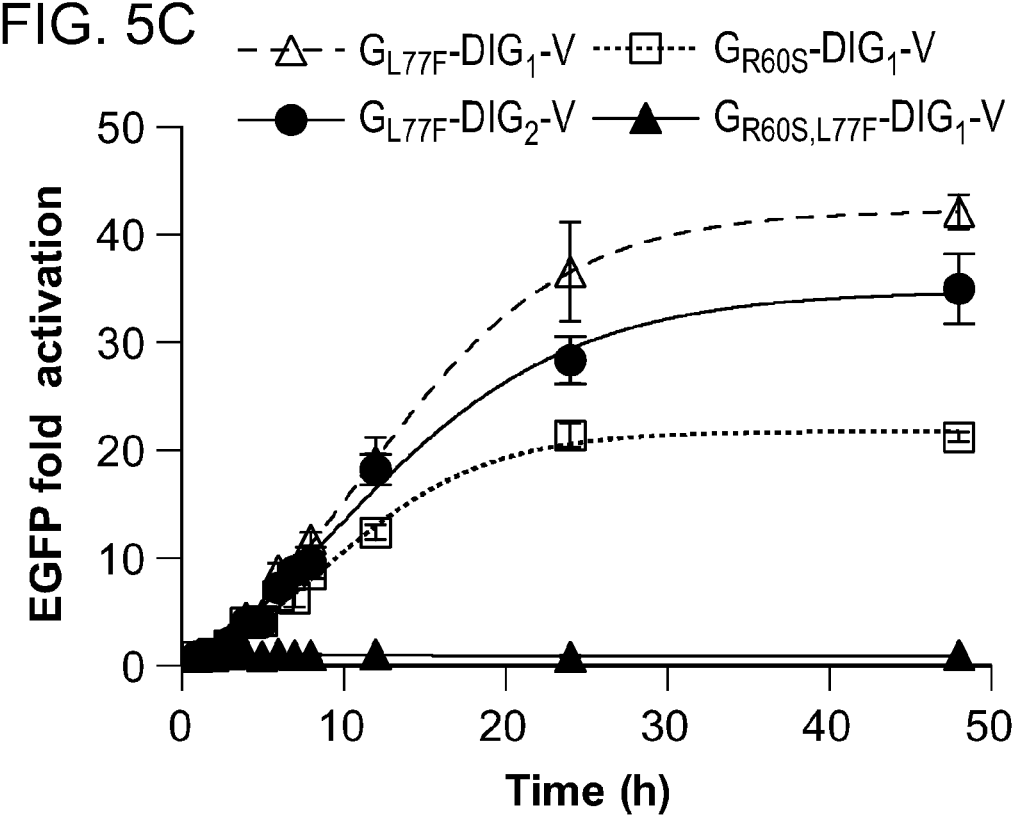
Figure 5D:
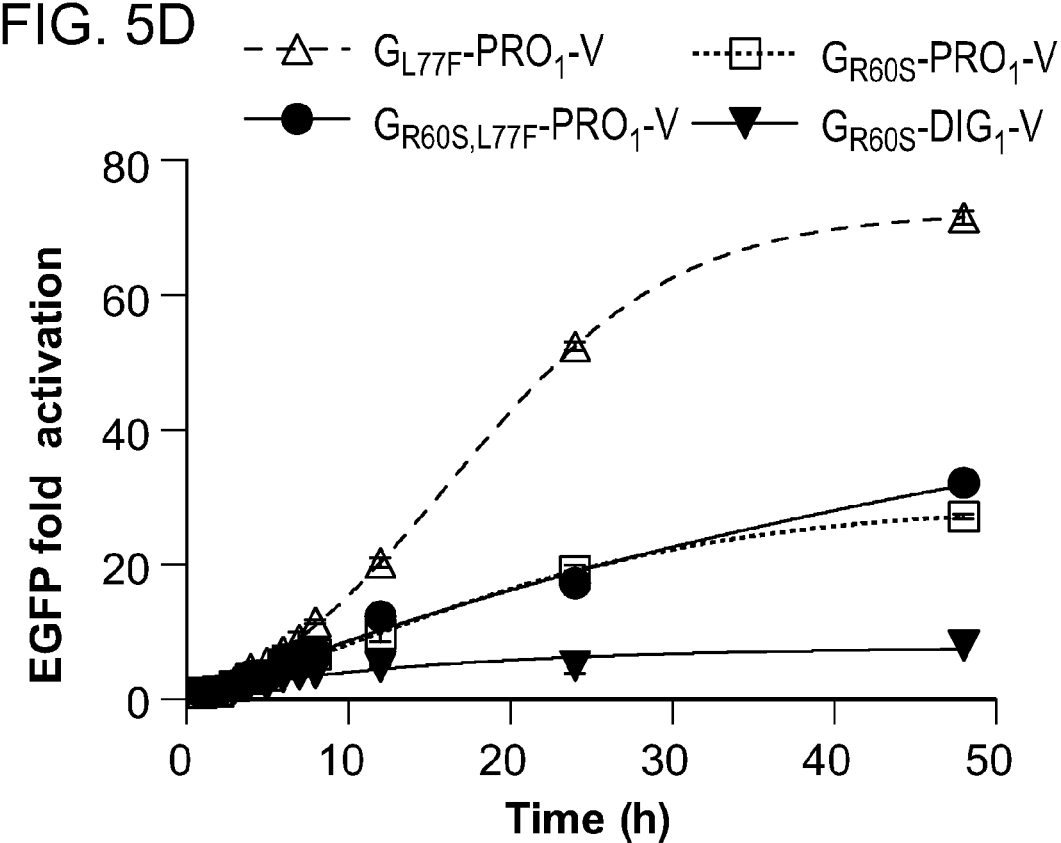
Figure 5E:
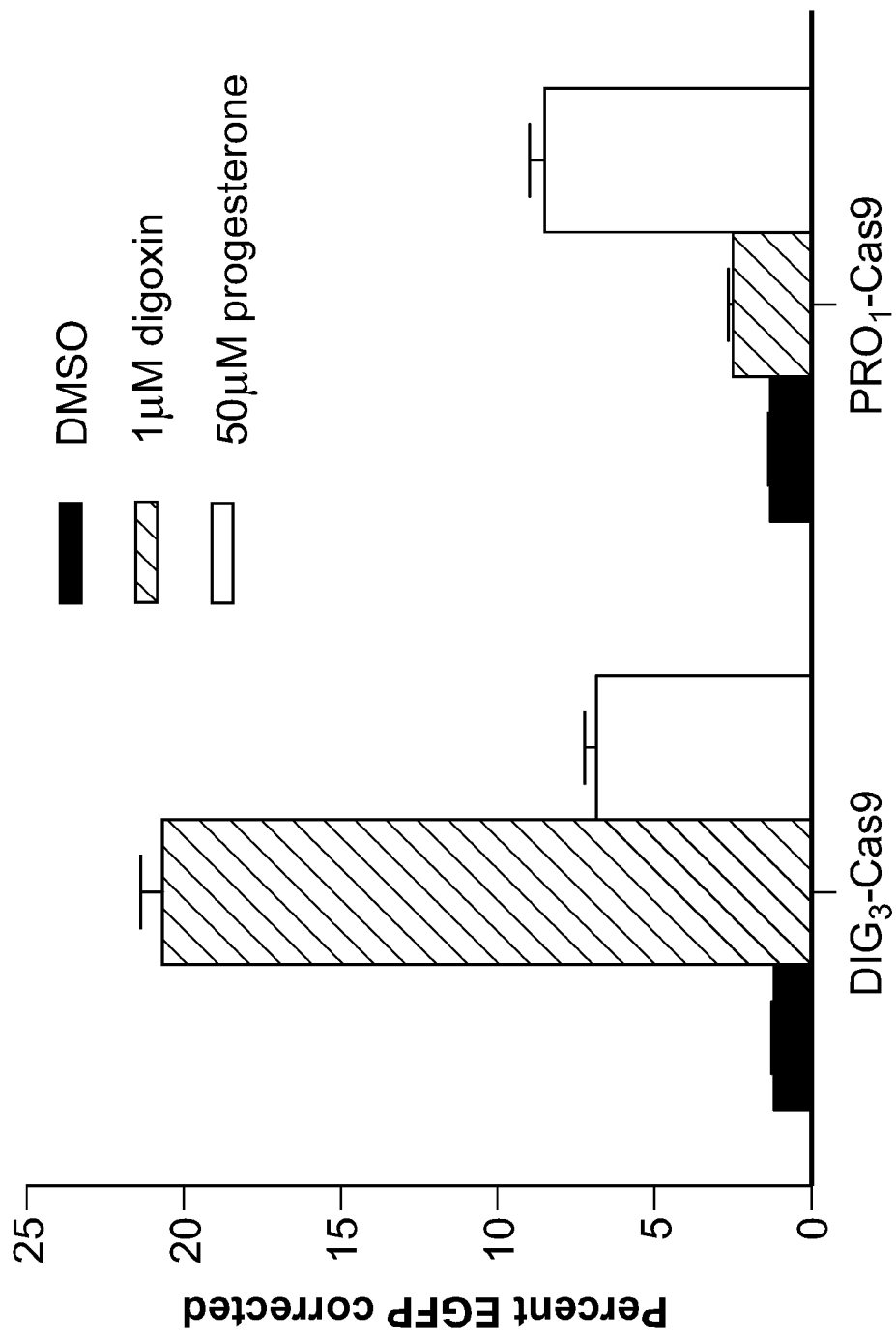
Figures 6A, 6B:
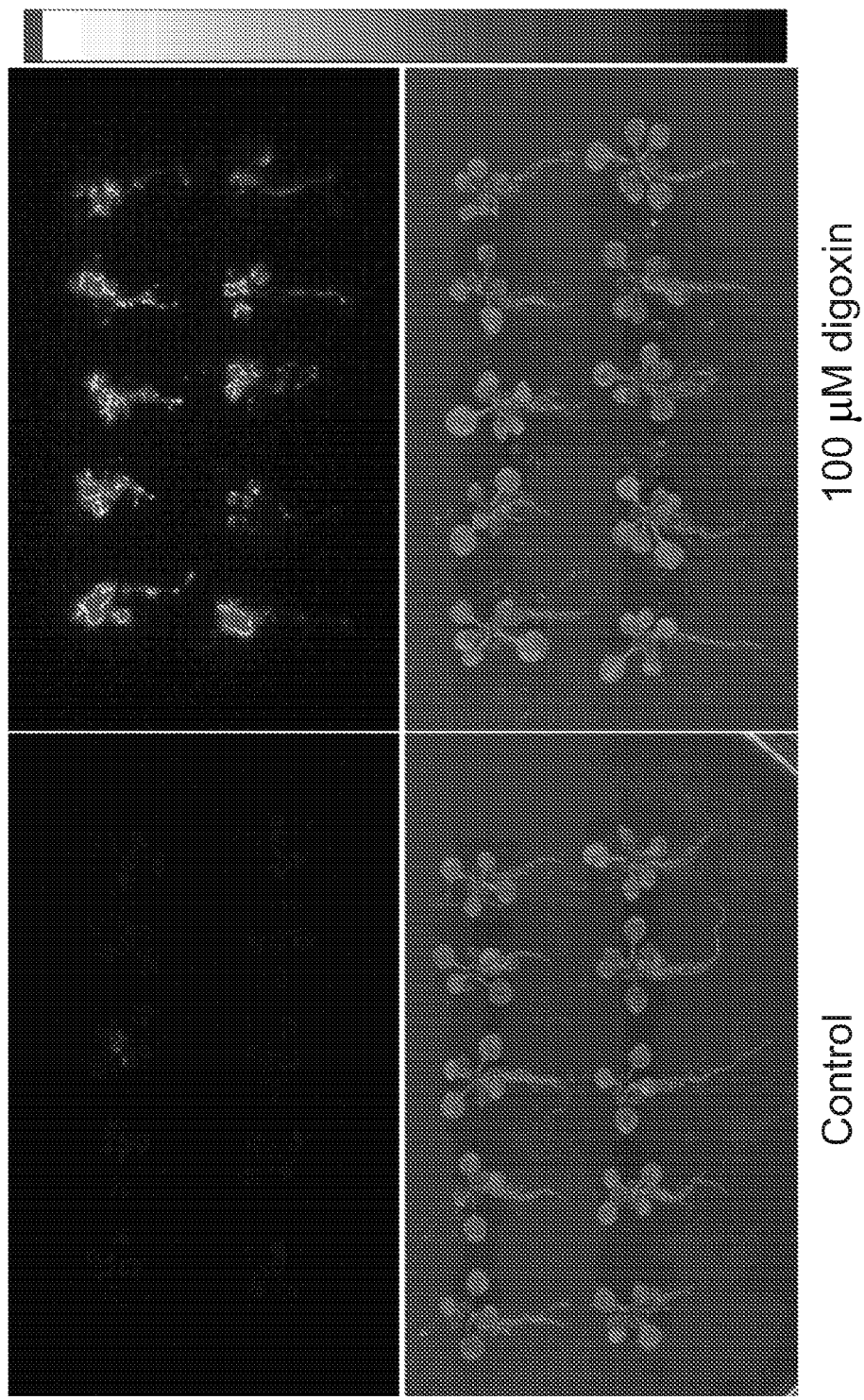
FIG. 6A depicts activation of luciferase expression in transgenic Arabidopsis plants containing the G-DIG1-V biosensor in the absence (left) or presence (right) of 100 μM digoxin. Luciferase expression levels are false colored according to scale to the right.
FIG. 6B is a brightfield image of plants shown in FIG. 6A.
Figure 6C:
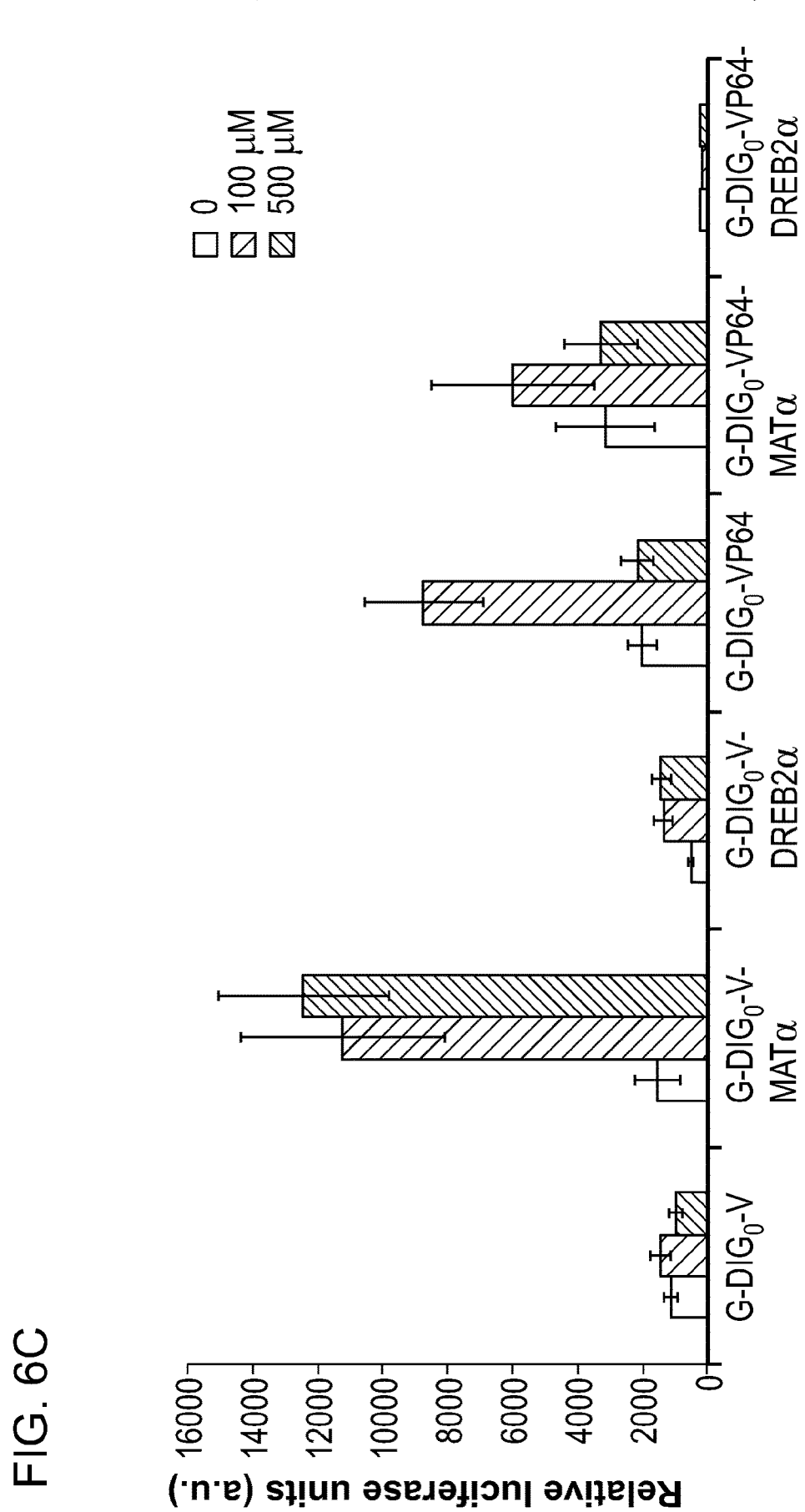
FIG. 6C depicts test of DIG0 variants engineered for plant function in Arabidopsis protoplasts. Two activation domains TADs, VP16 (V) and VP64 (VP64), as well as two degrons, yeast MATα and Arabidopsis DREB2a, were added to DTF-1 (G-DIG0), and the proteins were constitutively expressed from the CaMV35S promoter. The Gal4-activated pUAS promoter controls expression of a luciferase reporter. Transformed protoplasts were incubated with digoxigenin at 0, 100 μM, and 500 μM for 16 hours.
Figure 6D:
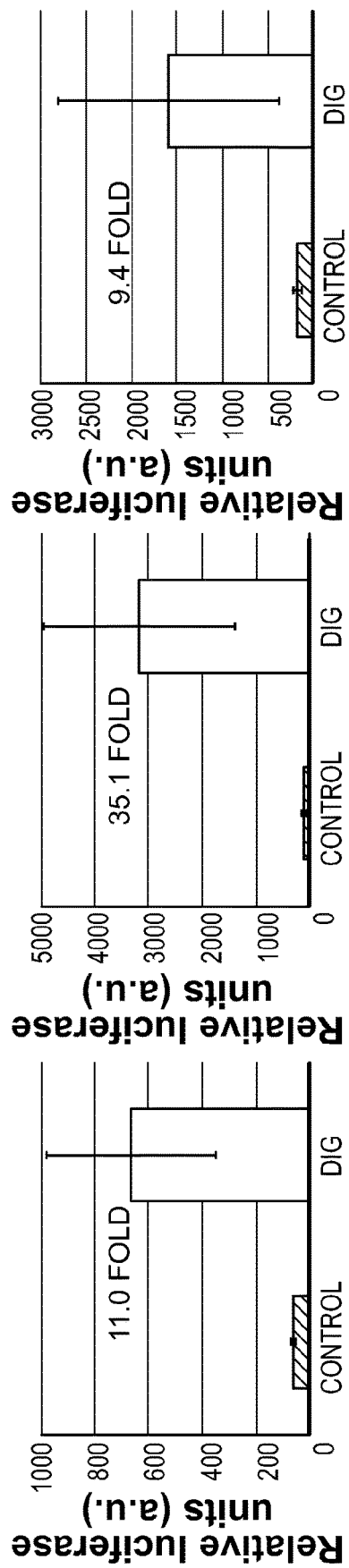
FIG. 6D depicts digoxigenin-dependent activation of luciferase expression in three independent transgenic Arabidopsis lines. Plants were incubated in the absence (Control) or presence (DIG) of 100 μM digoxigenin for 42 hours and imaged. Quantification of luciferase expression is presented as mean relative luciferase units±s.d. of ten plants.
Figure 6D:
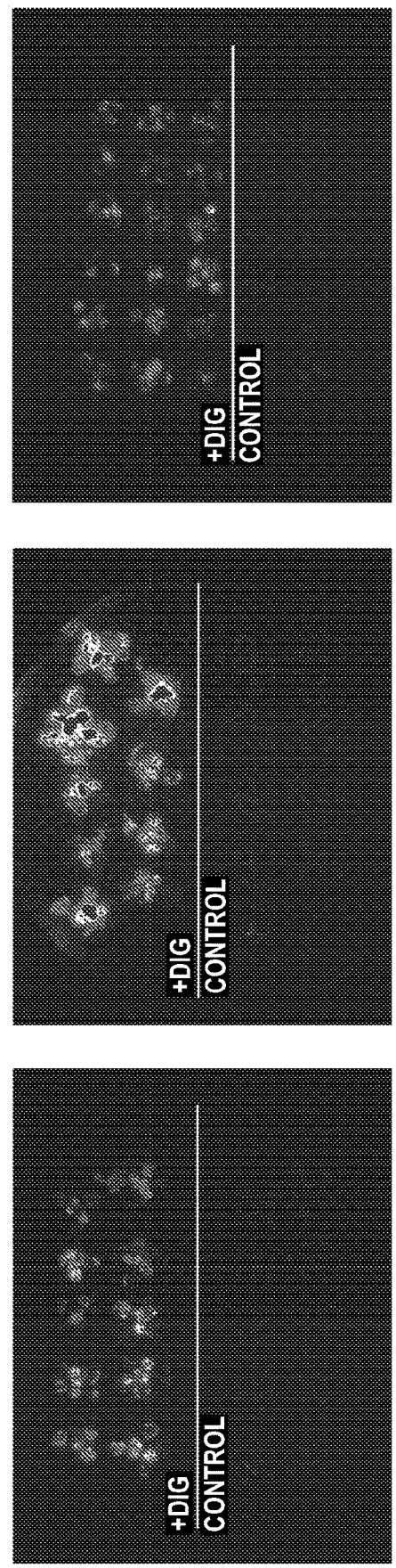
Figures 6E, 6F:
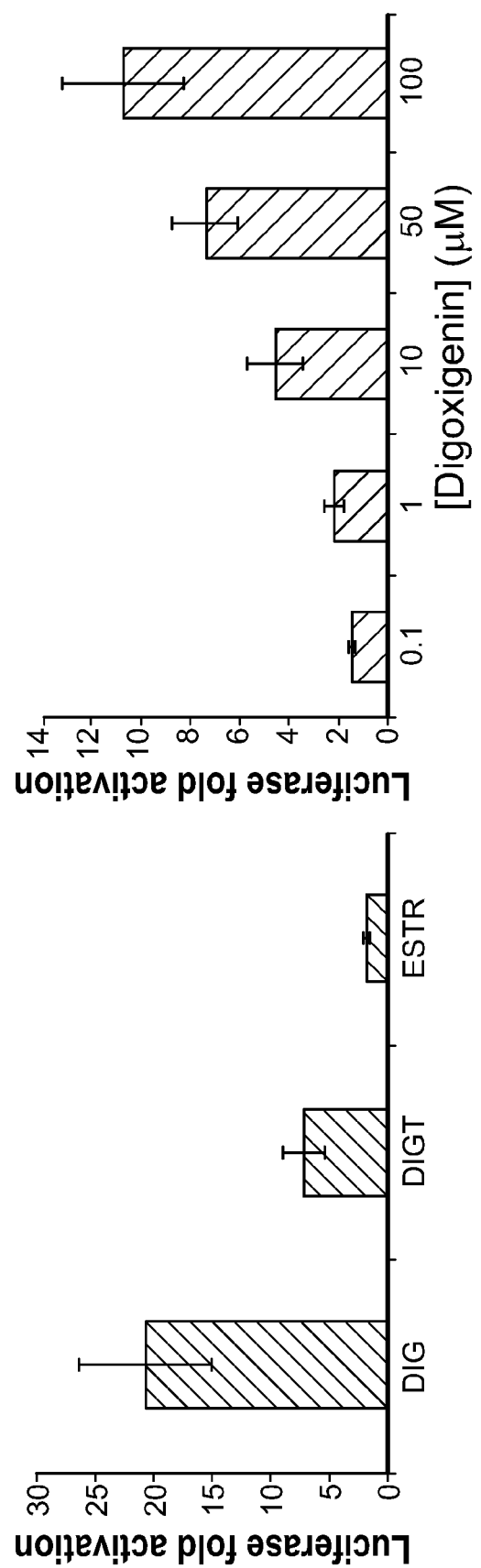
FIG. 6E depicts digoxigenin dose response curve in transgenic Arabidopsis plants. Concentrations are expressed in micromolar. Data are presented as mean fold induction relative to the control±s.e.m. of ten technical replicates.
FIG. 6F depicts the specificity of luciferase activation in transgenic Arabidopsis plants. All inducers were tested at 100 μM concentration. DIG, digoxigenin; DIGT, digitoxigenin; β-EST, β-Estradiol. Data are presented as mean fold activation relative to the control±s.e.m. of ten technical replicates.

By exploiting the low background of the LBD biosensors, biosensor-Cas9 fusions were produced with tightly controlled activation (FIG. 5E). This switch-like control over CRISPR/Cas9 activity could reduce background activity and off-target editing, a critical feature for safer gene therapies, Mandal, P. K. et al., Efficient Ablation of Genes in Human Hematopoietic Short Article Efficient Ablation of Genes in Human Hematopoietic Stem and Effector Cells using CRISPR/Cas9. Stem Cell 15, 643-652 (2014); Wu, Y. et al., Correction of a genetic disease in mouse via use of CRISPR-Cas9. Cell Stem Cell 13, 659-662 (2013); Schwank, G. et al., Functional repair of CFTR by CRISPR/Cas9 in intestinal stem cell organoids of cystic fibrosis patients. Cell Stem Cell 13, 653-658 (2013).

The disclosed biosensor design approach should have numerous applications in agriculture. For example, biosensors could be developed to enable plants to monitor the environment for pollutants, toxins or dangerous compounds. Coupling biosensors with a phytoremediation trait could enable plants to both sense a contaminant and activate a bioremediation gene circuit. When paired with an agronomic or biofuel trait, such biosensors could serve as triggers for bioproduction.

In the transgenic *Arabidopsis* plants, ligand-dependent activation was observed in all cells, tissues and organs examined (FIGS. 6A-6F), although the degree of activation may be influenced by plant age, developmental state, or cell expansion.

The technology introduced here operates at either the transcriptional or post-translational level. These biosensors can be developed in yeast and readily transferred with minimal modification to other eukaryotic cell types, where they retain a high level of sensitivity (FIG. 7C). The generality of the disclosed approach arises from the universality of the transcriptional activation and protein degradation machinery across eukaryotes, together with the modularity and tunability of the constituent parts. These biosensors should find broad application, including improving metabolically engineered pathway flux and product titers, exerting ligand-dependent control over genome editing, and detecting exogenous small molecules or endogenous metabolites.

It is to be understood that the embodiments of the present disclosure which have been described are merely illustrative of some of the applications of the principles of the present disclosure. Numerous modifications may be made by those skilled in the art based upon the teachings presented herein without departing from the true spirit and scope of the disclosure. The contents of all references, patents and published patent applications cited throughout this application are hereby incorporated by reference in their entirety for all purposes.

The following examples are set forth as being representative of the present disclosure. These examples are not to be construed as limiting the scope of the disclosure as these and other equivalent embodiments will be apparent in view of the present disclosure, figures, tables, and accompanying claims.

DIG3 and PRO1: all sensors are based on the DIG10.3 ligand binding domain (LBD) sequence defined in Nature, 2013, 501 (7466): 212-216. DIG3 contains the additional LBD mutation N120G to turn it into a sensor for digoxigenin and digoxin. PRO1 contains the additional LBD mutations H9R, E15G, I64F and A92T to turn it into a sensor for progesterone. Both sensor DIG3 and PRO1 constructs also contain the L77F mutation to Gal4, which increase dynamic range when sensing their cognate ligands.

Culture and Growth Conditions:

Growth media consisted of YPAD (10 g/L yeast extract, 20 g/L peptone, 40 mg/L adenine sulfate, 20 g/L glucose) and SD media (1.7 g/L yeast nitrogen base without amino acids, 5 g/L ammonium sulfate, 20 g/L glucose and the appropriate amount of dropout base with amino acids [Clontech]).

The following selective agents were used when indicated: G418 (285 mg/L), pen/strep (100 U/mL penicillin and 100 ug/mL streptomycin). LBD-yEGFP library construction. The DIG10.3 sequence, Tinberg, C. E. et al., Computational design of ligand-binding proteins with high affinity and selectivity, Nature, 501, 212-6 (2013), was cloned by Gibson assembly, Gibson, D. G. et al., Enzymatic assembly of DNA molecules up to several hundred kilobases. Nat. Methods 6, 343-345 (2009), into a pUC19 plasmid containing yeast enhanced GFP (yEGFP, UniProt ID B6UPG7) and a KanMX6 cassette flanked by 1000 and 500 bp upstream and downstream homology to the HO locus.

The DIG10.3 sequence was randomized by error-prone PCR using a Genemorph II kit from Agilent Technologies. An aliquot containing 100 ng of target DNA (423 bp out of a 7.4 kb plasmid) was mixed with 5 μL of 10× Mutazyme buffer, 1 μL of 40 mM dNTPS, 1.5 μL of 20 μM forward and reverse primer containing 90 bp overlap with the pUC19 plasmid (oJF70 and oJF71), and 1 μL of Mutazyme polymerase in 50 μL. The reaction mixture was subject to 30 cycles with Tm of 60° C. and extension time of 1 min.

Vector backbone was amplified using Q5 polymerase (NEB) with oJF76 and oJF77 primers with Tm of 65° C. and extension time of 350 s. Both PCR products were isolated by 1.5% agarose gel electrophoresis and the randomized target was inserted as a genetic fusion to yEGFP by Gibson assembly, Gibson, D. G. et al., Enzymatic assembly of DNA molecules up to several hundred kilobases. Nat. Methods 6, 343-345 (2009).

Assemblies were pooled, washed by ethanol precipitation, and resuspended in 50 μL of dH2O, which was drop dialyzed (Millipore) and electroporated into *E. cloni* supreme cells (Lucigen). Sanger sequencing of 16 colonies showed a mutation rate of 0-7 mutations/kb. The library was expanded in culture and maxiprepped (Qiagen) to 500 μg/μl aliquots. 16 μg of library was drop dialyzed and electrotransformed into yeast strain Y7092 for homologous recombination into the HO locus.

Integrants were selected by growth on YPAD solid media containing G418 followed by outgrowth in YPAD liquid media containing G418.

Example I

LBD-yEGFP Library Selections

Libraries of DIG0-yEGFP and PRO0-yEGFP integrated into yeast strain Y7092 were subject to three rounds of fluorescence activated sorting in a BD FACSAria IIu.

For the first round, cells were grown overnight to an OD600 of ~1.0 in YPAD containing steroid (500 μM digoxigenin or 50 μM progesterone), and cells showing the top 5% of fluorescence activation were collected and expanded overnight to an OD600 of ~1.0 in YPAD lacking steroid.

In the second sort, cells displaying the lowest ~3% fluorescence activation were collected. Cells passing the second round were passaged overnight in YPAD containing steroid to an OD600 of ~1.0 and sorted once more for the upper 5% of fluorescence activation. The sorted libraries were expanded in YPAD liquid culture and plated on solid YPAD media. Ninety-six colonies from each library were clonally isolated and grown overnight in deep well plates containing 500 μL of YPAD.

Candidates were diluted 1:50 into two deep well plates with SD-complete media: one plate supplemented with steroid and the other with DMSO vehicle. Cells were grown for another 4 h, and then diluted 1:3 into microtitre plates of 250 μL of the same media. Candidates were screened by analytical flow cytometry on a BD LSRFortessa cell analyzer. The forward scatter, side scatter, and yEGFP fluorescence (530 nm band pass filter) were recorded for a minimum of 20,000 events. FlowJo X software was used to analyze the flow cytometry data. The fold activation was calculated by normalizing mean yEGFP fluorescence activation for each steroid to the mean yEGFP fluorescence in the DMSO only control. Highest induction candidates were subject to Sanger sequencing with primers flanking the LBD sequence.

Example II

G-DIG-V Library Selections

An error-prone library of G-DIG0/DIG1/DIG2/-V transformed into yeast strain PyE1 ΔPDR5 (see Extended Experimental Procedures) was subjected to three rounds of cell sorting using a Cytopeia (BD Influx) fluorescence activated cell sorter.

For the first round, cells displaying high fluorescence in the presence of digoxin (on-state) were collected. Transformed cells were pelleted by centrifugation (4 min, 4000 rpm) and resuspended to a final OD600 of 0.1 in 50 mL of SD-ura media, pen/step antibiotics, and 5 μM digoxin prepared as a 100 mM solution in DMSO. The library was incubated at 30° C. for 9 h and then sorted. Cells displaying the highest fluorescent values in the GFP channel were collected (1,747,058 cells collected of 32,067,013 analyzed; 5.5%), grown up at 30° C. in SD-ura, and passaged twice before the next sort.

For the second round of sorting, cells displaying low fluorescence in the absence of digoxin (off-state) were collected. Cells were pelleted by centrifugation (4 min, 4000 rpm) and resuspended to a final OD600 of 0.1 in 50 mL of SD-ura media supplemented with pen/strep antibiotics. The library was incubated at 30° C. for 8 h and then sorted. Cells displaying low fluorescent values in the GFP channel were collected (1,849,137 cells collected of 22,290,327 analyzed; 11.1%), grown up at 30° C. in SD-ura, and passaged twice before the next sort.

For the last sorting round, cells displaying high fluorescence in the presence of digoxin (onstate) were collected. Cells were prepared as for the first sort. Cells displaying the highest fluorescent values in the GFP channel were collected (359,485 cells collected of 31,615,121 analyzed; 1.1%). After the third sort, a portion of cells were plated and grown at 30° C. Plasmids from 12 individual colonies were harvested using a Zymoprep Yeast miniprep II kit (Zymo Research Corporation, Irvine, Calif.) and the gene was amplified by 30 cycles of PCR (98° C. 10 s, 52° C. 30 s, 72° C. 40 s) using Phusion high-fidelity polymerase (NEB, Waltham, Mass.) with the T3 and T7 primers. Sanger sequencing (Genewiz, Inc., South Plainfield, N.J.) was used to sequence each clone in the forward (T3) and reverse (T7) directions.

Example III

Yeast Spotting Assays

Yeast strain PJ69-4a transformed with p16C plasmids containing degron G-DIG-V variants were first inoculated from colonies into SD-ura media and grown at 30° C. overnight (16 h). 1 mL of each culture was pelleted by centrifugation (3000 rcf, 2 min), resuspended in 1 mL of fresh SD-ura and the OD660 was measured. Each culture was then diluted in SD-ura media to an OD660=0.2 and incubated at 30° C. for 4-6 hrs. 1 mL of each culture was pelleted and resuspended in sterile, distilled water and the OD660 measured again. Each transformant was then diluted to an OD660=0.1. Four 1/10 serial dilutions of each culture were prepared in sterile water (for a total of 5 solutions). 10 µL of each dilution was spotted in series onto several SD-ura-his agar plates containing 1 mM 3-aminotriazole and the indicated steroid.

Steroid solutions were added to agar from 200× steroid solutions in DMSO (0.5% DMSO final in plates). TF-biosensor reporter plasmid construction and integration. Reporter genes were cloned into the integrative plasmid pUG6 or the CEN plasmid pRS414 using the Gibson method, Gibson, D. G. et al., Enzymatic assembly of DNA molecules up to several hundred kilobases. Nat. Methods 6, 343-345 (2009). Each reporter (either yEGFP or firefly luciferase) was cloned to include a 5' GAL1 promoter (*S. cerevisiae* GAL1 ORF bases (−455)-(−5)) and a 3' CYC1 terminator. For integration, linearized PCR cassettes containing both the reporter and an adjacent KanMX antibiotic resistance cassette were generated using primers containing 50 bp flanking sequences of homology to the URA3 locus. Integrative PCR product was transformed into the yeast strain PJ69-4a using the Gietz method, Gietz, R. D. & Schiestl, R. H. High-efficiency yeast transformation using the LiAc/SS carrier DNA/PEG method. Nat. Protoc. 2, 31-4 (2007), to generate integrated reporter strains.

Example IV

G-DIG/PRO-V Plasmid Construction

G-DIG/PRO-V fusion constructs were prepared using the Gibson method (PMID 19363495). Constructs were cloned into the plasmid p416CYC (p16C). Gal4 (residues 1-93, UniProt ID P04386), DIG10.3 (PMID 24005320), and VP16 (residues 363-490, UniProt ID P06492) PCR products for were amplified from their respective templates using Phusion high-fidelity polymerase (NEB, Waltham, Mass.) and standard PCR conditions (98° C. 10 s, 60° C. 20 s, 72° C. 30 s; 30 cycles).

The 8-residue linker sequence GGSGGSGG (SEQ ID NO:1) was used between Gal4 and DIG10.3. PCR primers were purchased from Integrated DNA technologies and contained 24-30 5' bases of homology to either neighboring fragments or plasmid. Clones containing an N-terminal degron were similarly cloned fusing residues 1-67 of Mat-alpha2 (UniProt ID P0CY08) to the 5'-end of G-DIG-V. Plasmids were transformed into yeast using the Gietz method (PMID 17401334), with transformants being plated on synthetic complete media lacking uracil (SD-ura).

Example V

G-DIG-V Mutant Construction

Mutations were introduced into DIG10.3/pETCON14 or the appropriate G-DIG/PRO-V construct using Kunkel mutagenesis, Kunkel, T. a. Rapid and efficient site-specific mutagenesis without phenotypic selection., Proc. Natl. Acad. Sci. U.S.A. 82, 488-492 (1985). Oligos were ordered from Integrated DNA Technologies, Inc. For mutants constructed in pETCON/DIG10.3, the mutagenized DIG10.3 gene was amplified by 30 cycles of PCR (98° C. 10 s, 61° C. 30 s, 72° C. 15 s), using Phusion high-fidelity polymerase (NEB, Waltham, Mass.) and 5'- and 3'-primers having homologous overlap with the DIG10.3-flanking regions in p16C-G-DIG-VP64 (Gal4_DIG10.3_VP64_hr_fwd and Gal4_DIG10.3_VP64_hrrev_rc). Genes were inserted into p16C-Gal4-(HE)-VP16 by Gibson assembly, Gibson, D. G. et al., Enzymatic assembly of DNA molecules up to several hundred kilobases. Nat. Methods 6, 343-345 (2009), using vector digested with HindIII and EcoRI-HF.

Example VI

G-PRO-V Mutant Construction

The gene for DIG10.3 Y34F/Y99F/Y101F were amplified from the appropriate DIG10.3/pETCON (PMID 24005320) construct by 30 cycles of PCR (98° C. 10 s, 59° C. 30 s, 72° C. 15 s) using Phusion high-fidelity polymerase (NEB, Waltham, Mass.) and 5'- and 3'-primers having homologous overlap with the DIG10.3-flanking regions in p16CG-DIG-VP64 (DIG_fwd and DIG_rev). Genes were inserted into p16C-GDVP16 by Gibson assembly, Gibson, D. G. et al., Enzymatic assembly of DNA molecules up to several hundred kilobases. Nat. Methods 6, 343-345 (2009), using p16C-Gal4-(HE)-VP16 vector digested with HindIII and EcoRI-HF.

Example VII

G-DIG-V Error-Prone Library Construction

A randomized G-DIG-V library was constructed by error-prone PCR using a Genemorph II kit from Agilent Technologies. An aliquot containing 20 ng p16C GDVP16, 20 ng p16C GDVP16 E83V, and 20 ng p16C Y36H was mixed with 5 µL of 10× Mutazyme buffer, 1 µL of 40 mM dNTPS, 1.5 µL of 20 µM forward and reverse primer containing 37- and 42-bp overlap with the p16C vector for homologous recombination, respectively (GDV_ePCR_fwd and GDV_e-PRC_rev), and 1 µL of Mutazyme polymerase in 50 µL. The reaction mixture was subjected to 30 cycles of PCR (95° C. 30 s, 61° C. 30 s, 72° C. 80 s).

Template plasmid was digested by adding 1 µL of DpnI to the reaction mixture and incubating for 3 hr at 37° C. Resulting PCR product was purified using a Quiagen PCR cleanup kit, and a second round of PCR was used to amplify enough DNA for transformation. Gene product was amplified by combining 100 ng of mutated template DNA with 2.5 µL of 10 µM primers (GDV_ePCR_fwd and GDV_ePR-C_rev), 10 µL of 5× Phusion buffer HF, 1.5 µL of DMSO, and 1 μL of Phusion high-fidelity polymerase (NEB, Waltham, Mass.) in 50 μL. Product was assembled by 30 cycles of PCR (98° C. 10 s, 65° C. 30 s, 72° C. 35 s).

Following confirmation of a single band at the correct molecular weight by 1% agarose gel electrophoresis, the PCR product was purified using a Quaigen PCR cleanup kit and eluted in ddH2O. Yeast strain PyE1 ΔPDR5 was transformed with 9 μg of amplified PCR library and 3 μg of p16C Gal4-(HE)-VP16 triply digested with SalI-HF, BamHI-HR, and EcoRI-HF using the method of Benatuil, Benatuil, L., Perez, J. M., Belk, J. & Hsieh, C.-M. M. An improved yeast transformation method for the generation of very large human antibody libraries. Protein Eng. Des. Sel. 23, 155-9 (2010), yielding ~106 transformants. Following transformation, cells were grown in 150 mL of SD-ura media. Sanger sequencing of 12 individual colonies revealed an error rate of ~1-6 mutations per gene.

Example VIII

G-DIG-V Error-Prone Library Mutation Screens

Of twelve sequenced clones from the library sorts, two showed significantly improved (>2-fold) response to DIG over the input clones (clone 3 and clone 6). Clone 3 contains the following mutations: Gal4_T44T (silent), Gal4_L77F, DIG10.3_E5D, DIG10.3_E83V, DIG10.3_R108R (silent), DIG10.3_L128P, DIG10.3_I137N, DIG10.3_S143G, and VP16_A44T. Clone 6 contains the following mutations: Gal4_R60S, Gal4_L84L (silent), VP16_G17G (silent), VP16_L48V, and VP16_H98H (silent). To identify which mutations led to the observed changes in DIG response, variants of these clones with no silent mutations and each individual point mutant were constructed using Kunkel mutagenesis, Kunkel, T. a. Rapid and efficient site-specific mutagenesis without phenotypic selection., Proc. Natl. Acad. Sci. U.S.A. 82, 488-492 (1985).

Oligos were ordered from Integrated DNA Technologies, Inc. Sequence-confirmed plasmids were transformed into PyE1 ΔPDR5f and plated onto selective SD-ura media. Individual colonies were inoculated into liquid media, grown at 30° C., and passaged once. Cells were pelleted by centrifugation (4 min, 1700×g) and resuspended to a final OD660 of 0.1 in 1 mL of SD-ura media supplemented 50 μM DIG prepared as a 100 mM solution in DMSO.

Following a 6 hr incubation at 30° C., cells were pelleted, resuspended in 200 μL of PBS, and cellular fluorescence was measured on an Accuri C6 flow cytometer using a 488 nm laser for excitation and a 575 nm band pass filter for emission. FlowJo software version 7.6 was used to analyze the flow cytometry data. Data are given as the mean yEGFP fluorescence of the single yeast population in the absence of DIG (off-state) and the mean yEGFP fluorescence of the higher fluorescing yeast population in the presence of DIG (on-state).

Example IX

Computational Model of Gal4-DIG

A model of the Gal4-DIG10.3 fusion was built using Rosetta Remodel (PMID 21909381) to assess whether the linker between Gal4 and the DIG LBD, which are both dimers, would allow for the formation of a dimer in the fusion construct. In the simulation, the Gal4 dimer was held fixed while the relative orientation of the DIG LBD monomers were sampled symmetrically using fragment insertion in the linker region. Constraints were added across the DIG LBD dimer interface to facilitate sampling. The lowest energy model satisfied the dimer constraints, indicating that a homodimer configuration of the fusion is possible.

Example X

TF-Biosensor Titration Assays in Yeast

Yeast strain PyE1 transformed with p16C plasmids containing G-LBD-V variants were inoculated from colonies into SD-ura media supplemented and grown at 30° C. overnight (16 h). 10 μL of the culture was resuspended into 490 μL of separately prepared media each containing a steroid of interest (SD-ura media supplemented the steroid of interest and DMSO to a final concentration of 1% DMSO). Resuspended cultures were then incubated at 30° C. for 8 hours. 125 μL of incubated culture was resuspended into 150 μL of fresh SD-ura media supplemented with the steroid of interest and DMSO to a final concentration of 1%.

These cultures were then assayed by analytical flow cytometry on a BD LSRFortessa using a 488 nm laser for excitation. The forward scatter, side scatter, and yEGFP fluorescence (530 nm band pass filter) were recorded for a minimum of 20,000 events. FlowJo X software was used to analyze the flow cytometry data. The fold activation was calculated by normalizing mean yEGFP fluorescence activation for each steroid to the mean yEGFP fluorescence in the DMSO only control. G-PRO0-V was assayed on a separate day from the other TF biosensors under identical conditions.

Example XI

TF-Biosensor Kinetic Assays in Yeast

Yeast strain PyE1 was transformed with p16C plasmids containing G-LBD-V variants were inoculated from colonies into SD-ura media and grown at 30° C. overnight (16 h). 5 μL of each strain was diluted into 490 μL of SD-ura media in 2.2 mL plates. Cells were incubated at 30° C. for 8 hours. 5 μL of steroid was then added for a final concentration of 250 μM digoxin or 50 μM progesterone.

For each time point, strains were diluted 1:3 into microtitre plates of 250 μL of the same media. Strains were screened by analytical flow cytometry on a BD LSRFortessa cell analyzer. The forward scatter, side scatter, and yEGFP fluorescence (530 nm band pass filter) were recorded for a minimum of 20,000 events. FlowJo X software was used to analyze the flow cytometry data. The fold activation was calculated by normalizing mean yEGFP fluorescence activation for each time point to the mean yEGFP fluorescence at T=0 h.

Example XII

Luciferase Reporter Assay

Yeast strains containing either a plasmid-borne or integrated luciferase reporter were transformed with p16C plasmids encoding TF-biosensors. Transformants were grown in triplicate overnight at 30° C. in SD-ura media containing 2% glucose in sterile glass test tubes on a roller drum. After ~16 hours of growth, OD600 of each sample was measured and cultures were back diluted to OD600=0.2 in fresh SD-ura media containing steroid dissolved in DMSO or a DMSO control (1% DMSO final). Cultures were grown at 30° C. on roller drum for 8 hrs prior to taking readings. Measurement of luciferase activity was adapted from a previously reported protocol[58]. 100 uL of each culture was transferred to a 96-well white NUNC plate. 100 uL of 2 mM D-luciferin in 0.1 M sodium citrate (pH 4.5) was added to each well of the plate and luminescence was measured on a Victor 3V after 5 minutes.

Example XIII

Yeast Deletion Strain Creation

Genomic deletions were introduced into the yeast strains PJ69-4a and PyE1 using the 50:50 method, Horecka, J. & Davis, R. W. The 50:50 method for PCR-based seamless genome editing in yeast. Yeast 26, 545-551 (2013). Briefly, forward and reverse primers were used to amplify an URA3 cassette by PCR. These primers generated a product containing two 50 bp sequences homologous to the 5' and 3' ends of the ORF at one end and a single 50 bp sequence-homologous to the middle of the ORF at the other end. PCR products were transformed into yeast using the Gietz method, Gietz, R. D. & Schiestl, R. H. High-efficiency yeast transformation using the LiAc/SS carrier DNA/PEG method. Nat. Protoc. 2, 31-4 (2007), and integrants were selected on SD-ura plates.

After integration at the correct locus was confirmed by a PCR screen, single integrants were grown for 2 days in YEP containing 2.5% ethanol and 2% glycerol. Each culture was plated on synthetic complete plates containing 5-fluoroorotic acid. Colonies were screened for deletion of the ORF and elimination of the Ura3 cassette by PCR and confirmed by DNA sequencing.

Example XIV

TF-Biosensor Specificity Assays

Yeast strains expressing the TF-biosensors and yEGFP reporter (either genetically fused or able to be transcriptionally activated by the TAD) were grown overnight at 30° C. in SD-ura media for 12 hours. Following overnight growth, cells were pelleted by centrifugation (5 min, 5250 rpm) and resuspended into 500 µL of SD-ura. 10 µL of the washed culture was resuspended into 490 µL of separately prepared media each containing a steroid of interest (SD-ura media supplemented with the steroid of interest and DMSO to a final concentration of 1% DMSO). Steroids were tested at a concentration of 100 µM digoxin, 50 µM progesterone, 250 µM pregnenolone, 100 µM digitoxigenin, 100 µM beta-estradiol, and 100 µM hydrocortisone. Stock solutions of steroids were prepared as a 50 mM solution in DMSO.

Resuspended cultures were then incubated at 30° C. for 8 hours. 125 µL of incubated culture was resuspended into 150 µL of fresh SD-ura media supplemented the steroid of interest, and DMSO to a final concentration of 1%. These cultures were then assayed by analytical flow cytometry on a BD LSRFortessa using a 488 nm laser for excitation. The forward scatter, side scatter, and yEGFP fluorescence (530 nm band pass filter) were recorded for a minimum of 20,000 events. FlowJo X software was used to analyze the flow cytometry data. The fold induction was calculated by normalizing mean yEGFP fluorescence activation for each steroid to the mean yEGFP fluorescence in the DMSO only control.

Example XV

3β-HSD Plasmid and Library Construction

The 3β-HSD ORF was synthesized as double stranded DNA (Integrated DNA Technologies, Inc.) and amplified using primers oJF325 and oJF326 using KAPA HiFi under standard PCR conditions and digested with BsmBI to create plasmid pJF57. 3β-HSD expression plasmids (pJF76 through pJF87) were generated by digesting plasmid pJF57 along with corresponding plasmids from the Yeast Cloning Toolkit, Lee, M. E., DeLoache, W. C., Cervantes, B. & Dueber, J. E. A Highly-characterized Yeast Toolkit for Modular, Multi-part Assembly. ACS Synth. Biol. 150414151809002 (2015). doi:10.1021/sb500366v, with BsaI and assembled using the Golden Gate Assembly method, Engler, C., Kandzia, R. & Marillonnet, S. A one pot, one step, precision cloning method with high throughput capability. PLoS One 3, (2008). The 3β-HSD sequence was randomized by error-prone PCR using a Genemorph II kit from Agilent Technologies.

An aliquot containing 100 ng of target DNA was mixed with 5 µL of 10× Mutazyme buffer, 1 µL of 40 mM dNTPS, 1.5 µL of 20 µM forward and reverse primer containing 90-bp overlap with the 3β-HSD expression plasmids and 1 µL of Mutazyme polymerase in 50 µL. The reaction mixture was subject to 30 cycles with Tm of 60° C. and extension time of 1 min. Vector backbone was amplified using KAPA HiFi polymerase with oJF387 and oJF389 (pPAB1) or oJF387 and oJF389 (pPOP6) with Tm of 65° C. and extension time of 350 s. PCR products were isolated by 1.5% agarose gel electrophoresis and assembled using the Gibson method, Gibson, D. G. et al., Enzymatic assembly of DNA molecules up to several hundred kilobases. Nat. Methods 6, 343-345 (2009).

Assemblies were pooled, washed by ethanol precipitation, and resuspended in 50 µL of dH2O, which was drop dialyzed (Millipore) and electroporated into E. cloni supreme cells (Lucigen). Sanger sequencing of 16 colonies showed a mutation rate of 0-4 mutations/kb. The library was expanded in culture and maxiprepped (Qiagen) to 500 µg/µL aliquots. 16 µg of library was drop dialyzed and electrotransformed into yeast strain PyE1.

Example XVI

3β-HSD Progesterone Selections

PyE1 transformed with libraries of 3β-HSD (see Extended Experimental Procedures) were seeded into 5 mL of SD-ura-leu media supplemented and grown at 30° C. overnight (24 h). Cultures were measured for OD600, diluted to an OD600 of 0.0032, and 100 µL was plated onto SD-ura-leu-his plates supplemented 35 mM 3-AT and either 50 µM pregnenolone or 0.5% DMSO.

Example XVII

Progesterone Bioproduction and GC/MS Analysis

Production strains were inoculated from colonies into 5 mL SD-ura media and grown at 30° C. overnight (24 h). 1 mL of each culture was washed and resuspended into 50 mL of SD-ura with 250 mM of pregnenolone and grown at 30° C. for 76 h. OD600 measurements were recorded for each culture before pelleting by centrifugation. Cells were lysed by glass bead disruption, and lysates and growth media were extracted separately with heptane. Extractions were analyzed by GC/MS.

Example XVIII

TF-Biosensor EGFP Assays in Mammalian Cells

For each TF-biosensor, 1 μg of the PiggyBac construct along with 400 ng of transposase were nucleofected into K562 cells using the Lonza Nucleofection system as per manufacturer settings. Two days post-transfection, cells underwent puromycin selection (2 μg/mL) for at least eight additional days to allow for unintegrated plasmid to dilute out and ensure that all cells contained the integrated construct. An aliquot of 100,000 cells of each integrated population were then cultured with 25 μM of progesterone, 1 μM of digoxigenin, or no small molecule. Forty-eight hours after small molecule addition, cells were analyzed by flow cytometry using a BD Biosciences Fortessa system. Mean EGFP fluorescence of the populations was compared.

Example XIX

Construction of K562 Cell Lines

The PiggyBac transposase system was employed to integrate biosensor constructs into K562 cells. Vector PB713B-1 (Systems Biosciences) was used a backbone. Briefly, this backbone was digested with NotI and HpaI and G-LBD-V, Gal4BS-E1b-EGFP (EGFP; enhanced GFP ref or UniProt ID A0A076FL24), and sEF1-Puromycin were cloned in. Gal4BS represents four copies of the binding sequence. For hCas9, the PiggyBac system was also employed, but the biosensors were directly fused to the N-terminus of Cas9 and were under control of the CAGGS (SEQ ID NO:2) promoter. Cas9 from *S. pyogenes* was used.

Example XX

TF-Biosensor-Cas9 Assays

Construct integration was carried out as for the Cas9 experiments for EGFP assays, except that the constructs were integrated into K562 containing a broken EGFP reporter construct. Introduction of an engineered nuclease along with a donor oligonucleotide can correct the EGFP and produce fluorescent cells. Upon successful integration (~10 days after initial transfection), 500,000 cells were nucleofected with 500 ng of guide RNA (sgRNA) and 2 μg of donor oligonucleotide. Nucleofected cells were then collected with 200 μL of media and 50 μL aliquots were added to wells containing 950 μL of media. Each nucleofection was split into four separate wells containing 1 μM of digoxigenin, 25 μM of progesterone, or no small molecule. Forty-eight hours later, cells were analyzed using flow cytometry and the percentage of EGFP positive cells was determined.

Example XXI

TF-Biosensor Assays in Protoplasts

Digoxin transcriptional activators were initially tested in a transient expression assay using *Arabidopsis* protoplasts according previously described methods, Yoo, S.-D., Cho, Y.-H. & Sheen, J. *Arabidopsis* mesophyll protoplasts: a versatile cell system for transient gene expression analysis. Nat. Protoc. 2, 1565-1572 (2007), with some modifications. Briefly, protoplasts were prepared from 6-week old *Arabidopsis* leaves excised from plants grown in short days. Cellulase Onozuka R-10 and Macerozyme R-10 (Yakult Honsha, Inc., Japan) in buffered solution were used to remove the cell wall. After two washes in W5 solution, protoplasts were re-suspended in MMg solution at 2×105 cells/mL for transformation. Approximately 104 protoplasts were mixed with 5 mg of plasmid DNA and PEG4000 at a final concentration of 20%, and allowed to incubate at room temperature for 30 minutes. The transformation reaction was stopped by addition of 2 volumes of W5 solution, and after centrifugation, protoplasts were re-suspended in 200 mL of WI solution (at 5×105/mL) and plated in a 96-well plate. Digoxigenin (Sigma-Aldrich, St. Louis, Mo.) was added to the wells, and protoplasts were incubated overnight at room temperature in the dark, with slight shaking (40 rpm). For luciferase imaging, protoplasts were lysed using Passive Lysis Buffer (Promega, Madison, Wis.) and mixed with LARII substrate (Dual-Luciferase Reporter Assay System, Promega). Luciferase luminescence was collected by a Stanford Photonics XR/MEGA-10 ICCD Camera and quantified using Piper Control (v.2.6.17) software.

Example XXII

Plant Plasmid Construction

G-DIG1-V was recoded to function as a ligand-dependent transcriptional activator in plants. Specifically, an *Arabidopsis thaliana* codon optimized protein degradation sequence from the yeast MATα gene was fused in frame in between the Gal4 DBD and the DIG1 LBD. The resulting gene sequence was codon-optimized for optimal expression in *Arabidopsis thaliana* plants and cloned downstream of a plant-functional CaMV35S promoter to drive constitutive expression in plants, and upstream of the octopine synthase (ocs) transcriptional terminator sequence.

To quantify the transcriptional activation function of DIG10.3, the luciferase gene from *Photinus pyralis* (firefly) was placed downstream of a synthetic plant promoter consisting of five tandem copies of a Gal4 Upstream Activating Sequence (UAS) fused to the minimal (−46) CaMV35S promoter sequence. Transcription of luciferase is terminated by the E9 terminator sequence. These sequences were cloned into a pJ204 plasmid and used for transient expression assays in *Arabidopsis* protoplasts.

Example XXIII

Construction of Transgenic *Arabidopsis* Plants

After confirmation of function in transient tests, the digoxin biosensor genetic circuit was transferred to pCAMBIA 2300 and was stably transformed into *Arabidopsis thaliana* ecotype Columbia plants using a standard Agrobacterium floral dip method, Clough, S. J. & Bent, A. F. Floral dip: A simplified method for Agrobacterium-mediated transformation of *Arabidopsis thaliana*. Plant J. 16, 735-743 (1998). Transgenic plants were selected in MS media, Murashige, T. & Skoog, F. A revised medium for rapid growth and bio assays with tobacco tissue cultures. Physiol. Plant. 15, 473-497 (1962), containing 100 mg/L kanamycin.

Example XXIV

TF-Biosensor Assays in Transgenic Plants

Transgenic plants expressing the digoxin biosensor genetic circuit were tested for digoxigenin-induced luciferase expression by placing 14-16 day old plants in liquid MS (-sucrose) media supplemented with 0.1 mM digoxigenin in 24-well plates, and incubated in a growth chamber at 24° C., 100 mE·m$^{-2}$·s$^{-1}$ light.

Luciferase expression was measured by imaging plants with a Stanford Photonics XR/MEGA-10 ICCD Camera, after spraying luciferin and dark adapting plants for 30 minutes. Luciferase expression was quantified using Piper Control (v.2.6.17) software. Plants from line KJM58-10 were used to test for specificity of induction by incubating plants, as described above, in 0.1 mM digoxigenin, 0.1 mM digitoxigenin, and 0.02 mM β-estradiol. All chemicals were obtained from Sigma-Aldrich (St. Louis, Mo.).

The following references are cited herein, and to the extent necessary for a full understanding of the present disclosure, each of these references is hereby incorporated herein by reference in its entirety.

1. Zhang, F., Carothers, J. M. & Keasling, J. D., Design of a dynamic sensor-regulator system for production of chemicals and fuels derived from fatty acids. Nat. Biotechnol., 30, 354-9 (2012).
2. Raman, S., Rogers, J. K., Taylor, N. D. & Church, G. M., Evolution-guided optimization of biosynthetic pathways. Proc. Natl. Acad. Sci., 201409523 (2014). doi:10.1073/pnas.1409523111
3. Tang, S.-Y. & Cirino, P. C. Design and application of a mevalonate-responsive regulatory protein. Angew. Chem. Int. Ed. Engl., 50, 1084-6 (2011).
4. Paige, J. S., Nguyen-Duc, T., Song, W. & Jaffrey, S. R. Fluorescence Imaging of Cellular Metabolites with RNA. Science (80), 335, 1194-1194 (2012).
5. Gil, G. C., Mitchell, R. J., Chang, S. T. & Gu, M. B. A biosensor for the detection of gas toxicity using a recombinant bioluminescent bacterium. Biosens. Bioelectron., 15, 23-30 (2000).
6. Ye, H. et al., Pharmaceutically controlled designer circuit for the treatment of the metabolic syndrome. Proc. Natl. Acad. Sci. U.S.A., 110, 1-6 (2012).
7. Tang, S. Y. et al., Screening for enhanced triacetic acid lactone (TAL) production by recombinant *Escherichia coli* expressing a designed TAL reporter. J. Am. Chem. Soc., (2013). doi:10.1021/ja402654z.
8. Yang, J. et al., Synthetic RNA devices to expedite the evolution of metabolite-producing microbes. Nat. Commun., 4, 1413 (2013).
9. Banaszynski, L. a, Chen, L.-C., Maynard-Smith, L. a, Ooi, A. G. L. & Wandless, T. J. A rapid, reversible, and tunable method to regulate protein function in living cells using synthetic small molecules. Cell, 126, 995-1004 (2006).
10. Tucker, C. L. & Fields, S. A yeast sensor of ligand binding. Nat. Biotechnol., 19, 1042-6 (2001).
11. Egeler, E. L., Urner, L. M., Rakhit, R., Liu, C. W. & Wandless, T. J. Ligand-switchable substrates for a ubiquitin-proteasome system. J. Biol. Chem., 286, 31328-36 (2011).
12. Miyazaki, Y., Imoto, H., Chen, L. & Wandless, T. J. Destabilizing domains derived from the human estrogen receptor. J. Am. Chem. Soc., 134, 3942-5 (2012).
13. Iwamoto, M., Bjorklund, T., Lundberg, C., Kirik, D. & Wandless, T. J. A general chemical method to regulate protein stability in the mammalian central nervous system. Chem. Biol., 17, 981-8 (2010).
14. Tinberg, C. E. et al., Computational design of ligand-binding proteins with high affinity and selectivity, Nature, 501, 212-6 (2013).
15. Shoulders, M. D., Ryno, L. M., Cooley, C. B., Kelly, J. W. & Wiseman, R. L. Broadly applicable methodology for the rapid and dosable small molecule-mediated regulation of transcription factors in human cells. J. Am. Chem. Soc., 135, 8129-8132 (2013).
16. Beerli, R. R., Schopfer, U., Dreier, B. & Barbas, C. F. Chemically regulated zinc finger transcription factors. J. Biol. Chem., 275, 32617-32627 (2000).
17. Louvion, J. F., Havaux-Copf, B. & Picard, D. Fusion of GAL4-VP16 to a steroid-binding domain provides a tool for gratuitous induction of galactose-responsive genes in yeast, Gene, 131, 129-134 (1993).
18. Rakhit, R., Edwards, S. R. S., Iwamoto, M. & Wandless, T. J. Evaluation of FKBP and DHFR based destabilizing domains in *Saccharomyces cerevisiae*. Bioorganic Med., 21, 4965-4968 (2011).
19. Ernst, R., Klemm, R., Schmitt, L. & Kuchler, K. Yeast ATP-binding cassette transporters: cellular cleaning pumps. Methods Enzymol., 400, 460-84 (2005).
20. Dietrich, J. a, McKee, A. E. & Keasling, J. D. High-throughput metabolic engineering: advances in small-molecule screening and selection. Annu. Rev. Biochem., 79, 563-590 (2010).
21. Chou, H. H. & Keasling, J. D. Programming adaptive control to evolve increased metabolite production. Nat. Commun. 4, 2595 (2013).
22. Duport, C., Spagnoli, R., Degryse, E. & Pompon, D. Self-sufficient biosynthesis of pregnenolone and progesterone in engineered yeast. Nat. Biotechnol. 16, 186-9 (1998).
23. Szczebara, F. M. et al., Total biosynthesis of hydrocortisone from a simple carbon source in yeast. Nat. Biotechnol. 21, 143-9 (2003).
24. Mali, P. et al., RNA-Guided Human Genome Engineering via Cas9. Science 11, 367-79 (2013).
25. DiCarlo, J. E. et al., Genome engineering in *Saccharomyces cerevisiae* using CRISPR-Cas systems. Nucleic Acids Res. 41, 1-8 (2013).
26. Gratz, S. J. et al., Genome engineering of Drosophila with the CRISPR RNA-guided Cas9 nuclease. Genetics 194, 1029-1035 (2013).
27. Hwang, W. Y. et al., Efficient genome editing in zebrafish using a CRISPR-Cas system., Nat. Biotechnol. 1-3 (2013). doi:10.1038/nbt.2501.
28. Fu, Y. et al., High-frequency off-target mutagenesis induced by CRISPR-Cas nucleases in human cells. Nat. Biotechnol. 31, 822-6 (2013).
29. Mali, P. et al., CAS9 transcriptional activators for target specificity screening and paired nickases for cooperative genome engineering. Nat. Biotechnol. 31, 833-8 (2013).
30. Pattanayak, V. et al., High-throughput profiling of off-target DNA cleavage reveals RNA programmed Cas9 nuclease specificity. Nat. Biotechnol. 31, 839-43 (2013).
31. Sakuma, Y. et al., Dual function of an *Arabidopsis* transcription factor DREB2A in water stress-responsive and heat-stress-responsive gene expression. Proc. Natl. Acad. Sci. U.S.A. 103, 18822-18827 (2006).

32. Todd, A. E., Orengo, C. A. & Thornton, J. M. Sequence and structural differences between enzyme and nonenzyme homologs. Structure 10, 1435-1451 (2002).
33. Agresti, J. J. et al., Ultrahigh-throughput screening in drop-based microfluidics for directed evolution. Proc. Natl. Acad. Sci. U.S.A. 107, 4004-9 (2010).
34. Alper, H., Miyaoku, K. & Stephanopoulos, G. Construction of lycopene-overproducing E. coli strains by combining systematic and combinatorial gene knockout targets. Nat. Biotechnol. 23, 612-6 (2005).
35. Dietrich, J. a., Shis, D. L., Alikhani, A. & Keasling, J. D. Transcription Factor-Based Screens and Synthetic Selections for Microbial Small-Molecule Biosynthesis. ACS Synth. Biol. 2, 47-58 (2013).
36. Zhang, F. & Keasling, J. Biosensors and their applications in microbial metabolic engineering. Trends Microbiol. 19, 323-9 (2011).
37. Banaszynski, L. A, Sellmyer, M. A., Contag, C. H., Wandless, T. J. & Thorne, S. H. Chemical control of protein stability and function in living mice. Nat. Med. 14, 1123-1127 (2008).
38. Fu, Y., Sander, J. D., Reyon, D., Cascio, V. M. & Joung, J. K. Improving CRISPR-Cas nuclease specificity using truncated guide RNAs. Nat. Biotechnol. 32, 279-84 (2014).
39. Cho, S. W. et al., Analysis of off-target effects of CRISPR Cas-derived RNA-guided endonucleases and nickases sup2. Genome Res. 24, 132-141 (2014).
40. Tsai, S. Q. et al., Dimeric CRISPR RNA-guided FokI nucleases for highly specific genome editing. Nat. Biotechnol. 32, 569-76 (2014).
41. Guilinger, J. P., Thompson, D. B. & Liu, D. R. Fusion of catalytically inactive Cas9 to FokI nuclease improves the specificity of genome modification. Nat. Biotechnol. 32, 577-82 (2014).
42. Ran, F. A. et al., Double nicking by RNA-guided CRISPR cas9 for enhanced genome editing specificity. Cell 154, 1380-1389 (2013).
43. Dow, L. E. et al., Inducible in vivo genome editing with CRISPR-Cas9. Nat. Biotechnol. 33, (2015).
44. Zetsche, B., Volz, S. E. S. & Zhang, F. A split-Cas9 architecture for inducible Genome editing and transcription modulation. Nat. Biotechnol. 33, 139-142 (2015).
45. Polstein, L. R. & Gersbach, C. a. A light-inducible CRISPR-Cas9 system for control of endogenous gene activation. Nat. Chem. Biol. 11, (2015).
46. Xie, J., Nair, A. & Hermiston, T. W. A comparative study examining the cytotoxicity of inducible gene expression system ligands in different cell types. Toxicol. Vitr. 22, 261-266 (2008).
47. Mandal, P. K. et al., Efficient Ablation of Genes in Human Hematopoietic Short Article Efficient Ablation of Genes in Human Hematopoietic Stem and Effector Cells using CRISPR/Cas9. Stem Cell 15, 643-652 (2014).
48. Wu, Y. et al., Correction of a genetic disease in mouse via use of CRISPR-Cas9. Cell Stem Cell 13, 659-662 (2013).
49. Schwank, G. et al., Functional repair of CFTR by CRISPR/Cas9 in intestinal stem cell organoids of cystic fibrosis patients. Cell Stem Cell 13, 653-658 (2013).
50. Gibson, D. G. et al., Enzymatic assembly of DNA molecules up to several hundred kilobases. Nat. Methods 6, 343-345 (2009).
51. Yoo, S.-D., Cho, Y.-H. & Sheen, J. Arabidopsis mesophyll protoplasts: a versatile cell system for transient gene expression analysis. Nat. Protoc. 2, 1565-1572 (2007).
52. Clough, S. J. & Bent, A. F. Floral dip: A simplified method for Agrobacterium-mediated transformation of Arabidopsis thaliana. Plant J. 16, 735-743 (1998).
53. Murashige, T. & Skoog, F. A revised medium for rapid growth and bio assays with tobacco tissue cultures. Physiol. Plant. 15, 473-497 (1962).
54. Gietz, R. D. & Schiestl, R. H. High-efficiency yeast transformation using the LiAc/SS carrier DNA/PEG method. Nat. Protoc. 2, 31-4 (2007).
55. Kunkel, T. a. Rapid and efficient site-specific mutagenesis without phenotypic selection., Proc. Natl. Acad. Sci. U.S.A. 82, 488-492 (1985).
56. Benatuil, L., Perez, J. M., Belk, J. & Hsieh, C.-M. M. An improved yeast transformation method for the generation of very large human antibody libraries. Protein Eng. Des. Sel. 23, 155-9 (2010).
57. Horecka, J. & Davis, R. W. The 50:50 method for PCR-based seamless genome editing in yeast. Yeast 26, 545-551 (2013).
58. Leskinen, P., Virta, M. & Karp, M. One-step measurement of firefly luciferase activity in yeast. Yeast 20, 1109-13 (2003).
59. Lee, M. E., DeLoache, W. C., Cervantes, B. & Dueber, J. E. A Highly-characterized Yeast Toolkit for Modular, Multi-part Assembly. ACS Synth. Biol. 150414151809002 (2015). doi:10.1021/sb500366v
60. Engler, C., Kandzia, R. & Marillonnet, S. A one pot, one step, precision cloning method with high throughput capability. PLoS One 3, (2008).

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the disclosure be limited to the specific values recited when defining a range.

From the foregoing, it will be appreciated that although specific examples have been described herein for purposes of illustration, various modifications may be made without deviating from the spirit or scope of this disclosure. It is therefore intended that the foregoing detailed description be regarded as illustrative rather than limiting, and that it be understood that it is the following claims, including all equivalents, that are intended to particularly point out and distinctly claim the claimed subject matter.

What is claimed is:

1. A conditionally stable biosensor comprising a homodimeric ligand binding domain (LBD) having conditionally-destabilizing mutations that is fused to a trans-activation domain (TAD) and a DNA binding domain (DBD), wherein the conditionally stable biosensor is stabilized when the ligand binding domain is bound to a cognate steroid, and wherein the DNA binding domain (DBD) binds to DNA and the trans-activation domain (TAD) activates transcription of a target gene.

2. The conditionally stable biosensor of claim 1, wherein the conditionally stable biosensor retains function when ported directly between yeast and mammalian cells.

3. The conditionally stable biosensor of claim 1, wherein the ligand binding domain is between an N-terminal DNA binding domain and a C-terminal transcriptional activation domain.

4. The conditionally stable biosensor of claim 1, wherein the ligand binding domain binds to digoxigenin.

5. The conditionally stable biosensor of claim 1, wherein the ligand binding domain binds to progesterone.

6. The conditionally stable biosensor of claim 1, wherein the trans-activation domain (TAD) is VP16.

7. The conditionally stable biosensor of claim 1, wherein the trans-activation domain (TAD) is VP64.

8. A cell line comprising the conditionally stable biosensor of claim 1.

9. The conditionally stable biosensor of claim 1 wherein the DNA binding domain (DBD) is a homodimeric DNA binding domain (DBD).

* * * * *